(12) United States Patent
Waldo et al.

(10) Patent No.: US 7,666,606 B2
(45) Date of Patent: Feb. 23, 2010

(54) PROTEIN-PROTEIN INTERACTION DETECTION SYSTEM USING FLUORESCENT PROTEIN MICRODOMAINS

(75) Inventors: Geoffrey S. Waldo, Santa Fe, NM (US); Stephanie Cabantous, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 81 days.

(21) Appl. No.: 11/295,368

(22) Filed: Dec. 5, 2005

(65) Prior Publication Data

US 2006/0257887 A1 Nov. 16, 2006

Related U.S. Application Data

(60) Provisional application No. 60/633,672, filed on Dec. 4, 2004.

(51) Int. Cl.
G01N 33/53 (2006.01)
C12Q 1/68 (2006.01)
C12N 15/00 (2006.01)
C12N 15/63 (2006.01)

(52) U.S. Cl. .............................. 435/7.1; 435/6; 435/455

(58) Field of Classification Search ........................ None
See application file for complete search history.

(56) References Cited

U.S. PATENT DOCUMENTS 6,428,951 B1 * 8/2002 Michnick et al. ................ 435/4

6,780,599 B2   8/2004 Hamilton et al. ............ 435/7.1

OTHER PUBLICATIONS

Waldo et al., U.S. Appl. No. 2005-0221343 published Oct. 6, 2005.
Ghosh et al., 2000, J. Am. Chem. Soc. 122: 5658.
Hu et al., 2002, Mol. Cell 9: 789.
Nagai et al., 2001, Proc. Natl. Acad. Sci. USA 98: 3197.
Ozawa et al., 2000, Anal. Chem. 72: 5151.
Ozawa et al., 2001, Anal. Chem. 73: 5866.
Umezawa, 2003, Chem. Rec. 3: 22.
Zhang et al., 2004, Cell 119: 137.
Cabantous et al., 2004, Nature Biotech DOI 10.1038/Nbt 1044.

* cited by examiner

*Primary Examiner*—Michele K. Joike
(74) *Attorney, Agent, or Firm*—Kenneth K. Sharples

(57) ABSTRACT

The invention provides a protein labeling and interaction detection system based on engineered fragments of fluorescent and chromophoric proteins that require fused interacting polypeptides to drive the association of the fragments, and further are soluble and stable, and do not change the solubility of polypeptides to which they are fused. In one embodiment, a test protein X is fused to a sixteen amino acid fragment of GFP ($\beta$-strand 10, amino acids 198-214), engineered to not perturb fusion protein solubility. A second test protein Y is fused to a sixteen amino acid fragment of GFP ($\beta$-strand 11, amino acids 215-230), engineered to not perturb fusion protein solubility. When X and Y interact, they bring the GFP strands into proximity, and are detected by complementation with a third GFP fragment consisting of GFP amino acids 1-198 (strands 1-9). When GFP strands 10 and 11 are held together by interaction of protein X and Y, they spontaneous association with GFP strands 1-9, resulting in structural complementation, folding, and concomitant GFP fluorescence.

8 Claims, 29 Drawing Sheets

FIG. 1 B

```
TCGAGTCCCTATCAGTGATAGAGATTGACATCCCTATCAGTGATAGAGATACTGAGCACATCAGCAGG
ACGCACTGACCGAGTTCATTAAAGAGGAGAAAGATACCCATGGGCAGCAGCCATCATCATCATCA
CAGCAGCGGCCTGGTGCCGCGCGGCAGCCATATGGGTGGCGGTTCTGGATCCGGAGGCACTAGTGGTG
GCGGCTCAGGTACCTAACTCGAGCACCACCACCACCACCACTGAGATCCGGCTGCTAACAAAGCCCGA
AAGGAAGCTGAGTTGGCTGCTGCCACCGCTGAGCAATAACTAGCATAACCTCTAGAGGCATCAAATAA
AACGAAAGGCTCAGTCGAAAGACTGGGCCTTTCGTTTTATCTGTTGTTTGTCGGTGAACGCTCTCCTG
AGTAGGACAAATCCGCCGCCCTAGACCTAGGCGTTCGGCTGCGGCGAGCGGTATCAGCTCACTCAAAG
GCGGTAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCGCCTT
TCTCCCTTCGGGAAGCGTGGCGCTTTCTCAATGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTATCCGGTAAC
TATCGTCTTGAGTCCAACCCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGAAAAAGAGTTGGTAGCTCT
TGATCCGGCAAACAAACCACCGCTGGTAGCGGTGGTTTTTTGTTTGCAAGCAGCAGATTACGCGCAG
AAAAAAAGGATCTCAAGAAGATCCTTTGATCTTTTCTACGGGGTCTGACGCTCAGTGGAACGAAAACT
CACGTTAAGGGATTTTGGTCATGACTAGC [Start_Module_1:_GCTTGGATTCTCACCAATAAA
AAACGCCCGGCGGCAACCGAGCGTTCTGAACAAATCCAGATGGAGTTCTGAGGTCATTACTGGATCTA
TCAACAGGAGTCCAAGC_End_Module_1_][_Start_Module_2:_TTAAGACCCACTTTCACA
TTTAAGTTGTTTTTCTAATCCGTATATGATCAATTCAAGGCCGAATAAGAAGGCTGGCTCTGCACCTT
GGTGATCAAATAATTCGATAGCTTGTCGTAATAATGGCGGCATACTATCAGTAGTAGGTGTTTCCCTT
TCTTCTTTAGCGACTTGATGCTCTTGATCTTCCAATACGCAACCTAAAGTAAAATGCCCCACAGCGCT
GAGTGCATATAATGCATTCTCTAGTGAAAAACCTTGTTGGCATAAAAAGGCTAATTGATTTTCGAGAG
TTTCATACTGTTTTTCTGTAGGCCGTGTACCTAAATGTACTTTTGCTCCATCGCGATGACTTAGTAAA
GCACATCTAAAACTTTTAGCGTTATTACGTAAAAAATCTTGCCAGCTTTCCCCTTCTAAAGGGCAAAA
GTGAGTATGGTGCCTATCTAACATCTCAATGGCTAAGGCGTCGAGCAAAGCCCGCTTATTTTTTACAT
GCCAATACAATGTAGGCTGCTCTACACCTAGCTTCTGGGCGAGTTTACGGGTTGTTAAACCTTCGATT
CCGACCTCATTAAGCAGCTCTAATGCGCTGTTAATCACTTTACTTTTATCTAATCTGGACAT_End_M
odule_2_][_Start_Module_3:_CATTAATGTTTATT_End_Module_3_]GAGCTCTCGAAC
CCCAGAGTCCCGCA[_Start_Module_4:_TTATTTGCCGACTACCTTGGTGATCTCGCCTTTCAC
GTAGTGGACAAATTCTTCCAACTGATCTGCGCGCGAGGCCAAGCGATCTTCTTCTTGTCCAAGATAAG
CCTGTCTAGCTTCAAGTATGACGGGCTGATACTGGGCCGGCAGGCGCTCCATTGCCCAGTCGGCAGCG
ACATCCTTCGGCGCGATTTTGCCGGTTACTGCGCTGTACCAAATGCGGGACAACGTAAGCACTACATT
TCGCTCATCGCCAGCCCAGTCGGGCGGCGAGTTCCATAGCGTTAAGGTTTCATTTAGCGCCTCAAATA
GATCCTGTTCAGGAACCGGATCAAAGAGTTCCTCCGCCGCTGGACCTACCAAGGCAACGCTATGTTCT
CTTGCTTTTGTCAGCAAGATAGCCAGATCAATGTCGATCGTGGCTGGCTCGAAGATACCTGCAAGAAT
GTCATTGCGCTGCCATTCTCCAAATTGCAGTTCGCGCTTAGCTGGATAACGCCACGGAATGATGTCGT
CGTGCACAACAATGGTGACTTCTACAGCGCGGAGAATCTCGCTCTCTCCAGGGGAAGCCGAAGTTTCC
AAAAGGTCGTTGATCAAAGCTCGCCGCGTTGTTTCATCAAGCCTTACGGTCACCGTAACCAGCAAATC
AATATCACTGTGTGGCTTCAGGCCGCCATCCACTGCGGAGCCGTACAAATGTACGGCCAGCAACGTCG
GTTCGAGATGGCGCTCGATGACGCCAACTACCTCTGATAGTTGAGTCGATACTTCGGCGATCACCGCT
TCCCTCATGATGTTTAACTTTGTTTTAGGGCGACTGCCCTGCTGCGTAACATCGTTGCTGCTCCATAA
CATCAAACATCGACCCACGGCGTAACGCGCTTGCTGCTTGGATGCCCGAGGCATAGACTGTACCCCAA
AAAAACATGTCATAACAAGCCATGAAAACCGCCACTGCGCCGTTACCATGCGAAACGATCCTCAT_En
d_Module_4_][_Start_Module_5:_CCTGTCTCTTGATCAGATCTTGATCCCCTGCGCCATCA
GATCCTTGGCGGCAAGAAAGCCATCCAGTTTACTTTGCAGGGCTTCCCAACCTTACCAGAGGGCGCCC
CAGCTGGCAATTCC_End_Module_5_]GACGTCTAAGAAACCATTATTATCATGACATTAACCTAT
AAAAATAGGCGTATCACGAGGCCCTTTCGTCTTCACC
[SEQ ID NO: 22]
```

FIG. 3
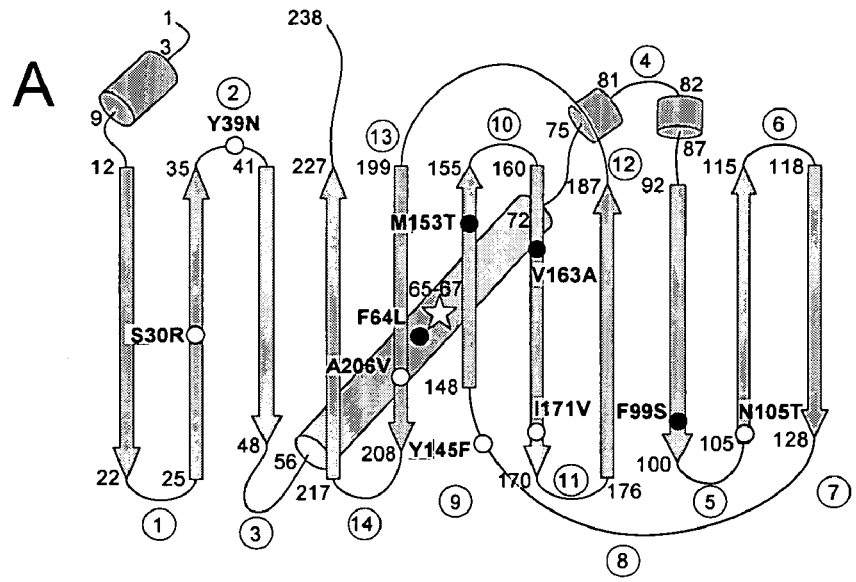
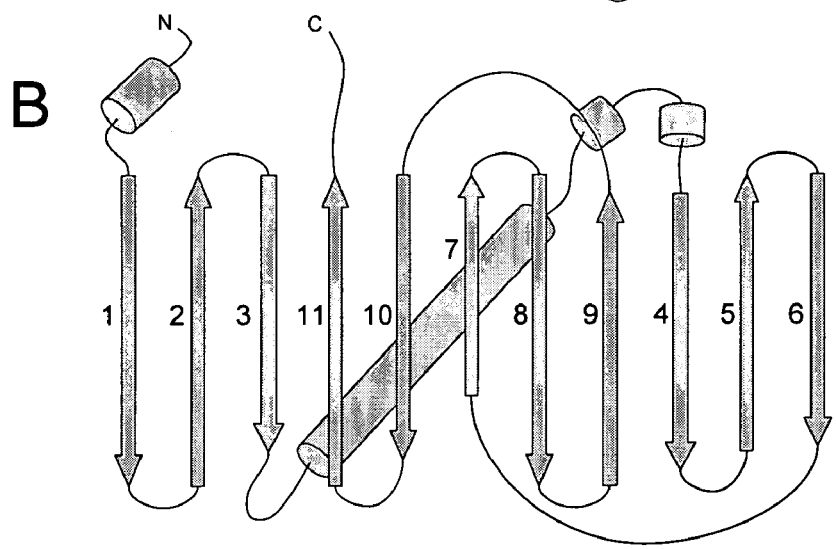
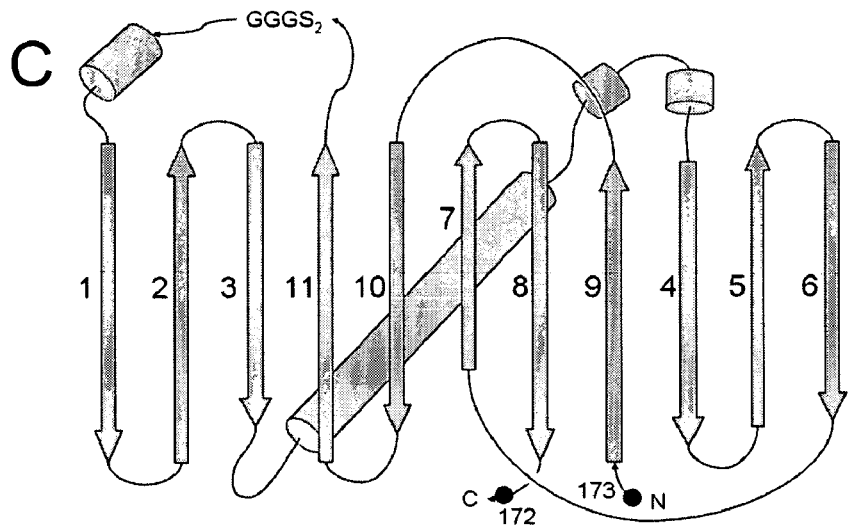

FIG. 4
Folding Reporter         Superfolder
157   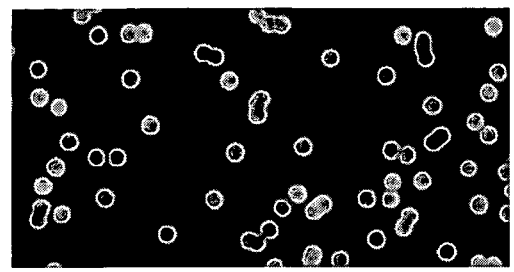
172  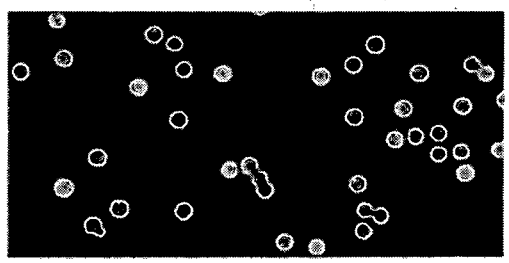 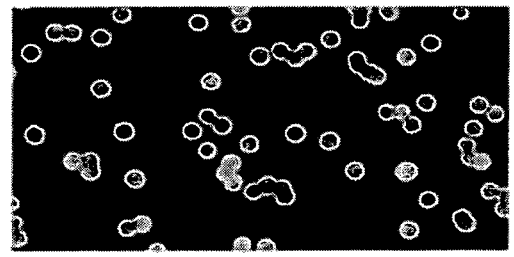

FIG. 17
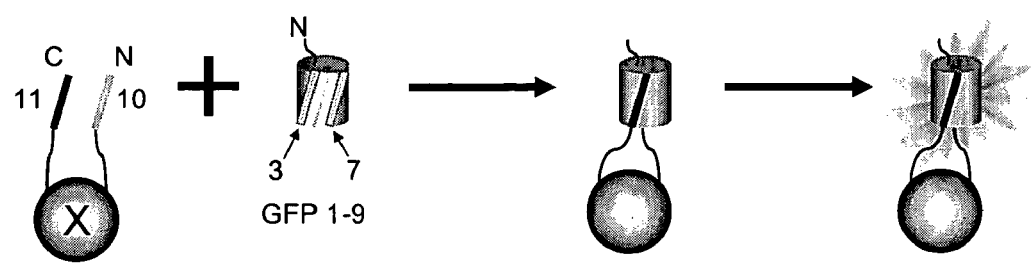
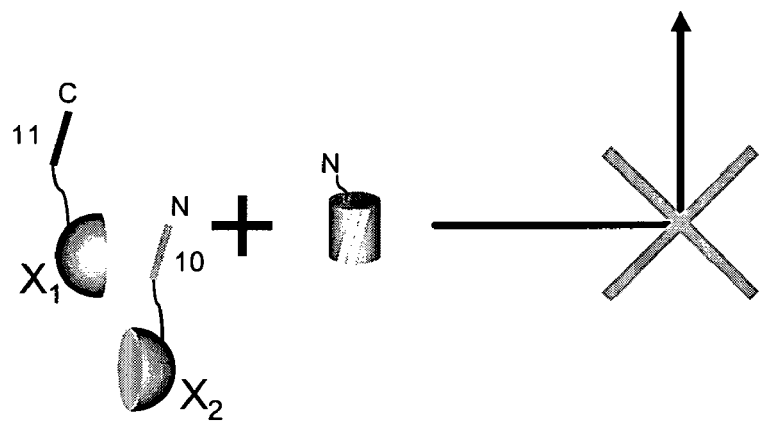

FIG. 18A (left)

```
                    10         20         30         40
           ....|....|....|....|....|....|....|....|....|....:
[SEQ ID NO: 55] S   YTMGLPDNHYLSTQSVLSKDPNGTGGGSGGGGSHMGGGSGS
[SEQ ID NO: 56] M1  ...D............TI.L.......V............
[SEQ ID NO: 57] M2  ...D............TI.L.......V............
[SEQ ID NO: 58] M3  ...D............TI.L.......V............
[SEQ ID NO: 59] M4  ...D............TI.L......DV............
[SEQ ID NO: 27] M5  ...D............TI.L.......V............
[SEQ ID NO: 60] M6  ...D............TI.L.........D.C..D.....
```

FIG. 18A (right)

```
         40        50        60        70        80
         |....|....|....|....|....|....|....|....|....|....
         GGGSGGGGSTSEKRDHMVLLEFVTAAGITGAS*LENS
         ................................Y.......D............HHHHHH*DPAANK
         ....E...........G...............Y.......D............
         ................................Y....................
         ....D...........G...............Y.......D............
         ................................Y....................
         ................G...............Y....................
```

FIG. 18 B

```
                              STRAND 10
              195              200              205              210
[SEQ ID NO: 61]  G  P  V  L  L  P  D  N  H  Y  L  S  T  Q  T  V  L  S  K  D  P  N  E  K  *
[SEQ ID NO: 62] GGCCCTGTCCTTTTACCANNNAACCATTACCTGTCGACA                                      03081301
[SEQ ID NO: 63]      CCTGTCCTTTTACCAGACNNNCATTACCTGTCGACACAA                                  03081303
[SEQ ID NO: 64]        GTCCTTTTACCAGACAACNNNTACCTGTCGACACAAACT                                03081305
[SEQ ID NO: 65]            CTTTTACCAGACAACCATNNNCTGTCGACACAAACTGTC                            03081307
[SEQ ID NO: 66]              TTACCAGACAACCATTACNNNTCGACACAAACTGTCCTT                          03081309
[SEQ ID NO: 67]                CCAGACAACCATTACCTGNNNACACAAACTGTCCTTCG                        03081311
[SEQ ID NO: 68]                  GACAACCATTACCTGTCGNNNCAAACTGTCCTTTCGAAA                     03081313
[SEQ ID NO: 69]                    AACCATTACCTGTCGACANNNACTGTCCTTTCGAAAGAT                   03081315
[SEQ ID NO: 70]                      CATTACCTGTCGACACAANNNGTCCTTTCGAAAGATCCC                 03081317
[SEQ ID NO: 71]                        TACCTGTCGACACAAACTNNNCTTTCGAAAGATCCCAAC               03081319
[SEQ ID NO: 72]                          CTGTCGACACAAACTGTCNNNTCGAAAGATCCCAACGAA             03081321
[SEQ ID NO: 73]                            TCGACACAAACTGTCCTTNNNAAAGATCCCAACGAAAAG           03081323
[SEQ ID NO: 74]                              ACACAAACTGTCCTTTCGNNNGATCCCAACGAAAAGTAA         03081325
[SEQ ID NO: 75]                                CAAACTGTCCTTTCGAAANNNCCCAACGAAAAGTAAGGT       03081327
[SEQ ID NO: 76] GGCCCCTGTCCTTTTACCAGACAACCATTACCTGTCGACACAAACTGTCCTTTCGAAAGATCCCAACGAAAAGTAAGGTACC
[SEQ ID NO: 77] CCGGGACAGGAAAATGGTCTGTTGGTAATGGACAGCTGTGTTTGACAGGAAAGCTTTCTAGGGTTGCTTTTCATTCCATGG
[SEQ ID NO: 78]                                       GAAAGCTTTCTAGGGTTGCTTTTCATTCCATGG     03081336
```

FIG. 19

```
[SEQ ID NO: 55]  YTMGLPDNHYLSTQSVLSKDPNGTGGGSGGGSGGGSGGGSHMGGGSGGGSGGGSGGGSTSEKRDHMVLLEFVTAAGITGAS*LENS
[SEQ ID NO: 27]  YTMDLPDNHYLSTQTILLKDLNGTGVGSGGGSGGGSHMGGGSGGGSGGGSGGGSTSEKRDHMVLLEYVTAAGITDAS*LEHHHHHH*DPAANK
[SEQ ID NO: 79]           XDLXDDXYLSTQTILSKDLNGTGVGSGGGSHMKLQVALD             A10
[SEQ ID NO: 80]           PXDLXDDXYLSTQTILSKDLNGTGVGSGGGSHMKLQVALD            C10
[SEQ ID NO: 81]           PXDLXDDXYLSTQTILSKDLNGTGVGSGGGSHMKLQVALDL           E10
[SEQ ID NO: 82]           IPMDLPDDHYLSTQTILSKDLNGTGVGSGGGSHMKLQVALDLVD        G10
[SEQ ID NO: 83]             DLPDDHYLSTQTILSKDLNGTGVGSDGGSHMKLQVALDLVD        A11
[SEQ ID NO: 84]           IMPDLPDDHYLSTQTILSKDLNGTGVGSGGGSHMKLQVALDLV         C11
[SEQ ID NO: 85]           IPMDLPDDHYLSTQTILSKDLNGTGVGSGGGSHMKLQVALDLVDL       E11
[SEQ ID NO: 86]           IMPDLPDDHYLSTQTILSKDLNGTGVGSGGGSHMKLQVALDLVD        G11
```

FIG. 24
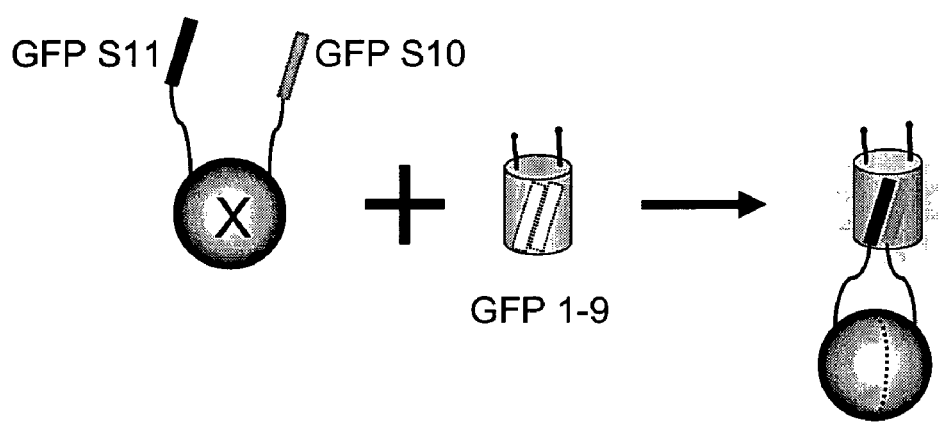
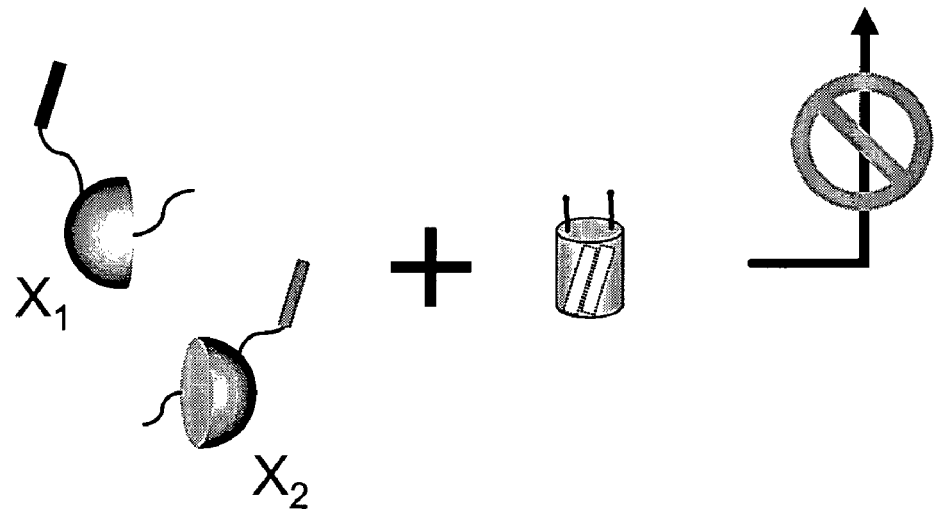

FIG. 26
a
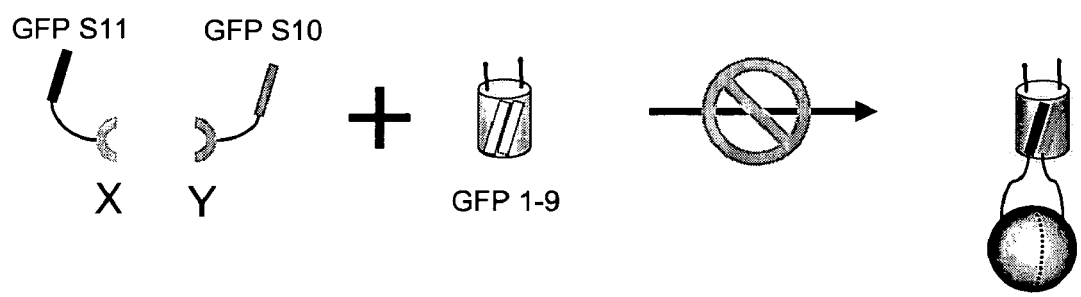
b
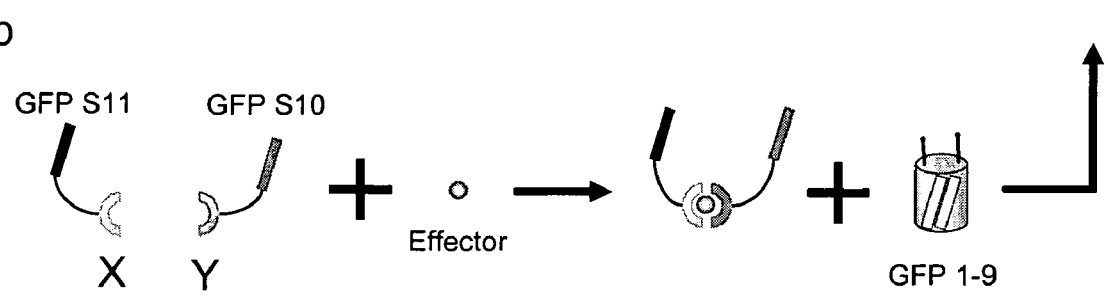

PROTEIN-PROTEIN INTERACTION DETECTION SYSTEM USING FLUORESCENT PROTEIN MICRODOMAINS

RELATED APPLICATIONS

This patent application claims the benefit of the filing date of U.S. Provisional patent application No. 60/633,672 filed Dec. 4, 2004.

STATEMENT AS TO RIGHTS TO INVENTIONS MADE UNDER FEDERALLY SPONSORED RESEARCH OR DEVELOPMENT

This invention was made with government support under Contract No. W-7405-ENG-36 awarded by the United States Department of Energy to The Regents of The University of California. The government has certain rights in this invention.

BACKGROUND OF THE INVENTION

GFP and its numerous related fluorescent proteins are now in widespread use as protein tagging agents (for review, see Verkhusha et al., 2003, *GFP-like fluorescent proteins and chromoproteins of the class Anthozoa*. In: Protein Structures: Kaleidescope of Structural Properties and Functions, Ch. 18, pp. 405-439, Research Signpost, Kerala, India). In addition, GFP has been used as a solubility reporter of terminally fused test proteins (Waldo et al., 1999, *Nat. Biotechnol.* 17:691-695; U.S. Pat. No. 6,448,087, entitled 'Method for Determining and Modifying Protein/Peptide Solubility'). GFP-like proteins are an expanding family of homologous, 25-30 kDa polypeptides sharing a conserved 11 beta-strand "barrel" structure. The GFP-like protein family currently comprises some 100 members, cloned from various *Anthozoa* and *Hydrozoa* species, and includes red, yellow and green fluorescent proteins and a variety of non-fluorescent chromoproteins (Verkhusha et al., supra). A wide variety of fluorescent protein labeling assays and kits are commercially available, encompassing a broad spectrum of GFP spectral variants and GFP-like fluorescent proteins, including DsRed and other red fluorescent proteins (Clontech, Palo Alto, Calif.; Amersham, Piscataway, N.J.).

GFP fragment reconstitution systems have been described, mainly for detecting protein-protein interactions, but none are capable of unassisted self-assembly into a correctly-folded, soluble and fluorescent re-constituted GFP, and no general split GFP folding reporter system has emerged from these approaches. For example, Ghosh et al, 2000, reported that two GFP fragments, corresponding to amino acids 1-157 and 158-238 of the GFP structure, could be reconstituted to yield a fluorescent product, in vitro or by coexpression in *E. coli*, when the individual fragments were fused to coiled-coil sequences capable of forming an antiparallel leucine zipper (Ghosh et al., 2000, *Antiparallel leucine zipper-directed protein reassembly: application to the green fluorescent protein*. J. Am. Chem. Soc. 122: 5658-5659). Likewise, U.S. Pat. No. 6,780,599 describes the use of helical coils capable of forming anti-parallel leucine zippers to join split fragments of the GFP molecule. The patent specification establishes that reconstitution does not occur in the absence of complementary helical coils attached to the GFP fragments. In particular, the specification notes that control experiments in which GFP fragments without leucine zipper pairs "failed to show any green colonies, thus emphasizing the requirement for the presence of both NZ and CZ leucine zippers to mediate GFP assembly in vivo and in vitro."

Similarly, Hu et al., 2002, showed that the interacting proteins bZIP and Rel, when fused to two fragments of GFP, can mediate GFP reconstitution by their interaction (Hu et al., 2002, *Visualization of interactions among bZIP and Rel family proteins in living cells using bimolecular fluorescence complementation*. Mol. Cell 9: 789-798). Nagai et al., 2001, showed that fragments of yellow fluorescent protein (YFP) fused to calmodulin and M13 could mediate the reconstitution of YFP in the presence of calcium (Nagai et al., 2001, *Circularly permuted green fluorescent proteins engineered to sense $Ca^{2+}$*. Proc. Natl. Acad. Sci. USA 98: 3197-3202). In a variation of this approach, Ozawa at al. fused calmodulin and M13 to two GFP fragments via self-splicing intein polypeptide sequences, thereby mediating the covalent reconstitution of the GFP fragments in the presence of calcium (Ozawa et al., 2001, *A fluorescent indicator for detecting protein-protein interactions in vivo based on protein splicing*. Anal. Chem. 72: 5151-5157; Ozawa et al., 2002, *Protein splicing-based reconstitution of split green fluorescent protein for monitoring protein-protein interactions in bacteria: improved sensitivity and reduced screening time*. Anal. Chem. 73: 5866-5874). One of these investigators subsequently reported application of this splicing-based GFP reconstitution system to cultured mammalian cells (Umezawa, 2003, Chem. Rec. 3: 22-28). More recently, Zhang et al., 2004, showed that the helical coil split GFP system of Ghosh et al., 2000, supra, could be used to reconstitute GFP (as well as YFP and CFP) fluorescence when coexpressed in *C. elegans*, and demonstrated the utility of this system in confirming coexpression in vivo (Zhang et al., 2004, *Combinatorial marking of cells and organelles with reconstituted fluorescent proteins*. Cell 119: 137-144).

Although the aforementioned GFP reconstitution systems provide advantages over the use of two spectrally distinct fluorescent protein tags, they are limited by the size of the fragments and correspondingly poor folding characteristics (Ghosh et al., Hu et al., supra), the requirement for a chemical ligation step (Ozawa et al., 2001, 2002 supra), and co-expression or co-refolding to produce detectable folded and fluorescent GFP (Ghosh et al., 2000; Hu et al., 2001, Zhang et al. 2004 supra). Poor folding characteristics limit the use of these fragments to applications wherein the fragments are simultaneously expressed or simultaneously refolded together. Such fragments are not useful for in vitro assays requiring the long-term stability and solubility of the respective fragments prior to complementation. An example of an application for which such split protein fragments are not useful would be the quantitative analysis the interaction of polypeptides tagged with the members of the split protein pair. Another example would be the detection of protein interactions wherein the tagged polypeptides are not simultaneously expressed, or in which interactions are induced after expression by the addition of a small molecule effector such as a drug.

An ideal protein interaction detection system would be genetically encoded, could work both in vivo and in vitro, provide a sensitive analytical signal, and would not require external chemical reagents or substrates. In U.S. Pat. No. 6,428,951 (Michnick et al.), describe various split protein complementation assays for detected protein-protein interactions. However, the split proteins specified are poorly folded and mostly insoluble (see gels of fragments of dihydrofolate reductase). In that application, the fragments of GFP specified are also poorly folded. Michnick et al. describes an approach to improve the folding of the fragments of split proteins wherein the split proteins are fused to known interacting domains, and the split proteins are mutated, and libraries are co-expressed within cells and selected for the function associated with the reconstituted split protein. The DHFR is used as an exemplary case. However, the fact that the specified DHFR fragments used in the claimed embodiment are mostly insoluble when expressed separately, despite being capable of complementation and enzymatic activity when reassembled using fused coiled-coils argues that this directed evolution approach based on co-expression of complementary fragments is not sufficiently stringent to select for soluble and stable fragments. Further, in co-owned, co-pending U.S. patent application Ser. No. 10/973,693 filed Oct. 25, 2004, Waldo et al. demonstrate that co-expression of insoluble split-GFP fragments can lead to complementation, whereas complementation does not occur when the fragments are separately expressed. Waldo et al. further show that a directed evolution using sequential expression of fragments of split proteins can be used to select more soluble, stable versions of split protein fragments. This sequential expression is in marked contrast to the co-expression specified by Michnick et al. A split fluorescent protein tagging system that does not aggregate prior to association and does not change the solubility of the tagged polypeptides has been recently described (Cabantous et. al., 2004, *Protein tagging and detection using engineered self-assembling fragments of green fluorescent protein*. Nature Biotechnology DOI 10.1038/Nbt1044). However, the fragments are capable of spontaneously self-associating without the need for fused interacting protein domains. Split GFP fragments that remain soluble prior to association, do not change the solubility of fused target proteins, and are also dependent on fused interacting domains for complementation, are needed and are addressed by this invention.

SUMMARY OF THE INVENTION

The invention provides a protein labeling and interaction detection system based on engineered fragments of fluorescent and chromophoric proteins that require fused interacting polypeptides to drive the association of the fragments, and further are soluble and stable, and do not change the solubility of polypeptides to which they are fused. The system of the invention is exemplified with various combinations of fragments derived from *Aequorea victoria* Green Fluorescent Protein (GFP), which are used to detect and quantify protein interactions in multiple assay formats, both in vitro and in vivo.

In one particular embodiment, a test protein X is fused to a sixteen amino acid fragment of GFP (β-strand 10, amino acids 198-214), engineered to not perturb fusion protein solubility. A second test protein Y is fused to a sixteen amino acid fragment of GFP (β-strand 11, amino acids 215-230), engineered to not perturb fusion protein solubility. When X and Y interact, they bring the GFP strands into proximity, and are detected by complementation with a third GFP fragment consisting of GFP amino acids 1-198 (strands 1-9). When GFP strands 10 and 11 are held together by interaction of protein X and Y, they spontaneous association with GFP strands 1-9, resulting in structural complementation, folding, and concomitant GFP fluorescence.

The split-GFP system is very simple, requires no external reagents, provides a sensitive analytical signal proportional to the amount of interacting tagged protein, does not perturb fusion protein folding and solubility, and works both in vivo and in vitro. No other existing protein tagging and detection system combines these capabilities. As detailed in the Examples, infra, the split-GFP system can be used to quantify protein interactions in multiwell plates, and to monitor protein interactions in living cells such as *Escherichia coli*, yeast, and mammalian cells.

The split GFP system of the invention will be particularly useful for assaying protein interactions, for quantifying protein interactions, and as reporter assays for monitoring the success of directed evolution strategies aimed at improving the folding and solubility of particular interacting polypeptides or proteins, and for engineering the strength of protein-protein interactions including binding ligands and targets. Additionally, the systems of the invention may be used to assay for factors that inhibit and/or promote interactions of proteins, specifically in high throughput drug development formats.

Methods for generating fragments of a reporter protein that require interacting domains for folding and reconstitution and are also soluble are also provided. These methods are exemplified by the generation of engineered fragments of GFP, and may be used to create soluble fragments of other GFP-like fluorescent and non-fluorescent proteins that require fused interacting domains for association and folding.

BRIEF DESCRIPTION OF THE DRAWINGS

FIG. 3 shows the topological secondary structure diagram of the eleven beta-stranded GFP family members. (A) Strands and numbering of amino acids. Circled number corresponds to index of the turn between strands (and a preferred site for splitting the protein), dark circles are the folding reporter mutations, and white circles are the superfolder GFP mutations. (B) shows numbering convention of the eleven beta strands. (C) shows a circular permutant GFP made by connecting the N and C termini by a short flexible linker and providing a new start codon at amino acid 173, and stop codon after amino acid 172.

FIG. 4 shows fluorescence images of in vivo complementation by indicated GFP fragments at split position 157 or 172, (i.e. 1-156+157-238 and 1-171+172-238), co-expressed from compatible plasmids in *E. coli* colonies on plates. Left column shows fragments derived from folding reporter GFP, right column shows same fragments derived from superfolder GFP. As expected, the superfolder fragments work betted and give brighter clones, consistent with the improved folding of superfolder GFP vs. folding reporter GFP.

FIG. 17 shows the principle of a sandwich tag format in which a test protein X is expressed as a fusion between two domains of GFP (strand 10 and strand 11) and detected by a third domain of GFP (GFP 1-9 OPT). (a) complementation occurs efficiently when the tag strands are both linked by an intact target protein X. (b) complementation would be inefficient if the tag strands are separated.

FIG. 18(A) shows the sequences of six optima from evolution of (GFP S10)-L1-NdeI::GGGSGSGG::BamHI-L2-(GFP S11) using GFP 1-9 OPT as complementation target, following the starting sequence (top sequence). GFP S10 and GFP S11 are shown underlined. Mutations in the six optima relative to the starting sequence are shown. Fifth optimum is preferred, and called (GFP S10 SM5)-L1-Nde-1::X::BamHI-L2-(GFP S11 SM5), where X is the target protein of interest, (B) shows the fourteen mutagenic degenerate primers used to introduce mutations at the target sites of GFP S10 underneath the coding sequence for strand 10: the strand 10 nucleotide coding sequence and its complement are also shown, along with the reverse primer sequence (bottom sequences).

FIG. 19 shows the reference sequence (GFP S10)-L1-NdeI::GGGSGSGG::BamHI-L2-(GFP S11), the optimum sequence from FIG. 18A (GFP S10 SM5)-L1-Nde-1::X::BamHI-L2-(GFP S11 SM5), and the sequences of eight optima (GFP S10)-L1-Nde-1::HPS::BamHI-L2-(GFP S11 SM5). Mutations in the target strand GFP S10 which improve the solubility of the starting sequence (GFP S10 SM5)-L1-Nde-1::HPS::BamHI-L2-(GFP S11 SM5) are boxed. Each of the eight optima sequences continue through the HPS coding sequence and resume with the BamHI site, followed by the flexible linker sequence and GFP S11 SM5 (see the end of the second sequence in list).

FIG. 24 shows an alternative strategy for discovering soluble, non-perturbing GFP fragments that also require interacting domains for reconstitution and folding. (a) existing GFP fragments F1 and F2 are poorly folded and fail to complement. (b) F1 and F2 are engineered by directed evolution to discover better-folded versions that remain soluble, do not aggregate, and do not perturb fusion protein folding and solubility, and thus are capable of spontaneous association. These mutations are shown by white dots. In (c), additional mutations are discovered that reduce or eliminate spontaneous association (black dots). The variants are fused to domains which interact in the presence of a small effector. A large pool of variants that are not fluorescent in the absence of the effector are isolated from cells by flow cytometry or screening on plates. (d) These variants are then exposed to the effector, and those that become fluorescent in the presence of the effector are isolated. These bind and fold to become fluorescent only when fused to interacting domains. This eliminates the false negatives in step (c) that are misfolded or incapable of complementation even in the presence of fused domains, and has the advantage that the mutants do not have to be subcloned into new vectors between steps c and d.

FIG. 26 shows the three-body complementation strategy used to detect protein interactions. In (a), GFP s10 and GFP S11 are fused to interacting proteins X and Y. Upon interaction of X and Y, GFP s10 and GFP s11 become tethered, and the entropy is lowered sufficiently to allow binding and folding with GFP s1-9 to make the fluorescent GFP. In (b), X and Y interact with a third protein or target Z, causing the tethering of GFP s10 and GFP s11, and reducing the entropy sufficiently to allow efficient complementation with GFP s1-9 and formation of the folded, fluorescent GFP.

FIG. 27 shows the three-body complementation strategy used to detect effector-induced protein interactions. In (a), GFP s10 and GFP S11 are fused to proteins X and Y which interact in the presence of an effector. In the absence of the effector, GFP s10 and GFP s11 are not tethered and the entropy is too high for efficient complementation with GFP s1-9. In (b), the addition of the effector molecule causes X and Y to bind, tethering GFP s10 and GFP s11, and the entropy is lowered sufficiently to allow binding and folding with GFP s1-9 to make the fluorescent GFP.

FIG. 28 In vitro protein-protein interaction assay: Rapamycin-induced protein-protein interactions using three fragment complementation assay. Fluorescence of bacterial plates. See Example 34.

FIG. 29 In vitro protein-protein interaction assay: Rapamycin-induced protein-protein interactions using three fragment complementation assay. Final fluorescence values following overnight incubation in presence or absence of rapamycin. See Example 34.

DETAILED DESCRIPTION OF THE INVENTION

Definitions

Figure 1:
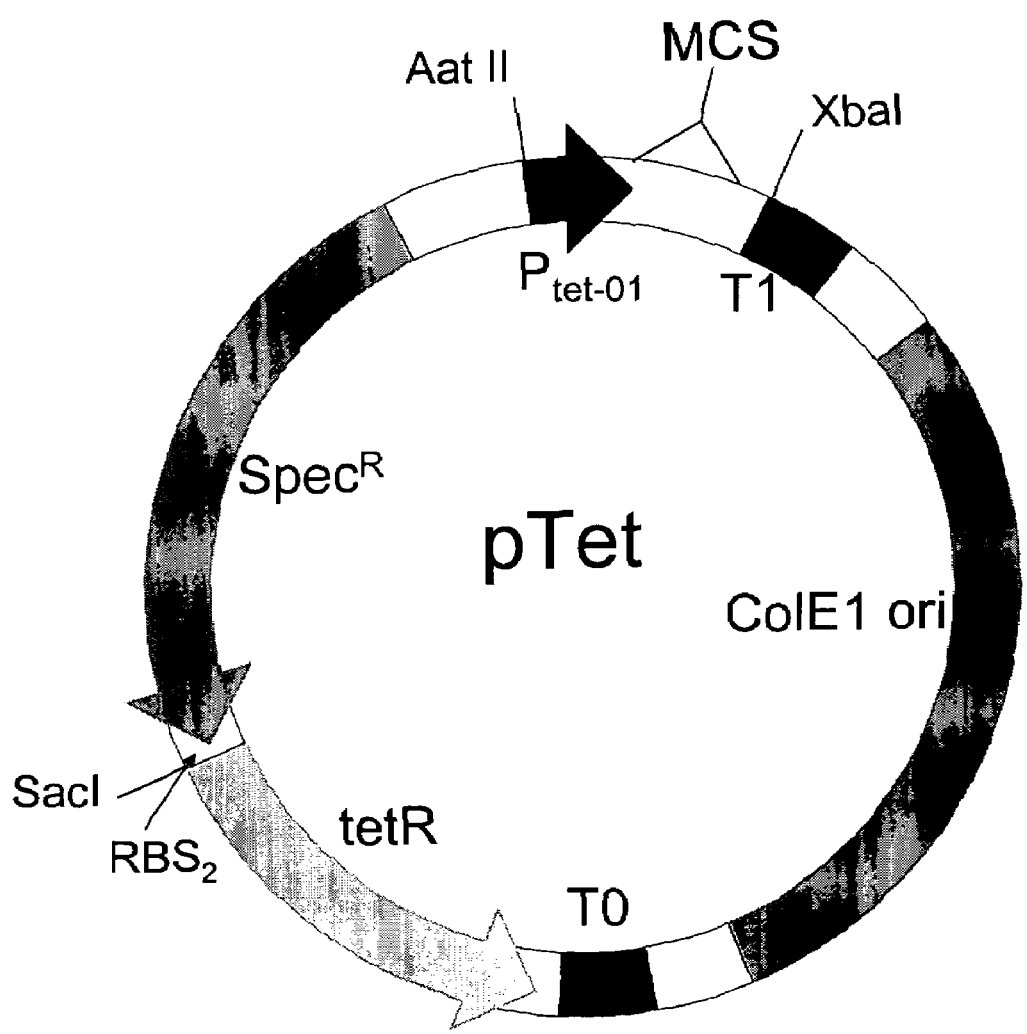
FIG. 1A shows a schematic diagram of the pTET-SpecR plasmid, which is a modified version of the pPROTet.6×HN vector available from Clontech (Palo Alto, Calif.). The chloramphenicol resistance gene was replaced by the spectinomycin resistance marker under the control of the kanamycin promoter of the pPROlar resistance marker (pPROlar plasmid from Clontech, Palo Alto, Calif.). On the same cistron is encoded the tetracycline repressor upstream of the T0 transcription termination sequence. The amount of translated repressor is regulated by a weak Shine-Delgarno sequence downstream of SacI.
FIG. 1B shows the different elements of the engineered pTET-SpecR plasmid SEQ ID NO. 22. Sequence in bold=v1 cloning cassette for expressing genes under tet promoter, flanked by NcoI CCATGG, and KpnI GGTACC. Regions of interest are boxed: Module 1=T0 transcription terminator for the SpecR-tetR cistron; Module 2=tetR repressor gene; Module 3=RBS controlling tetR translation; Module 4=spectinomycin (specR) gene; Module 5=kanamycin promoter element from PROLAR vector (Clontech, Palo Alto, Calif.).

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

A "fluorescent protein" as used herein is an *Aequorea victoria* green fluorescent protein (GFP), structural variants of GFP (i.e., circular permutants, monomeric versions), folding variants of GFP (i.e., more soluble versions, superfolder versions), spectral variants of GFP (i.e., YFP, CFP), and GFP-like fluorescent proteins (i.e., DsRed). The term "GFP-like fluorescent protein" is used to refer to members of the Anthozoa fluorescent proteins sharing the 11-beta strand "barrel" structure of GFP, as well as structural, folding and spectral variants thereof. The terms "GFP-like non-fluorescent protein" and "GFP-like chromophoric protein" (or, simply, "chromophoric protein" or "chromoprotein") are used to refer to the *Anthozoa* and *Hydrozoa* chromophoric proteins sharing the 11-beta strand "barrel" structure of GFP, as well as structural, folding and spectral variants thereof. GFP-like proteins all share common structural and functional characteristics, including without limitation, the capacity to form internal chromophores without requiring accessory co-factors, external enzymatic catalysis or substrates, other than molecular oxygen.

A "variant" of a fluorescent protein is derived from a "parent" fluorescent protein and retains the 11 beta-strand barrel structure as well as intrinsic fluorescence, and is meant to include structures with amino acid substitutions, deletions or insertions that may impart new or modified biological properties to the protein (i.e., greater stability, improved solubility, improved folding, shifts in emission or excitation spectra, reduced or eliminated capacity to form multimers, etc) as well as structures having modified N and C termini (i.e., circular permutants).

The term "complementing fragments" or "complementary fragments" when used in reference to a reporter polypeptide refer to fragments of a polypeptide that are individually inactive (i.e., do not express the reporter phenotype), wherein binding of the complementing fragments restores reporter activity. The terms "self-complementing", "self-assembling", and "spontaneously-associating", when used to describe two or more fluorescent (or chromophoric) protein fragments, mean that the fragments are capable of reconstituting into an intact, fluorescent (or chromophoric) protein when the individual fragments are soluble.

The "MMDB Id: 5742 structure" as used herein refers to the GFP structure disclosed by Ormo & Remington, MMDB Id: 5742, in the Molecular Modeling Database (MMDB), PDB Id: 1EMA PDB Authors: M. Ormo & S. J. Remington PDB Deposition: 1 Aug. 1996 PDB Class: Fluorescent Protein PDB Title: Green Fluorescent Protein From Aequorea Victoria. The Protein Data Bank (PDB) reference is Id PDB Id: 1 EMA PDB Authors: M. Ormo & S. J. Remington PDB Deposition: 1 Aug. 1996 PDB Class: Fluorescent Protein PDB Title: Green Fluorescent Protein From *Aequorea victoria*. (see, e.g., Ormo et al. "Crystal structure of the Aequorea Victoria green fluorescent protein." Science 1996 Sep. 6; 273(5280):1392-5; Yang et al, "The molecular structure of green fluorescent protein." *Nat Biotechnol*. 1996 Oct. 14 (10): 1246-51).

"Root mean square deviation" ("RMSD") refers to the root mean square superposition residual in Angstroms. This number is calculated after optimal superposition of two structures, as the square root of the mean square distances between equivalent C-alpha-atoms.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "as determined by maximal correspondence" in the context of referring to a reference SEQ ID NO means that a sequence is maximally aligned with the reference SEQ ID NO over the length of the reference sequence using an algorithm such as BLAST set to the default parameters. Such a determination is easily made by one of skill in the art.

The term "link" as used herein refers to a physical linkage as well as linkage that occurs by virtue of co-existence within a biological particle, e.g., phage, bacteria, yeast or other eukaryotic cell.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as a fluorescent binding ligand and a display protein or nucleic acid, and serves to place the two molecules in a preferred configuration.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "isolated" and "purified" refer to material which is substantially or essentially free from components which normally accompany it as found in its native state. However, the term "isolated" is not intended refer to the components present in an electrophoretic gel or other separation medium. An isolated component is free from such separation media and in a form ready for use in another application or already in use in the new application/milieu.

Split-Fluorescent and Chromophoric Protein Systems

The protein-protein interaction assays of the invention utilize split-fluorescent and split-chromophoric protein systems, which are generally described in co-owned, co-pending U.S. patent application Ser. No. 10/973,693 filed Oct. 25, 2004, hereby incorporated by reference in its entirety.

Split-fluorescent protein fragments should be capable of being folded and soluble in the environment of the particular assay in which they are to be employed. In preferred embodiments, the folding/solubility of individual fragments is tested, and typically evolved, in order to isolate a soluble "tag" fragment(s) and a soluble "assay" fragment(s). In preferred solubility assay applications, the tag fragment is between 1 and 3 beta-strands, and in most preferred applications, the tag is a single beta-strand. Test proteins are fused to the tag fragment, which preferably is substantially non-perturbing to fused test proteins. In other words, the solubility and folding of the test protein alone should be similar to the solubility and folding of the test protein when fused with the tag.

Based on experimental results using split-GFP systems (see Example 2), optimum performance in solubility assays are achieved by using a relatively large assay fragment (e.g., about 8 to 10 contiguous beta-strands) and a relatively small tag fragment (e.g., about 1 to 3 contiguous beta-strands) to which the test protein is fused, wherein the assay fragment is soluble and available for complementation to the tag fragment-test protein fusion, and wherein the tag fragment is non-perturbing to test protein solubility. Ideally, for most applications, the solubility of the test protein alone, and the solubility of the test protein in fusion with the tag fragment should be approximately the same. The assay fragment is ideally monomeric, and should not spontaneously aggregate or misfold.

Although in many applications, the use of a non-perturbing tag fragment is preferred, a tag fragment may nevertheless be perturbing to the solubility of the test protein and remain useful in solubility screening assays, provided that there is substantial proportionality between fluorescence and solubility (but not necessarily direct proportionality). In some embodiments, it may in fact be desirable to use a perturbing tag fragment or fragments (see description of Sandwich-Format Assays, infra), such as where the aim is to screen for highly soluble proteins. In this case, the use of a perturbing tag fragment may effectively select against all but the most soluble proteins or versions of a protein. Again, the assay fragment in such applications should be soluble, as insoluble versions will not be available for complementation to soluble test protein-tag fragment fusions.

Protein-Protein Interaction Detection Systems

The protein-protein interaction detection systems of the invention utilize microdomains of a fluorescent protein, such as GFP, to tag two or more interacting proteins or two or more potentially interacting proteins. Generally, the microdomains correspond to one or more contiguous beta-strands of the fluorescent protein structure. Thus, for example, two known interacting proteins, X and Y, may be fused to GFP microdomain tags corresponding to beta-strands 10 and 11, in order to produce a set of tagged polypeptides s10-X and s11-Y, X-s10 and Y-s11, and the like. The fusion polypeptides are typically constructed at the DNA level, and may be co-expressed or separately expressed, as will generally be understood by those in the art. In preferred embodiments, each microdomain tag substantially corresponds to a single beta-strand.

To illustrate the general concept of the invention, the following is a description of a simple two protein interaction detection system which utilizes GFP microdomain tags corresponding to s10 and s11, together with an assay fragment corresponding to GFP s1-9. These "tag" microdomains are selected such that they will not spontaneously self-complement with a complementary assay fragment (GFP s1-9), unless the fused interacting proteins interact. In this simple case, proteins X and Y are known to interact. Proteins X and Y are expressed as fusions with the s10 and s11 tags, respectively, in a cell. The assay fragment is expressed in the cell or is transfected into the cell. The interaction of X and Y brings the tag fragments into proximity, favoring simultaneous interaction with the assay fragment, which results in self-complementation between the three GFP fragments, reconstituting the GFP molecule, which then displays its characteristic fluorescence, which indicates that proteins X and Y interacted in the cell. (FIG. 26).

This simple protein-protein interaction assay may be used to evaluate the interaction of proteins X and Y in particular environments, in different cells, under different physical conditions, and in the presence of other protein factors, agents, drugs, etc. Such an assay is readily adaptable to high-throughput screening endeavors aimed at isolating candidate agents that modulate the interaction between X and Y. For example, the system may be used to screen for agents that interfere with the interaction of proteins X and Y. In one specific in vitro assay embodiment, various test agents may be added to cells expressing the tagged X and Y proteins. The cells may then be lysed and reacted with the assay fragment. Alternatively, the assay fragment can be expressed within the cell or imported using protein transfection reagents well known in the art (Chariot reagent). Where X and Y interact, entropy favors complementation with the assay fragment, and fluorescence is displayed. Agents that interfere with the interaction of X and Y may be identified by reduced fluorescence relative to such baseline fluorescence or by the absence of detectable fluorescence. Such an assay is readily adaptable to high-throughput screens, wherein a multiplicity of wells contain cells engineered to express the tagged proteins and many different test agents may be added to individual wells.

Various embodiments of the protein-protein interaction detection system of the invention are envisioned, several of which are described by way of the examples, infra.

Another aspect of the invention relates to the use of the protein-protein interaction detection system to identify and isolate proteins that interact with other proteins. Various embodiments are envisioned, including without limitation assays that can identify an unknown protein X that interacts with known protein Y, an unknown protein X that interacts with an unknown protein Y, a known protein X that interacts with a known protein Y (wherein the interaction was not known).

Another aspect of the invention utilizes the protein-protein interaction detection system to screen for variants of one of a pair of known interacting proteins having improved or defined characteristics, such as higher affinity binding to the other protein. As an illustration, an antibody X that binds to protein Y may be subjected to a directed evolution strategy aimed at improving binding specificity or affinity. Briefly, single chains of the antibody may be expressed as a library of mutants and evaluated for binding characteristics, for example binding affinity. Thus, a library of mutant proteins X are expressed as GFP microdomain fusions (i.e., X'-s10) and allowed to react with the fusion Y-s11 in the presence of the complementary assay fragment s1-9. Stronger fluorescence relative to what is generated when the wild-type X-s10 is expressed and allowed to react with Y-s11 in the presence of the assay fragment provides an indication that X' has a stronger affinity for Y than X.

In a related embodiment, X'-s10 may be co-expressed with or expressed in the presence of the wild type fusion X-s10, both of which are allowed to compete for interaction with Y-s11 in the presence of the assay fragment GFP s1-9. Color shift mutations may be used to distinguish which of X and X' out competes the other for interaction with Y. For example, in GFP, strand 10 may be mutated at residue T203Y to generate the yellow color shift GFP variant. Thus, for example, protein X may be tagged with GFP s10 T203Y, and mutant proteins X' tagged with the "green" s10 T203. The interacting protein is tagged with s11. The three fragments may, in one embodiment, be co-expressed in the same cell. Whichever of X or X' is more efficient in interacting with Y, it will form part of the complementation complex with the assay fragment, thus determining the color of the reconstituted fluorescent protein. Accordingly, in this illustration, green fluorescence provides an indication that X' out competed X for binding to Y, whereas yellow fluorescence provides an indication that the wild-type X was the better binder. Such competitive binding assays may be productively employed in screening for variants of proteins with higher binding affinities i.e., antibody variants, binders based on ankyrin domain fusions (Binz et. al, 2004 High-affinity binders selected from designed ankyrin repeat protein libraries, Nature Biotechnology 22: 575-582) etc.

Three-Fragment Protein-Protein Interaction Assay Systems

One aspect of the invention relates to protein-protein interaction assay systems utilizing a three-fragment complementation system. Briefly, in a three-fragment system, two interacting proteins are expressed as fusions with each of two GFP fragments, each GFP fragment corresponding to one or more contiguous beta strands (i.e., X-s10 and Y-s11, where X and Y are interacting proteins or potentially interacting proteins). Co-expression of the two fusions in a host cell, in the presence of the added or expressed assay fragment corresponding to the beta-strands of the fluorescent protein not represented in the X-s10 and Y-s11 constructs, provides an opportunity for complementation between the three fragments where X and Y interact. In the absence of interaction of X and Y, the three fragments will not complement. Complementation is visualized by fluorescence. Thus, this system may be used to identify unknown proteins Y that interact with X.

The system may also be used to screen engineered variants of Y having improved affinities for protein X.

The system may also be used to screen for chemical compounds that interfere with the interaction of X and Y.

Conversely, the system may be used to screen for proteins Y that are able to avoid the interfering affect of a chemical compound on the interaction between X and Y.

Reporter fluorescent and chromophoric proteins may be split into three (or more) individual fragments capable of self-complementing to form a reconstituted reporter protein. In one embodiment of a sandwich-format protein detection assay, two tag fragments of the fluorescent or chromophoric protein are fused to a test protein, which fragments, together, are capable of complementing with a third fragment to reconstitute the fluorescent or chromophoric phenotype. For example, a test protein may be inserted between two contiguous beta strands of GFP, i.e., GFP S10-x-GFP S11. Soluble protein detection is accomplished by detectable complementation with GFP 1-9. In this embodiment, complementation of the three fragments identifies the test protein as soluble, and full-length, and indicates that the two fragments of GFP fused to x are functionally linked by x. Particularly in the context of directed evolution strategies, this approach provides the advantage of ensuring that the test protein x is actually full-length and intact (whereas X-GFP S11 would only complement GFP 1-10, not GFP 1-9) guarding against the appearance of truncated versions of the test protein, or versions incorporating internal ribosome binding sites, or proteolyzed versions.

A related, more stringent solubility assay embodiment utilizes two tag fragments fused to a test protein, wherein each of the fragments may be independently detected by functional reconstitution with an independent and distinguishable third complementing assay fragment. More specifically, for example, in a fusion of GFP S10-x-GFP S11, strand 10 would be detectable by circular permutant GFP 11-9 delta 10 (circular permutant 11-1-2-3-4-5-6-7-8-9, where 11 and 1 are linked and 10 is missing, and numbers refer to the strand, see FIG. 3), whereas strand 11 would be detectable by 1-10 delta 11 (1-2-3-4-5-6-7-8-9-10, where 11 is missing). Independent simultaneous detection of the two tags may be facilitated by utilizing color shift variants of GFP in one or both complementing pair(s) (i.e., GFP 11-9 delta 10 could be the cyan variant (Y66W) and GFP 1-10 delta 11 could be the yellow variant (T203Y). Alternatively, the tag fragments could be derived from fluorescent proteins with distinct amino acid sequences, and detected with the appropriate corresponding assay fragment. For example, strand 11 from GFP could be employed to tag the N-terminus of a test protein X and detected with strands 1-10 of GFP, while strand 11 from red fluorescent protein DsRed (Matz et al., 1999, Nat. Biotechnol. 17:969-973) could be simultaneously employed as a fusion to the C-terminus of the same test protein X and detected with strands 1-10 of DsRed.

An alternative embodiment utilizes FRET exhibited between the two reconstituted GFPs linked by the test protein. For example, CFP 11-9 delta 10::10-X-11::YFP 1-10 may be used. Such a construct would be functionally equivalent to CFP-x-YFP, previously shown to exhibit FRET from CFP donor to YFP acceptor as long as x is intact, loosing FRET if x is cleaved, freeing CFP and YFP from proximity, the efficiency of FRET dependent on $(1/r^6)$ where r is the distance between the donor and acceptor.

Applications in Prokaryotic and Eukaryotic Cell Culture

The split-fluorescent and split-chromophoric protein systems of the invention may be applied to assays in virtually any cell type, including without limitation bacterial cells (e.g., *E. coli*) and mammalian cells (e.g., CHO cells). One limitation is that expression of GFP and GFP-like proteins is compromised in highly acidic environments (i.e., pH=4.0 or less). Likewise, complementation rates are generally inefficient under conditions of pH of 6.5 or lower (see Example 8, infra).

As will be appreciated by those skilled in the art, the vectors used to express the tag and/or assay fragments must be compatible with the host cell in which the vectors are to reside. Similarly, various promoter systems are available and should be selected for compatibility with cell type, strain, etc. Codon optimization techniques may be employed to adapt sequences for use in other cells, as is well known.

When using mammalian cells for complementation assays of the invention, an alternative to codon optimization is the use of chemical transfection reagents, such as the recently described "chariot" system (Morris et al., 2001, *A peptide carrier for the delivery of biologically active proteins into mammalian cells*. Nature Biotechnol. 19: 1173-1176). The Chariot™ reagent may be used to directly transfect a protein into the cytoplasm of a mammalian cell. Thus, this approach would be useful for an in vivo protein detection assay, wherein the assay fragment may be introduced into the cell, either before or after expression of the genetically-encoded test protein-tag fragment fusion by the cell.

Methods for Isolating Improved Protein Variants

The protein interaction assays described supra may be used in combination with directed evolution strategies aimed at isolating protein variants having improved characteristics relative to a parent, un-evolved protein.

Any method known in the art for generating a library of mutated protein variants may be used to generate candidate test proteins which may be expressed as fusions with a tag fragment. The target protein or polypeptide is usually mutated by mutating the nucleic acid. Techniques for mutagenizing are well known in the art. These include, but are not limited to, such techniques as error-prone PCR, chemical mutagenesis, and cassette mutagenesis. Alternatively, mutator strains of host cells may be employed to add mutational frequency (Greener and Callahan (1995) *Strategies in Mol. Biol.* 7: 32). For example, error-prone PCR (see, e.g., Ausubel, supra) uses low-fidelity polymerization conditions to introduce a low level of point mutations randomly over a long sequence. Other mutagenesis methods include, for example, recombination (WO98/42727); oligonucleotide-directed mutagenesis (see, e.g., the review in Smith, *Ann. Rev. Genet.* 19: 423-462 (1985); Botstein and Shortle, *Science* 229: 1193-1201 (1985); Carter, *Biochem. J.* 237: 1-7 (1986); Kunkel, "The efficiency of oligonucleotide directed mutagenesis" in Nucleic acids & Molecular Biology, Eckstein and Lilley, eds., Springer Verlag, Berlin (1987), *Methods in Enzymol.* 100: 468-500 (1983), and *Methods in Enzymol.* 154: 329-350 (1987)); phosphothioate-modified DNA mutagenesis (Taylor et al., *Nucl. Acids Res.* 13: 8749-8764 (1985); Taylor et al., *Nucl. Acids Res.* 13: 8765-8787 (1985); Nakamaye and Eckstein, *Nucl. Acids Res.* 14: 9679-9698 (1986); Sayers et al., *Nucl. Acids Res.* 16:791-802 (1988); Sayers et al., *Nucl. Acids Res.* 16: 803-814 (1988)), mutagenesis using uracil-containing templates (Kunkel, *Proc. Nat'l. Acad. Sci. USA* 82: 488-492 (1985) and Kunkel et al., Methods in Enzymol. 154:367-382, 1987); mutagenesis using gapped duplex DNA (Kramer et al., *Nucl. Acids Res.* 12: 9441-9456 (1984); Kramer and Fritz, *Methods in Enzymol.* 154:350-367 (1987); Kramer et al., *Nucl. Acids Res.* 16: 7207 (1988)); and Fritz et al., *Nucl. Acids Res.* 16: 6987-6999 (1988)). Additional methods include point mismatch repair (Kramer et al., *Cell* 38: 879-887 (1984)), mutagenesis using repair-deficient host strains (Carter et al., *Nucl. Acids Res.* 13: 4431-4443 (1985); Carter, *Methods in Enzymol.* 154: 382-403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond. A* 317: 415-423 (1986)), mutagenesis by total gene synthesis (Nambiar et al., *Science* 223: 1299-1301 (1984); Sakamar and Khorana, *Nucl. Acids Res.* 14: 6361-6372 (1988); Wells et al., *Gene* 34:315-323 (1985); and Grundstrom et al., *Nucl. Acids Res.* 13: 3305-3316 (1985). Kits for mutagenesis are commercially available (e.g., Bio-Rad, Amersham International). More recent approaches include codon-based mutagenesis, in which entire codons are replaced, thereby increasing the diversity of mutants generated, as exemplified by the RID method described in Murakami et al., 2002, Nature Biotechnology, 20: 76-81.

In a cell-based expression system, clones expressing variants may be rapidly screened for solubility using the above-described in vivo or in vitro assays. Thus, in an in vivo embodiment, a library of clones is generated in *E. coli*, each clone harboring an expressible construct encoding an individual variant protein fused to the tag fragment, under the control of a first and independently inducible promoter. The cells may concurrently harbor an expressible construct encoding the complementary assay fragment, under the control of a second and separately inducible promoter, or the assay fragment polypeptide itself (introduced by protein transfection methods such as described in Morris et al., 2001, supra)

In one in vivo embodiment, cells are induced to express the tag fragment-protein variant fusion, followed by expression of the complementary fragment in the cells. In most preferred embodiments, expression of the fusion is repressed or shut-down for a time sufficient to permit aggregation of insoluble fusion (i.e., 1 h, see Example 4 and Example 10, infra), followed by the induction of complementary fragment expression. In a variation of this approach, the cells only harbor the fusion constructs, preferably under the control of an inducible/repressible promoter, and the complementary fragment is introduced by protein transfection methodologies.

Various in vitro embodiments are possible. Generally, these comprise the expression of the variant protein-tag fragment fusions in, for example, *E. coli*, followed by cell lysis and reaction with the complementary assay fragment polypeptide.

Precomplementation

The rate of fluorescence formation during complementation of GFP fragments can be vastly increased by using fragments of GFP in which the chromophore has been pre-formed in the fragment bearing the relevant chromophore amino acids, relative to fragments in which the chromophore cyclization has never occurred. Briefly, a non-fluorescent pre-complemented GFP fragment bearing the chromophore amino acids can be formed by: (1) mixing the fragment with the complementary fragment(s) not containing the chromophore amino acids; (2) allowing the complementation reaction and formation of fluorescence to go to completion; (3) unfolding the fragments, for example by chemical means, to generate unfolded non-fluorescent GFP fragments; (4) recovering the fragment containing the chromophore amino acids and separating it from the other fragment(s); (5) renaturing the fragment bearing the chromophore amino acids. This fragment remains substantially non-fluorescent even though it contains the cyclized chromophore because it has been is substantially unfolded by chemical or other means so as to be non-fluorescent, and remains unfolded in the absence of the complementary fragment(s). Rapid restoration of fluorescence can be obtained without having to generate the covalent modifications associated with the chromophore simply by re-adding the complementary, non-chromophore-containing GFP fragment(s). By this approach, because the slow chromophore cyclization reaction is complete, formation of fluorescence during complementation is limited only by the rate of binding of the complementary fragments and formation of the folded beta-barrel native structure.

Split-Protein Fragment Engineering

Directed Evolution Strategy for Isolating Soluble Self-Complementing Fragments

Another aspect of the invention relates to methods for generating ideal split protein interactors by directed evolution and sequential induction of fragments. The incorporation of sequential induction contrasts with the existing published approaches specifying co-induction of split fragments. Briefly, in the sequential induction approach, fragment 1 is held constant and fragment 2 is evolved. When fragment 1 is held constant and fragment 2 is evolved, fragment 2 is first expressed, then expression is shut off. The fragment is allowed to aggregate or remain soluble. Next, fragment 1 is expressed. If both fragments are expressed simultaneously, this can lead to false positives because complementation can occur prior to aggregation. Sequential expression leads to the selection of true positives, i.e., soluble variants. Following the selection of an optimum fragment 2 variant, this variant is then held constant and fragment 1 is then evolved. The process may be continued using further sequential inductions until the desired fragment solubilities are attained. Using this approach, the resulting fragments can be engineered to be soluble on their own prior to complementation.

Attenuating Solubility Perturbation of Detectable Proteins

Soluble fragments may be further engineered to reduce their perturbing effect on the solubility of fused passenger domains (test proteins). Briefly, a test protein which is less soluble when fused to the fragment than when expressed alone is used as a 'bait' domain in a directed evolution approach aimed at engineering the fragment such that the fusion and non-fusion solubilities are similar thereby reducing the effect of the fragment on the solubility of the test protein. This strategy was employed in optimizing a small fragment of GFP, resulting in a variant with attenuated perturbing effect on fused passenger proteins (see, Example 4, infra). The approach can be applied to one or more fragments of GFP, simultaneously or in succession, using suitable bait proteins for which the solubility of the fusion is lower than the bait protein expressed alone.

Kits

Another aspect of the invention provides split-fluorescent and split-chromophoric protein system kits useful in conducting the various assays described, supra. Kits of the invention may facilitate the use of split-fluorescent and split-chromophoric systems of the invention. Various materials and reagents for practicing the assays of the invention may be provided. Kits may contain reagents including, without limitation, polypeptides or polynucleotides, cell transformation and transfection reagents, reagents and materials for purifying polypeptides, protein denaturing and refolding reagents, as well as other solutions or buffers useful in carrying out the assays and other methods of the invention. Kits may also include control samples, materials useful in calibrating the assays of the invention, and containers, tubes, microtiter plates and the like in which assay reactions may be conducted. Kits may be packaged in containers, which may comprise compartments for receiving the contents of the kits, instructions for conducting the assays, etc.

For example, kits may provide one or more split-fluorescent protein fragments of the invention, one or more polynucleotide vectors encoding one or more fluorescent protein fragments, bacterial cell strains suitable for propagating the vector, cells pretransformed or stably transfected with constructs encoding one or more fluorescent protein fragments, and reagents for purification of expressed fusion proteins.

In one embodiment of a kit which facilitates conducting the protein detection assays of the invention, the kit contains a recipient nucleic acid vector containing the coding sequence of a tag fluorescent or chromophoric protein fragment (i.e., GFP S11 and GFP S10), which includes a multiple cloning site for inserting test protein in-frame at the N-terminus of the tag fragment coding sequences. Optionally, the insertion site may be followed by the coding sequence of a linker polypeptide in frame with the coding sequence of the downstream tag sequence. A specific embodiment is the pTET-SpecR plasmid, the engineering of which is described in Example 1 and which is illustrated in FIG. 1. The complete nucleotide sequence of the pTET-SpecR plasmid is shown in FIG. 1B. The X-s10 and Y-S11 can be separately expressed, or both expressed from a single polycistron.

These recipients, or "tag vectors" are used to produce test protein-tag fusions in suitable host cells. In an in vitro assay embodiment, the kit further contains a pre-purified assay fragment (i.e., GFP 1-9 polypeptide) used to detect interactions of the test protein-tag fragment fusions expressed by the tag vector(s). In an in vivo assay embodiment, the kit further contains an "assay vector" which is compatible with the tag vector(s) and encodes the assay fragment under the control of an independently regulated promoter. In an alternate in vivo assay embodiment, cells containing an assay vector (i.e., vector encoding GFP 1-9 under the control of an inducible promoter) are provided in the kit, along with a compatible tag vector into which test proteins may be cloned, wherein expression in controlled by a separately inducible promoter. The cells containing the assay vector may be transformed with the tag vector, and cell fluorescence monitored.

Materials for calibrating the assays of the invention may be provided. In one embodiment, the kit contains a purified interacting coiled-coils fused to GFP S10 and GFP S11 as fusion protein reagents. In another kit, GFP S10 and GFP S11 are fused to FKB12 and FRB, two proteins whose interaction can be induced by the addition of rapamycin, as in Mootz & Muir, 2002, *Protein splicing triggered by a small molecule* J. Am. Chem. Soc. 124: 9044-9045, Standaert et al. 1990, Molecular cloning and overexpression of the human FK506-binding protein FKBP, Nature 346: 671-674; Chen et al., 1995, Identification of an 11-kDa FKBP12-rapamycin-binding domain within the 289-kDa FKBP12-rapamycin-associated protein and characterization of a critical serine residue, Biochemistry 92: 4947-4951.

Fluorescent and Chromophoric Proteins

The invention provides methods and principles for the design of split-fluorescent and split-chromophoric protein systems, and is herein exemplified by the generation and molecular evolution of optimal split-GFP systems for use in protein interaction detection and protein interaction quantification. However, other GFP-like proteins may be used in the practice of the invention.

One group of fluorescent proteins includes the Green Fluorescent Protein isolated from Aequorea Victoria (GFP), as well as a number of GFP variants, such as cyan fluorescent protein, blue fluorescent protein, yellow fluorescent protein, etc. (Zimmer, 2002, Chem. Rev. 102: 759-781; Zhang et al., 2002, Nature Reviews 3: 906-918). Typically, these variants share about 80%, or greater sequence identity with SEQ ID NO:2 (or SEQ ID NO:8.) These color-shift GFP mutants have emission colors blue to yellow-green, increased brightness, and photostability (Tsien, 1998, Annual Review of Biochemistry 67: 509-544). One such GFP mutant, termed the Enhanced Yellow Fluorescent Protein, displays an emission maximum at 529 nm. Another recently described mutant, a gold variant, was generated by incorporating a non-natural variant of tryptophan into the cyan variant, and is characterized by a significantly red-shifted emission maximum of 574 nm (Bae et al., 2003, J. Mol. Biol. 328: 1071-1081).

Additional GFP-based variants having modified excitation and emission spectra (Tsien et al., U.S. Patent Appn. 20020123113A1), enhanced fluorescence intensity and thermal tolerance (Thastrup et al., U.S. Patent Appn. 20020107362A1; Bjorn et al., U.S. Patent Appn. 20020177189A1), and chromophore formation under reduced oxygen levels (Fisher, U.S. Pat. No. 6,414,119) have also been described. GFPs from the Anthozoans *Renilla reniformis* and *Renilla kollikeri* have also been described (Ward et al., U.S. Patent Appn. 20030013849).

Additionally, over 100 GFP-like fluorescent proteins and non-fluorescent chromoproteins from the class Anthozoa have now been identified (for review, see Verkusha et al., 2003, *GFP-like fluorescent proteins and chromoproteins of the class Anthozoa*, In: Protein Structures: Kaleidoscope of Structural Properties and Functions, pp. 405-439, Ed. V. Uversky. Research Signpost Press, Kereala, India). This group of Anthozoa proteins includes the red fluorescent protein isolated from *Discosoma* species of coral, DsRed (Matz et al., 1999, Nat. Biotechnol. 17:969-973), and various DsRed variants (e.g., DsRed1, DsRed2). DsRed and the other Anthozoa fluorescent proteins share only about 26-30% amino acid sequence identity to the wild-type GFP from *Aequorea victoria*, yet all the crucial motifs are conserved, indicating the formation of the 11-stranded beta-barrel structure characteristic of GFP. The crystal structure of DsRed has also been solved, and shows conservation of the 11-stranded beta-barrel structure of GFP MMDB Id: 5742.

A number of mutants of the longer wavelength red fluorescent protein DsRed have also been described. For example, recently described DsRed mutants with emission spectra shifted further to the red may be employed in the practice of the invention (Wiehler et al., 2001, FEBS Letters 487: 384-389; Terskikh et al., 2000, Science 290: 1585-1588; Baird et al., 2000, Proc. Natl. Acad. Sci. USA 97: 11984-11989). Recently, a monomeric variant of DsRed was described (Campell et al., 2002, Proc. Natl. Acad. Sci USA 99: 7877-7882). This variant, termed "mRFP1", matures quickly (in comparison to wild type DsRed, which matures over a period of 30 hours), has no residual green fluorescence, and has excitation and emission wavelengths of about 25 nm longer than other DsRed variants.

An increasingly large number of other fluorescent proteins from a number of ocean life forms have recently been described, and the Protein Data Bank currently lists a number of GFP and GFP mutant crystal structures, as well as the crystal structures of various GFP analogs. Related fluorescent proteins with structures inferred to be similar to GFP from corals, sea pens, sea squirts, and sea anemones have been described, and may be used in the generation of the split-fluorescent protein systems of the invention (for reviews, see Zimmer, 2002, Chem. Rev. 102: 759-781; Zhang et al., 2002, Nature Reviews 3: 906-918).

Additionally, fluorescent proteins from *Anemonia majano, Zoanthus* sp., *Discosoma striata, Discosoma* sp. and *Clavularia* sp. have also been reported (Matz et al., supra). A fluorescent protein cloned from the stony coral species, *Trachyphyllia geoffroyi*, has been reported to emit green, yellow, and red light, and to convert from green light to red light emission upon exposure to UV light (Ando et al., 2002, Proc. Natl. Acad. Sci. USA 99: 12651-12656). Recently described fluorescent proteins from sea anemones include green and orange fluorescent proteins cloned from *Anemonia sulcata* (Wiedenmann et al., 2000, Proc. Natl. Acad. Sci. USA 97: 14091-14096), a naturally enhanced green fluorescent protein cloned from the tentacles of *Heteractis magnifica* (Hongbin et al., 2003, Biochem. Biophys. Res. Commun. 301: 879-885), and a generally non fluorescent purple chromoprotein displaying weak red fluorescence cloned from *Anemonia sulcata*, and a mutant thereof displaying far-red shift emission spectra (595 nm) (Lukyanov et al., 2000, J. Biol. Chem. 275: 25879-25882).

A recently described red fluorescent protein isolated from the sea anenome *Entacmaea quadricolor*, EqFP611, is a far-red, highly fluorescent protein with a unique co-planar and trans chromophore (Wiedenmann et al., 2002, Proc. Natl. Acad. Sci USA 99: 11646-11651). The crystal structure of EqFP611 has been solved, and shows conservation of the 11-stranded beta-barrel structure of GFP MMDB Id: 5742 (Petersen et al., 2003, J. Biol. Chem, Aug. 8, 2003; M307896200).

Still further classes of GFP-like proteins having chromophoric and fluorescent properties have been described. One such group of coral-derived proteins, the pocilloporins, exhibit a broad range of spectral and fluorescent characteristics (Dove and Hoegh-Guldberg, 1999, PCT application WO 00/46233; Dove et al., 2001, Coral Reefs 19: 197-204). Recently, the purification and crystallization of the pocilloporin Rtms5 from the reef-building coral *Montipora efflorescens* has been described (Beddoe et al., 2003, Acta Cryst. D59: 597-599). Rtms5 is deep blue in color, yet is weakly fluorescent. However, it has been reported that Rtms5, as well as other chromoproteins with sequence homology to Rtms5, can be interconverted to a far-red fluorescent protein via single amino acid substitutions (Beddoe et al., 2003, supra; Bulina et al., 2002, BMC Biochem. 3: 7; Lukyanov et al., 2000, supra).

Various other coral-derived chromoproteins closely related to the pocilloporins are also known (see, for example, Lukyanov et al. 2000, J. Biol. Chem. 275: 25879-82; Gurskaya et al., 2001, FEBS Letters 507: 16-20). To the extent that these chromoproteins contain the conserved 11-stranded beta barrel structure of GFP and other fluorescent proteins, they may be split into self-complementing fragments and used in the assay systems as described herein.

Any fluorescent protein that has a structure with a root mean square deviation of less than 5 angstroms, often less than 3, or 4 angstroms, and preferably less than 2 angstroms from the 11-stranded beta-barrel structure of MMDB Id:5742 may be used in the development of self-complementing fragments. In some cases, fluorescent proteins exist in multimeric form. For example, DsRed is tetrameric (Cotlet et al., 2001, Proc. Natl. Acad. Sci. USA 98: 14398014403). As will be appreciated by those skilled in the art, structural deviation between such multimeric fluorescent proteins and GFP (a monomer) is evaluated on the basis of the monomeric unit of the structure of the fluorescent protein.

As appreciated by one of ordinary skill in the art, such a suitable fluorescent protein or chromoprotein structure can be identified using comparison methodology well known in the art. In identifying the protein, a crucial feature in the alignment and comparison to the MMDB ID:5742 structure is the conservation of the beta-barrel structure (i.e., typically comprising 11 beta strands, but in at least one case, fewer beta strands (see, Wiedenmann et al., 2000, supra), and the topology or connection order of the secondary structural elements (see, e.g., Ormo et al. "Crystal structure of the *Aequorea victoria* green fluorescent protein."Yang et al, 1996, Science 273: 5280, 1392-5; Yang et al., 1996 Nat Biotechnol. 10:1246-51). Typically, most of the deviations between a fluorescent protein and the GFP structure are in the length(s) of the connecting strands or linkers between the crucial beta strands (see, for example, the comparison of DsRed and GFP in Yarbrough et al., 2001, Proc Natl Acad Sci USA 98:462-7). In Yarbrough et al., alignment of GFP and DsRed is shown pictorially. From the stereo diagram, it is apparent that the 11 beta-strand barrel is rigorously conserved between the two structures. The c-alpha backbones are aligned to within 1 angstrom RMSD over 169 amino acids, although the sequence identity is only 23% comparing DsRed and GFP.

In comparing structure, the two structures to be compared are aligned using algorithms familiar to those in the art, using for example the CCP4 program suite. COLLABORATIVE COMPUTATIONAL PROJECT, NUMBER 4. 1994. "The CCP4 Suite: Programs for Protein Crystallography". Acta Cryst. D50, 760-763. In using such a program, the user inputs the PDB coordinate files of the two structures to be aligned, and the program generates output coordinates of the atoms of the aligned structures using a rigid body transformation (rotation and translation) to minimize the global differences in position of the atoms in the two structures. The output aligned coordinates for each structure can be visualized separately or as a superposition by readily-available molecular graphics programs such as RASMOL, Sayle and Milner-White, September 1995, Trends in Biochemical Science (TIBS), Vol. 20, No. 9, p. 374), or Swiss PDB Viewer, Guex, N and Peitsch, M. C., 1996 Swiss-PdbViewer: A Fast and Easy-to-use PDB Viewer for Macintosh and PC. Protein Data Bank Quarterly Newsletter 77, pp. 7.

In considering the RMSD, the RMSD value scales with the extent of the structural alignments and this size is taken into consideration when using the RMSD as a descriptor of overall structural similarity. The issue of scaling of RMSD is typically dealt with by including blocks of amino acids that are aligned within a certain threshold. The longer the unbroken block of aligned sequence that satisfies a specified criterion, the 'better' aligned the structures are. In the DsRed example, 164 of the c-alpha carbons can be aligned to within 1 angstrom of the GFP. Typically, users skilled in the art will select a program that can align the two trial structures based on rigid body transformations, for example, as described in Dali et al., Journal of Molecular Biology 1993, 233, 123-138. The output of the DALI algorithm are blocks of sequence that can be superimposed between two structures using rigid body transformations. Regions with Z-scores at or above a threshold of Z=2 are reported as similar. For each such block, the overall RMSD is reported.

The RMSD of a fluorescent protein or chromoprotein for use in the invention is within angstroms for at least 80% of the sequence within the 11 beta strands. Preferably, RMSD is within 2 angstroms for at least 90% of the sequence within the 11 beta strands (the beta strands determined by visual inspection of the two aligned structures graphically drawn as superpositions, and comparison with the aligned blocks reported by DALI program output). As appreciated by one of skill in the art, the linkers between the beta strands can vary considerably, and need not be superimposable between structures.

In preferred embodiments, the fluorescent protein or chromoprotein is a mutated version of the protein or a variant of the protein that has improved folding properties or solubility in comparison to the protein. Often, such proteins can be identified, for example, using methods described in WO0123602 and other methods to select for increased folding.

For example, to obtain a fluorescent protein with increased folding properties, a "bait" or "guest" peptide that decreases the folding yield of the fluorescent protein is linked to the fluorescent protein. The guest peptide can be any peptide that, when inserted, decreases the folding yield of the fluorescent protein. A library of mutated fluorescent proteins is created. The bait peptide is inserted into the fluorescent protein and the degree of fluorescence of the protein is assayed. Those clones exhibit increased fluorescence relative to a fusion protein comprising the bait peptide and parent fluorescent protein are selected (the fluorescent intensity reflects the amount of properly folded fluorescent protein). The guest peptide may be linked to the fluorescent protein at an end, or may be inserted at an internal site.

In a particular embodiment, wild-type and mutant fluorescent proteins and chromoproteins useful in the practice of the invention may be experimentally "evolved" to produce extremely stable, "superfolding" variants. The methods described in co-pending, co-owned U.S. patent application Ser. No. 10/423,688, filed Apr. 24, 2003, hereby incorporated by reference in its entirety, may be employed for the directed evolution of GFP, DsRed, and any number of related fluorescent proteins and chromoproteins. Such superfolding variants may be split into self-complementing fragments, which fragments may be further evolved to modulate solubility characteristics of the fragments alone or when fused to test protein.

Particular methods for the evolution of soluble and non-perturbing (to test protein solubility) variants of split-fluorescent or chromophoric protein fragments are provided under the subheading SPLIT-PROTEIN FRAGMENT ENGINEERING, supra.

EXAMPLES

Various aspects of the invention are further described and illustrated by way of the several examples which follow, none of which are intended to limit the scope of the invention.

Example 1

Constructing Plasmid pTET-SpecR

The commercial tet-promoter PRO Bacterial expression system (Clontech, Palo Alto, Calif.) has the regulatory protein tetR on a second plasmid separate from the expression plasmid, making the creation of large libraries inefficient. To overcome this limitation, we combined the tet promoter which controls the expression of target proteins, and regulatory protein tetR, on a single plasmid containing the tetracycline-inducible promoter tet, the tet promoter regulatory protein tetR, and the selectable antibiotic marker SpecR, which confers resistance to the antibiotic spectinomycin. The ColE1 origin of replication allows this plasmid to co-exist in cells carrying plasmids with a compatible origin such as the p15 origin. This allows one protein, such as a protein tagged with a fragment of GFP, to be expressed from the PTET plasmid, and another protein, such as the complementary GFP assay fragment, to be expressed from a second plasmid, such as a pET vector (Novagen, Madison, Wis.). The pTET-SpecR plasmid is pictured in FIG. 1A, and the sequences of the plasmid and the genetic elements are shown in FIG. 1B.

The pTET-SpecR plasmid was engineered by overlap PCR, combining elements from the commercial pPROTet.6×HN vector, PPROLAR vector, and the autonomously-replicating plasmid carried by the BL21-PRO strain (Clontech, Palo Alto, Calif.). The chloramphenicol resistance gene was replaced by the spectinomycin resistance marker cloned from the autonomously-replicating plasmid carried by the BL21-PRO strain, and placed under the control of the promoter of the kanamycin resistance marker of the PPROLAR vector. We cloned the tetracycline repressor (tetR) protein from the spectinomycin-resistant, autonomously-replicating plasmid isolated from BL21-PRO strain, upstream of the T0 transcription termination sequence. The amount of translated tetR is regulated by a weak Shine-Delgarno sequence downstream of SacI, engineered by selecting a variant of the Shine-Delgarno from a small degeneracy library to minimize leakage and maximize induction after addition of anhydrotetracycline (see infra). The SpeI restriction site present in the commercial version was silenced. The new plasmid "pTET-SpecR" was digested with NcoI and XbaI restriction endonucleases (New England Biolabs, Beverly, Mass.) to receive the GFP S11 split GFP cloning cassette. The structure of the resulting cloning site is Nco-1::6HIS::thrombin cleavage site::Nde-1::frame shift stuffer::BamHI:(GGGS):SpeI::GFP S11 (TAA Stop):: KpnI. Sense strand of cloning cassette flanked by NcoI and KpnI:

[SEQ ID NO:45]

NcoI
<u>CCATGGG</u>CAGCAGCCATCATCATCATCATCACAGCAGCGGCCTGGTGCCG

NdeI              BamHI     SpeI
CGCGGCAGC<u>CATATG</u>GGTGGCGGTTCT<u>GGATCC</u>GGAGGC<u>ACTAGT</u>GGTGG

KpnI
CGGCTCA<u>GGTACC</u>

A frame shift stuffer is preferably added between NdeI and BamHI restriction sites, to avoid background expression due to religated vector.

Example 1 of frame-shift stuffer: FS0

Sequence CATATGTGTTAACTGAGTAGGATCCG [SEQ ID NO: 46]

Example 2 of frame-shift stuffer: FS1

Sequence: CATATGTAATTAATTAATTGGATCCG [SEQ ID NO: 47]

The C-terminal split protein fragment, such as GFP strand 11 or GFP strands 10-11, is cloned between restriction sites SpeI and KpnI using specific oligonucleotide primers to provide the flanking restriction sites and the coding sequence for the desired fragment. The fragment can also be amplified from a template DNA source and the restriction sites incorporated using specific oligonucleotide primers and PCR, methods well-known in the art. It is clear to one with skill in the art that the completed NcoI/KpnI cassette can be transferred to other expression vectors or systems such as the pET vector by engineering the appropriate restriction sites into the destination vector, and other restriction sites can be employed.

The tetR gene was amplified using the plasmid isolated from BL21 (DE3) PRO cells (Clontech, Palo Alto, Calif.). Amplification of the entire gene was realized by using 5' and 3' specific primers of the tetR gene sequence. The sense primer contained a SacI restriction site followed by a Shine-Delgarno sequence optimized for optimal repression/induction of recombinant protein under the control of the tet promoter (see this example, infra). The downstream primer contained a region homologous to the T0 transcription terminator sequence of the PROTet plasmid. The resulting PCR product was assembled with the T0 terminator amplicon and the final product was cloned via the SacI/SpeI restriction sites of the PROTet™ 6×HN vector (Clontech, Palo Alto, Calif.), previously modified by silencing common restriction sites by PCR-mediated site-directed mutagenesis by methods well known in the art. The spectinomycin resistance gene was amplified from the plasmid isolated from BL21 DE3 PRO using gene-specific primers:

P1: CAGGATGAGGATCGTTTCGCATGGTAACGGCGC AGTGGCG, [SEQ ID NO: 48]

P2: CGCCACTGCGCCGTTACCATGCGAAACGATCCT CATCCTG, [SEQ ID NO: 49]

P3: GCATTATTTGCCGACTACCTTGGTGATCTCGCC, [SEQ ID NO: 50]

P4: ACCCCAGAGTCCCGCATTATTTGCCGACTACCTT, [SEQ ID NO: 51]

P1 and P2 primers included the sequence of the kanamycin promoter from the pPROLar vector (Clontech, Palo Alto, Calif.) and P3 and P4 primers included the junction between the end of kanamycin site and SacI. The complete cassette was moved to the new pTET-SpecR plasmid via AatII/SacI restriction sites. The stuffers v1:

CATATGGGTGGCGGTTCTGGATCCGGAGGCACTAG TGGTGGCGGCTCAGGTACCTAACTCGAG [SEQ ID NO: 52]

and v2:

CATATGGGTGGCACTAGTGGTGGCGGCTCAGGTAC CTAACTCGAG [SEQ ID NO: 53]

were engineered from overlapping primers and cloned into the pTET-SpecR plasmid via NcoI and XbaI, to yield pTET-SpecR v1 and v2 plasmids. The Shine-Delgarno sequence that controls the translation of the tetR protein was optimized by mutagenesis and selection. Briefly, the folding reporter GFP gene was cloned into NdeI-BamHI of the stuffer v1 pTET-SpecR plasmid transformed into a DH10B strain. The tetR gene was amplified using degenerate primers for four nucleotides of the Shine-Delgarno sequence and the cassette was cloned SacI/SpeI into the GFP containing pTET-SpecR receiving vector. The resulting library was transformed into a BL21 DE3 strain. Optimal variants were screened by calculating the induction ratio (GFP fluorescence of cells after induction divided by GFP fluorescence of cells before induction) and selecting the variants with the maximal induction ratio upon addition of 0.25 µg/ml anhydrotetracycline (AnTET) (Table 1). The Shine-Delgarno sequence for the optimal tetR sequence showing the largest induction ratio is: AATAAACATTAATG [SEQ ID NO: 54].

TABLE 1

Whole cell fluorescence of GFP expressed in optimum pTET-SpecR vector and in PROTet $Cm^R$ commercial vector.

| | Whole-cell fluorescence | |
|---|---|---|
| | [a]Pre-induction | [b]Post-induction |
| GFP-pTET-Spec[R]::GFP | 28 | 1540 |
| GFP-PROTet-Cm[R]::GFP (Clontech) | 10 | 1930 |

[a]Fluorescence before induction.

[b]Fluorescence after 3 h induction at 37° C. at 250 ng/ml anhydrotetracycline.

Example 2

Finding Feasible Pairs of Split GFP

Figure 2:
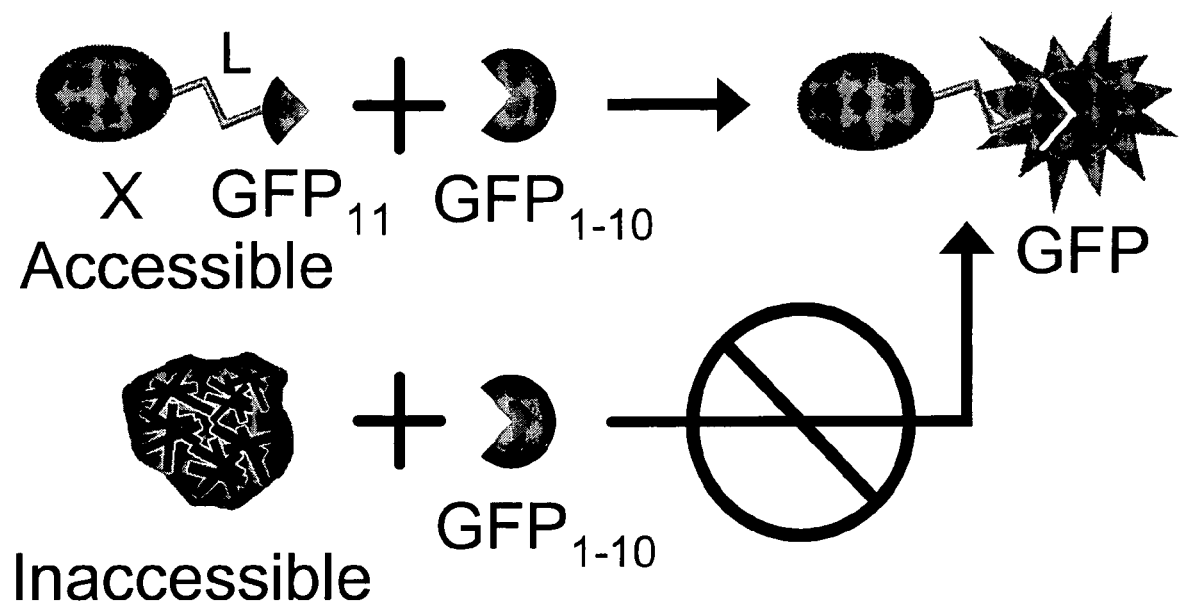
FIG. 2 shows principle of split GFP complementation. A protein of interest (X) is fused to a small GFP fragment (β-strand 11, residues 215-230) via a flexible linker (L). The complementary GFP fragment (β-strands 1-10, residues 1-214) is expressed separately. Neither fragment alone is fluorescent. When mixed, the small and large GFP fragments spontaneously associate, resulting in GFP folding and formation of the fluorophore. Processes that make the small GFP tag inaccessible, such as misfolding or aggregation, can prevent complementation.

To achieve the split GFP protein tagging and detection scheme outlined in FIG. 2, we first tested several pairs of fragments from either folding reporter GFP, which bears the mutations F99S, M153T, V163A (Crameri, Whitehorn et al. 1996), F64L, and S65T (Patterson, Knobel et al. 1997), or the exceptionally stable "superfolder" GFP, containing the folding reporter GFP mutations and S30R, Y39N, N105T, Y145F, I171V, and A206V. We separately co-expressed several pairs of GFP fragments on compatible plasmids in E. coli, including amino acids 1-145+145-238, 1-155+156-238, 1-171+171-238, 1-195+196-238, 1-214+214-238. The junction points corresponded to loops or turns between β-strands (Tsien 1998; Baird, Zacharias et al. 1999) (see FIG. 3). Fragment pairs from superfolder GFP consistently gave much brighter colonies than the same pairs from folding reporter GFP. For example, superfolder GFP fragments from split at 156 and 172 were brighter than fragments derived from folding reporter GFP (see FIG. 4). Our objective was to minimize the size of one of the fragments for use as a protein tag, so we focused on the feasible pair with the smallest fragment (1-214+214-238). To further reduce the size of the tagging domain, we also tested 1-214 (GFP 1-10) for complementation with 214-230 (GFP S11), eliminating the disordered residues 231-238 (Tsien 1998) from the small fragment. Table 2 shows the sequences of the GFP S11 constructs including the wild type and engineered mutants.

TABLE 2

Sequences of GFP S11 variants.

| Fragment | [a,b] Amino acid sequence | | | |
|---|---|---|---|---|
| | 215 | 220 | 225 | 230 |
| GFP S11 wild type [SEQ ID NO: 10] | [c]KRDHMVLLEFVTAAGITGT | | | |
| GFP S11 M1 (L221H) [SEQ ID NO: 12] | [c]KRDHMVLHEFVTAAGITGT | | | |
| [d]GFP S11 M2 (L221H, F223S, T225N) [SEQ ID NO: 14] | [c]KRDHMVLHESVNAAGGT | | | |
| GFP S11 M3 (L221H, F223Y, T225N) [SEQ ID NO: 16] | [e]RDHMVLHEYVNAAGIT | | | |

[a]Point mutations found by directed evolution in bold. Unless otherwise noted, sequences stop at amino acid 230 in GFP, additional C-terminal GT amino acid motif coded by KpnI site.
[b]Numbering corresponds to position in full-length GFP.
[c]C-terminal GT amino acid motif comes from KpnI site, followed by TAA stop codon.
[d]Sequence stops at amino acid 228 in GFP, followed by GT from KpnI site.
[e]Sequence starts at amino acid 215 in GFP sequence. Stop codon after amino acid 230.

Figure 5:
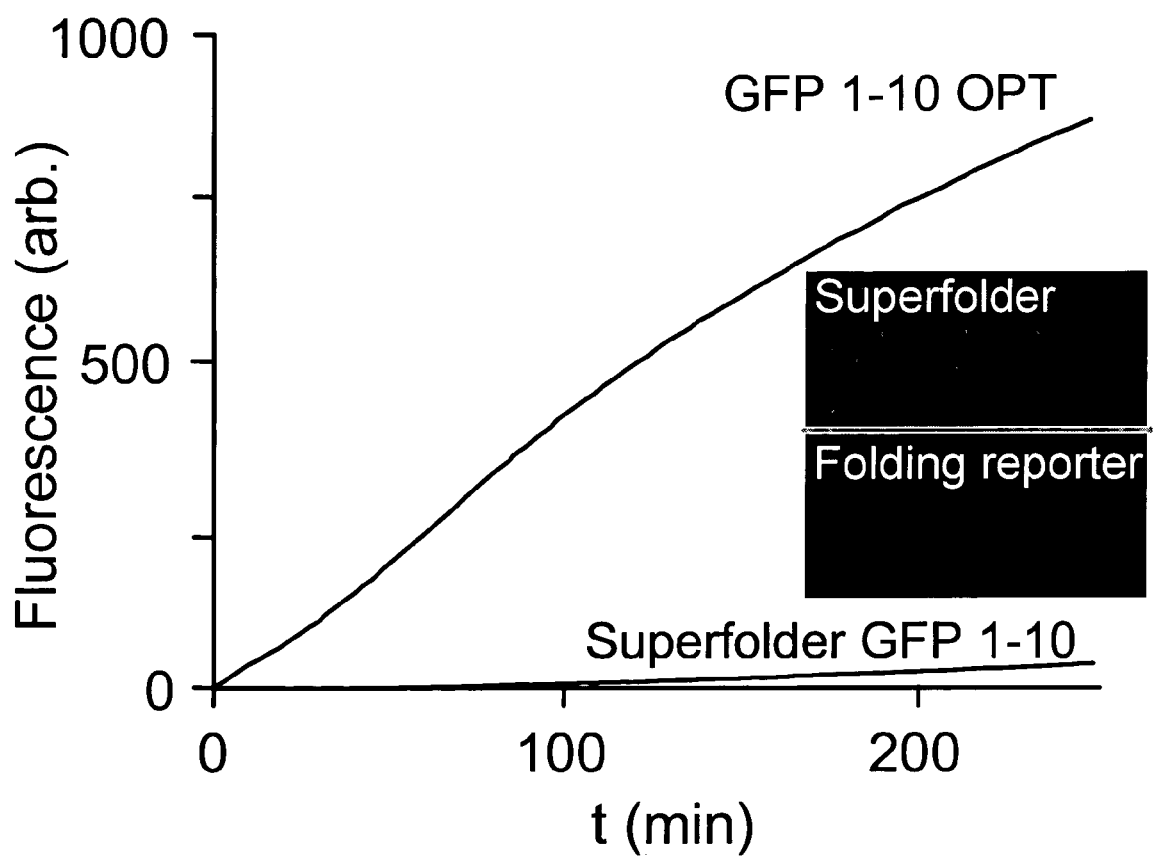
FIG. 5 shows in vitro complementation efficiency of GFP 1-10 variants. Fluorescence progress curves for complementation of 20 µl of 1 mg/ml refolded superfolder GFP 1-10 (lower trace) or an equal amount of soluble optimized GFP 1-10 OPT fragment (upper trace) after addition of 180 µl buffer containing 1 mg/ml soluble sulfite reductase fused to wild type GFP 11. Inset shows in vivo complementation of GFP 1-10 variants. Fluorescent images of *E. coli* BL21(DE3) colonies on nitrocellulose membranes co-expressing GFP 1-10 from superfolder GFP (top), or folding reporter GFP (bottom), along with sulfite reductase fused with wild type GFP S11.

Co-expression of the superfolder GFP fragments 1-214 (GFP 1-10) and 214-230 (GFP S11 wild type) from pET vectors with compatible origins (Novagen, Madison, Wis.) gave fluorescent *Escherichia coli* (*E. coli*) colonies (FIG. 5, inset). No detectable complementation occurred with the corresponding folding reporter GFP fragments (FIG. 5, inset). Superfolder GFP 1-10 was insoluble, but incubation of refolded inclusion bodies (see EXAMPLE 9, infra) with soluble sulfite reductase from *Pyrobaculum aerophilum* (Fitz-Gibbon, Choi et al. 1997) C-terminally tagged with wild type GFP S11 wild type to yield the fusion protein sulfite reductase-GFP S11 wild type, gave a time-dependent increase in fluorescence (FIG. 5, graph).

Example 3

Engineering the GFP Assay Fragment GFP 1-10

We evolved superfolder GFP 1-10 by DNA shuffling (Stemmer 1994) to improve its solubility and increase its complementation with sulfite reductase-GFP 11. Superfolder GFP 1-10 PCR amplicons were subjected to DNA fragmentation and shuffling using published protocols (Stemmer 1994). The GFP 1-10 cDNA library plasmid was transformed into an *E. coli* BL21 (DE3) PRO expression strain (Clontech, Palo Alto, Calif.) containing the sulfite reductase-GFP S11 wild type tagged protein on a PPROTET vector (Clontech, Palo Alto, Calif.). The expression library was plated on nitrocellulose membrane using two successive 400-fold dilutions of a 1.0 $OD_{600\ nm}$ frozen 20% glycerol/Luria-Bertani (LB) stock. After overnight growth at 37° C., the membrane was transferred to an LB/Agar plate containing 50 µg kanamycin, 35 µg chloramphenicol, and 50 µg spectinomycin per ml of media, plus 1 mM IPTG for 3 h at 37° C., and then moved onto a new plate containing the above antibiotics plus 600 ng/ml anhydrotetracycline (AnTET). Clones exhibiting the most rapid development of fluorescence were picked and frozen as −80° C. 20% glycerol freezer stocks. The clones were grown and induced with 1 mM isopropylthiogalactoside (IPTG), and the soluble lysates were screened for complementation efficiency in an in vitro assay (see infra, EXAMPLE 9) with an excess of purified sulfite reductase-GFP S11 wild type fusion protein. The best candidates were pooled and subjected to another round of evolution. Mutations were confirmed by fluorescent dye terminator DNA sequencing. After three rounds of shuffling and selection of the brightest clones, in vitro complementation of the soluble lysate of the best variant, termed GFP 1-10 OPT, improved 80-fold (FIG. 5, graph) relative to the same amount of refolded superfolder GFP 1-10. In addition to the folding reporter GFP mutations (see supra), GFP 1-10 OPT contains S30R, Y145F, I171V, A206V from superfolder GFP, and seven new mutations N39I, T105K, E111V, I128T, K166T, I167V, S205T, and is ca. 50% soluble expressed in *E. coli* at 37° C. Ultraviolet-visible spectra of 10 mg/ml solutions of the non-fluorescent GFP 1-10 OPT lacked the 480 nm absorption band of the red-shifted GFP (Tsien 1998) suggesting that the addition of GFP 11 triggers a folding step required to generate the cyclized chromophore (Tsien 1998). Purified GFP 1-10 OPT, superfolder GFP, and folding reporter GFP were each studied by analytical gel filtration loaded at 10 mg/ml. GFP 1-10 OPT eluted as 60% dimer, 35% monomer, and 5% higher-order aggregates, while full-length folding reporter GFP and superfolder GFP both eluted as >95% monomer, with a trace of dimer and higher-order aggregates.

Example 4

Engineering GFP S11

Figure 6:
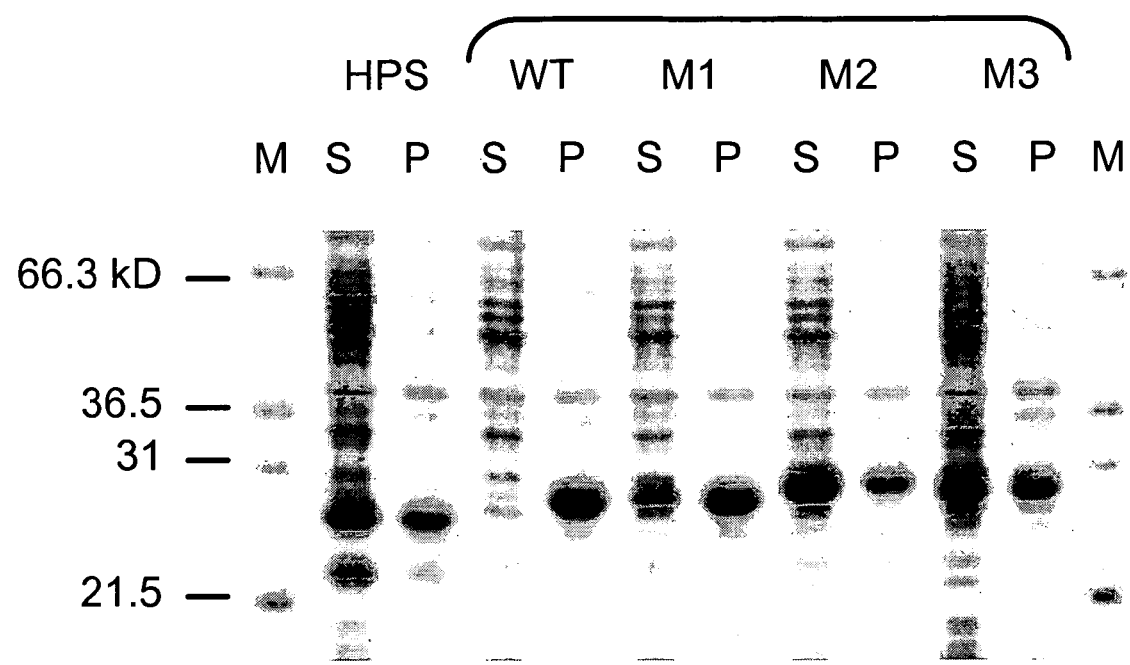
FIG. 6 shows SDS-PAGE gel of soluble (S) and pellet fractions (P) of *E. coli* BL21 (DE3) cells expressing the protein hexulose phosphate synthase (HPS) alone or as N-terminal fusions to GFP S11 wild type (WT), or HPS fused to the three GFP S11 optima (M1, M2, M3). Note that the HPS-GFP S11 wild type fusion is insoluble, while HPS alone is ca. 60% soluble.

The C-terminal wild type GFP S11 fusion tag dramatically reduced the solubility of several *Pyrobaculum aerophilum* (Fitz-Gibbon, Choi et al. 1997) test proteins (Table 3). 3-hexulose 6-phosphate synthase (HPS) alone was 60% soluble, but insoluble when fused to wild type GFP 11 (FIG. 6, Table 3). Protein solubility was determined by SDS-PAGE and gel densitometry analysis as previously described (Waldo, Standish et al. 1999; Waldo 2003). Briefly, for high-throughput screens, 1 ml cell cultures were pelleted by centrifugation and resuspended in 110 µl of buffer containing 100 mM TRIS, pH 7.5, 150 mM NaCl, and 10% v:v glycerol (TNG buffer). In other cases, 3 ml cell cultures were pelleted by centrifugation and resuspended in 300 10 µl of TNG buffer. After sonication samples were centrifuged to furnish soluble and pellet fractions. Pellets were resuspended in a volume of TNG equal to the sonicant supernatant. 15 µl of the soluble and pellet fractions were mixed with 15 µl of 2×SDS denaturing buffer containing 100 mM TRIS, 200 mM dithiothreitol, 4% SDS, 0.2% bromophenol blue, and 20% glycerol, and were heated for 15 min at 100° C. The denatured samples were resolved on a 4-20% gradient Criterion SDS-PAGE (Biorad, Hercules, Calif.). The protein samples were stained using Gel Code Blue stain reagent (Pierce, Rockford, Ill.) and imaged using a GS-800 Calibrated Densitometer (Biorad, Hercules, Calif.). The calibrated scanner furnished the integrated optical density D of the protein spots. The total expressed protein content was estimated by adding the protein spot optical densities of the soluble ($D_s$) and the pellet fraction ($D_p$) and the solubility was defined as $S=D_s/(D_s+D_p)$. We used HPS as "bait" in a directed evolution schema in *E. coli* to discover mutants of GFP S11 for which the HPS-GFP S11 fusion solubility matched the HPS non-fusion solubility.

TABLE 3

Effect of GFP S11 tags on the solubility of eighteen test proteins from *Pyrobaculum aerophilum.*

| # | [a]Protein | [b]MW | [c]Fraction soluble | | | | |
|---|---|---|---|---|---|---|---|
| | | | [d]NF | [e]WT | [f]M1 | [f]M2 | [f]M3 |
| 1 | DNA-directed RNA polymerase | 12.5 | 0.05 | 0.00 | 0.00 | 0.35 | 0.10 |
| 2 | Sulfite reductase | 12.7 | 1.00 | 1.00 | 1.00 | 1.00 | 1.00 |
| 3 | c-type cytochrome biogenesis factor | 14.4 | 0.77 | 0.28 | 0.59 | 0.86 | 0.65 |
| 4 | Translation initiation factor | 15.4 | 0.40 | 0.30 | 0.80 | 0.70 | 0.45 |
| 5 | Ribosomal protein S9p | 16.4 | 0.70 | 0.50 | 0.75 | 0.80 | 0.75 |
| 6 | Polysulfide reductase subunit | 21.0 | 0.00 | 0.00 | 0.00 | 0.00 | 0.00 |
| 7 | Nucleoside diphosphate kinase | 21.6 | 0.00 | 0.00 | 0.00 | 0.15 | 0.10 |
| 8 | Tartrate dehydratase β-subunit | 23.8 | 0.00 | 0.00 | 0.00 | 0.00 | 0.00 |
| 9 | 3-hexulose 6-phosphate synthase | 23.1 | 0.65 | 0.00 | 0.30 | 0.85 | 0.60 |
| 10 | Hydrogenase formation protein hypE | 26.8 | 0.35 | 0.05 | 0.40 | 0.70 | 0.55 |
| 11 | Methyltransferase | 29.3 | 0.00 | 0.00 | 0.00 | 0.05 | 0.05 |
| 12 | Chorismate mutase | 29.3 | 0.70 | 0.00 | 0.35 | 0.65 | 0.70 |
| 13 | Tyrosine t-RNA synthetase | 36.0 | 0.95 | 0.70 | 0.90 | 0.90 | 0.95 |
| 14 | nirD protein | 36.7 | 0.70 | 0.15 | 0.40 | 0.65 | 0.45 |
| 15 | Soluble hydrogenase | 37.3 | 0.00 | 0.00 | 0.00 | 0.05 | 0.00 |
| 16 | Aspartate-semialdehyde. Dehydrog. | 37.4 | 0.00 | 0.00 | 0.00 | 0.05 | 0.00 |
| 17 | Phosphate cyclase | 37.4 | 0.80 | 0.30 | 0.85 | 0.95 | 0.90 |
| 18 | Purine-nucleoside phosphorylase | 41.7 | 0.05 | 0.00 | 0.00 | 0.10 | 0.00 |

[a]Eighteen proteins from the hyperthermophilic archaeon *Pyrobaculum aerophilum*(Fitz-Gibbon, Choi et al. 1997), expressed in *E. coli* BL21(DE3) at 37° C.
[b]Theoretical molecular weight in kD calculated from amino acid sequence.
[c]Fraction soluble as determined by SDS-PAGE densitometry. Relative uncertainty is ca. 5%, average of three replicates.
[d]Non-fusion (NF) solubility.
[e]C-terminal fusions with wild-type GFP 11 (WT).
[f]C-terminal fusions with GFP 11 optima (M1, M2, M3).

Figure 7:
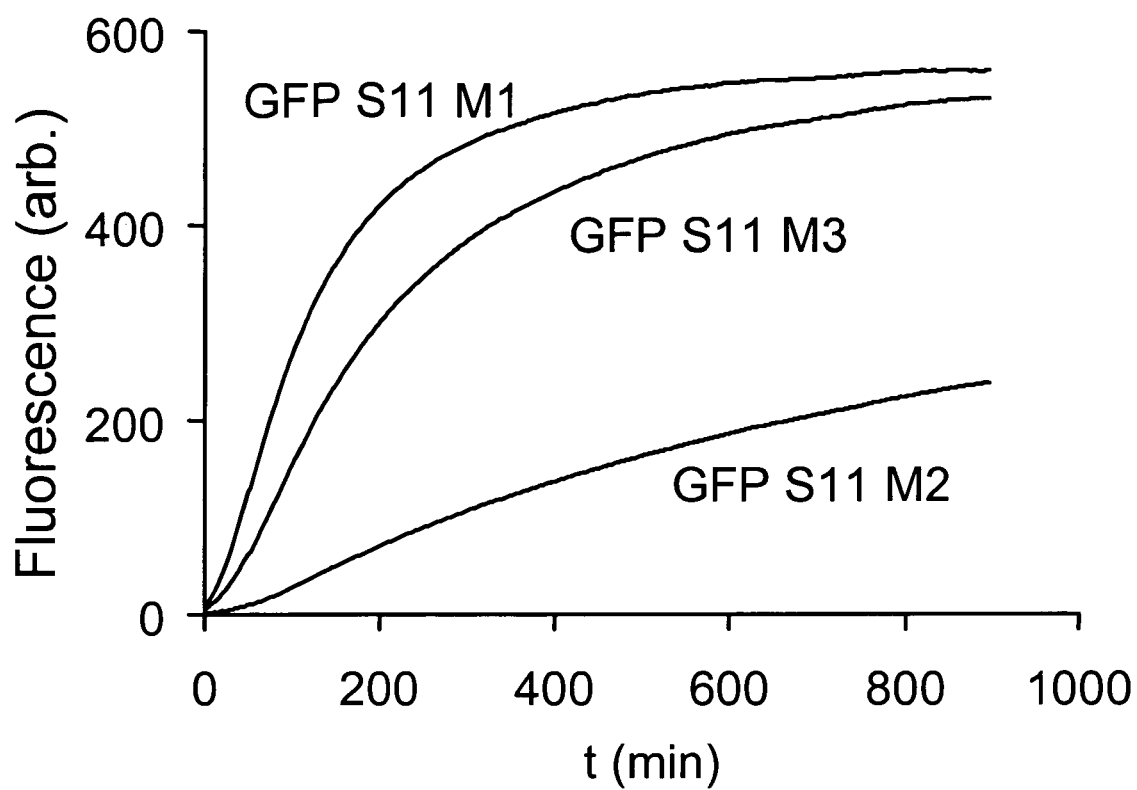
FIG. 7 shows fluorescence complementation kinetic traces for the three GFP S11 mutants M1, M2, and M3 fused to sulfite reductase (50 pmol) after the addition of excess GFP 1-10 OPT (800 pmol) in vitro in tissue culture plates. The final volume of each assay was 200 µl.

Libraries of HPS-GFP 11 variants and the GFP 1-10 OPT were expressed in sequence from the pTET-SpecR vector (see EXAMPLE 1, supra) and pET 28 vectors, respectively. This sequential induction protocol using independently-inducible compatible plasmids helped to avoid false-positives caused by co-translational folding and complementation of insoluble variants of HPS-GFP S11 with GFP 1-10 OPT. Hexulose phosphate synthase-GFP 11 (HPS-GFP S11) fusions were amplified by PCR and shuffled using published protocols (Stemmer 1994). The GFP S11 mutant library was expressed as a C-terminal fusion with the bait protein HPS bearing an N-terminal 6-HIS tag, from the PTET plasmid with an AnTET-inducible tet promoter (Lutz and Bujard 1997) (see FIG. 1 and EXAMPLE 1, supra) and transformed into a BL21(DE3) strain expressing GFP 1-10 OPT on a modified pET vector containing a p15 origin of replication. Optima were screened using a sequential induction protocol as follows. After overnight growth at 37° C., the nitrocellulose membrane bearing colonies was moved onto a selective LB/agar Bauer plate containing 300 ng/ml AnTet for 3 h at 37° C. to express the HPS-GFP S11 library, transferred to a fresh "resting" plate for 1 h to allow the AnTet to diffuse out of the colonies to shut off expression of the HPS-GFP S11, and finally moved to an LB/agar plate containing 1 mM IPTG for 2 h to induce expression of the complementary GFP 1-10 OPT from the pET plasmid. Since the HPS-GFP S11 wild type construct was entirely insoluble, colonies expressing the HPS-GFP S11 wild type and GFP 1-10 OPT according to the sequential expression protocol were only faintly fluorescent. Brighter clones, associated with more soluble HPS-GFP 11 optima, were picked into selective liquid culture 96-well tissue culture plates, and saved as −80° C. 20% glycerol stocks. The clones were grown in 1 ml liquid cultures and were induced with 300 ng/ml AnTET. The soluble fractions were screened for complementation efficiency in an in vitro assay with an excess of purified GFP 1-10 OPT (see infra, EXAMPLE 9). Clones with the fastest complementation rates were selected and pooled for an additional round of evolution and screening. Two rounds of evolution yielded two separate GFP S11 mutants, L221H and T225N. We initially focused on the L221H variant, termed GFP 11 M1. This mutation complemented GFP 1-10 OPT efficiently in vivo, and had improved solubility relative to HPS GFP S11 wild type, but did not entirely eliminate the deleterious effect of GFP S11 on fusion protein solubility (FIG. 6, and Table 3). GFP 11 M2 was engineered by combining F223S, a mutation that substantially increased the solubility of a different split GFP fragment (see EXAMPLE 11, infra) with T225N (see Table 3, supra). HPS-GFP S11 M2 solubility was greatly improved relative to either HPS-GFP 11 M1 or HPS-GFP 11 wild type (FIG. 6, Table 3). The complementation rate of HPS-GFP 11 M2 with GFP 1-10 OPT had decreased ca. 5-fold relative to HPS-GFP 11 M1 for comparable amounts of soluble fusion protein (FIG. 7)

We removed K214 from GFP S11 M2, a duplicate of the C-terminal residue of GFP 1-10 OPT, and screened a 64-fold degeneracy library at the hot-spot position 223 using a degenerate primer set, (methods well known in the art), and cloned the resulting variants of GFP 11 M2 as C-terminal fusions with HPS to search for more conservative mutations. The soluble fractions of ca. 200 clones were screened in an in vitro assay (see EXAMPLE 9, infra) with GFP 1-10 OPT. The best GFP S11 construct (L221H, F223Y, T225N) (termed GFP S11 M3, amino acid sequence RDHMVLHEYVNAAGIT [SEQ ID NO: 16], see Table 2 supra) balanced reduced perturbation of fusion protein solubility (FIG. 6, Table 2 supra) with good complementation (FIG. 7). We also attempted to improved the complementation of GFP 1-10 OPT by directed evolution following the methods outlined in EXAMPLE 3, supra, using the GFP S11 M2 tag as the complementation target. This produced a variant termed GFP 1-10 A4, which exhibited ca. 5-fold faster complementation with GFP S11 M2 relative to GFP 1-10 OPT. GFP 1-10 A4 contained the superfolder mutations and the additional mutations R80Q, S99Y, T105N, E111V, I128T, K166T, E172V, and S205T. The A4 variant is expressed predominantly as inclusion bodies in E. coli and is less useful for in vivo assays relative to the GFP 1-10 OPT. However, variant A4 is useful for in vitro assays since it can be refolded from inclusion bodies simply by dilution of urea-solubilized pellets in fresh TNG buffer, and complements GFP S11 M2 or GFP S11 M3 ca. four-fold faster than does GFP 1-10 OPT.

Example 5

Comparing Effect of Sequential Induction or Co-Induction Using Soluble or Insoluble Versions of GFP 1-10

Figure 8:
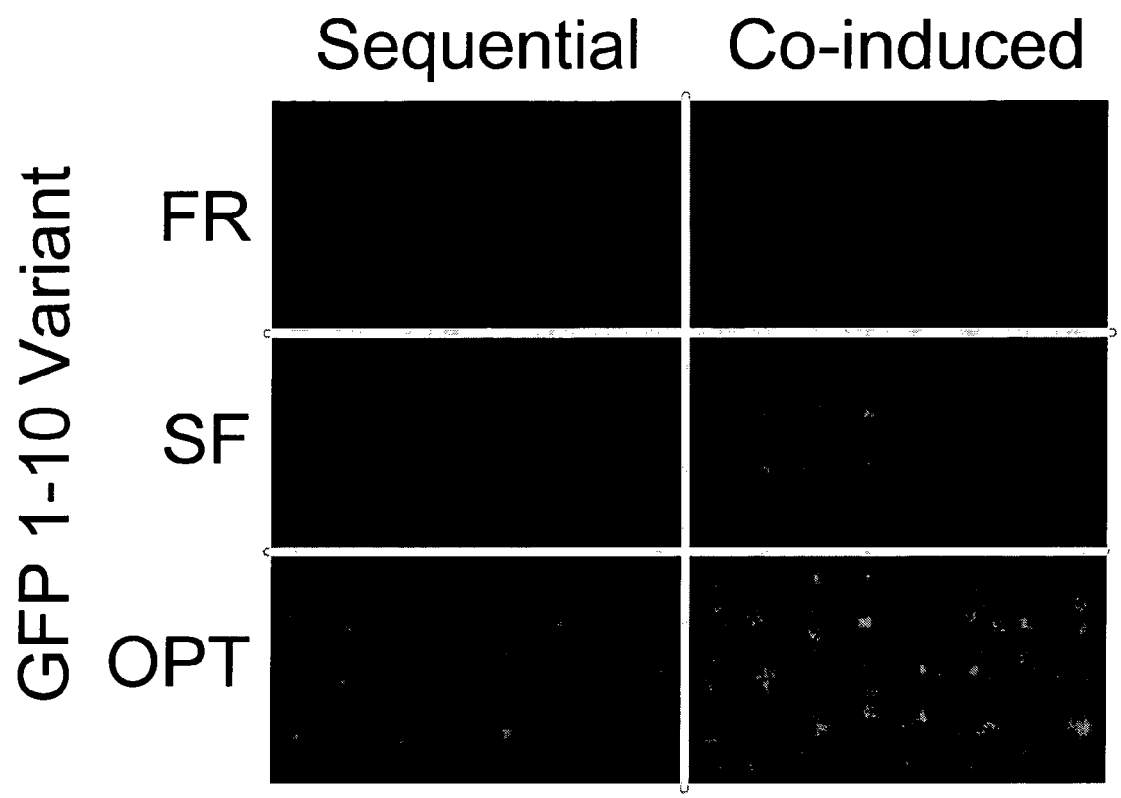
FIG. 8 shows effect of sequential (left column) or co-induction protocols (right column) using three different GFP 1-10 constructs. Fluorescence images of three rows of *E. coli* clones expressing GFP 1-10 constructs with progressively better performance and solubility: folding reporter (FR, first row), superfolder (SF, second row), or the optimized GFP 1-10 variant (OPT, third row). Superfolder GFP 1-10 is insoluble when expressed alone. First column: transient expression of GFP 1-10 followed by expression of sulfite reductase-GFP S11 fusion. Second column: co-expression of GFP 1-10 along with sulfite reductase-GFP S11 wild type. Superfolder GFP 1-10 is insoluble, and cells are faintly fluorescent following the transient induction protocol, likely because the superfolder GFP 1-10 can aggregate prior to the expression of the sulfite reductase-GFP S11 wild type fusion, reducing complementation efficiency. Co-expression gives bright cells likely because binding and complementation between the superfolder GFP 1-10 and sulfite reductase-GFP S11 can occur rapidly, rescuing GFP 1-10 from misfolding and aggregation. In contrast, cells expressing the partially soluble GFP 1-10 OPT are bright whether the constructs are sequentially expressed or co-expressed.

To test the hypothesis that co-induction could lead to complementation of the insoluble and aggregated superfolder GFP 1-10, we compared sequential and co-induction protocols. BL21(DE3) E. coli cells co-transformed with the large GFP 1-10 fragment (folding reporter GFP 1-10, superfolder GFP 1-10, or GFP 1-10 OPT) on vector pTET with a ColE1 origin, and sulfite reductase-GFP S11 wild type on a pET plasmid with a p15 origin were plated on duplicate nitrocellulose membranes on nutrient agar plates, and grown until ca. 1 mm in diameter overnight. One membrane was processed using the sequential induction protocol (see EXAMPLE 4, supra). Briefly, GFP 1-10 was expressed first using AnTET, followed by resting on a fresh plate to remove the AnTET, followed by expression of sulfite reductase-GFP S11 wild type on a fresh plate containing 1 mM IPTG. A duplicate plate was separately co-induced (plate containing both AnTET and IPTG). The fluorescent colonies were illuminated with 488 nm light using an IllumaTool (LightTools Research, Encinitas, Calif.), and imaged through a 520 nm long-pass filter using a Kodak DC290 digital camera. When superfolder GFP 1-10 is expressed transiently, and allowed to aggregate in vivo prior to induction of the sulfite reductase-GFP S11 wild type, the cells are faint (FIG. 8). In contrast, cells expressing the partially soluble GFP 1-10 OPT and sulfite reductase-GFP S11 constructs are bright whether co-expressed or sequentially expressed, as expected (FIG. 8).

Example 6

Sensitivity of Split GFP Assay Performed In Vitro

Figure 9:
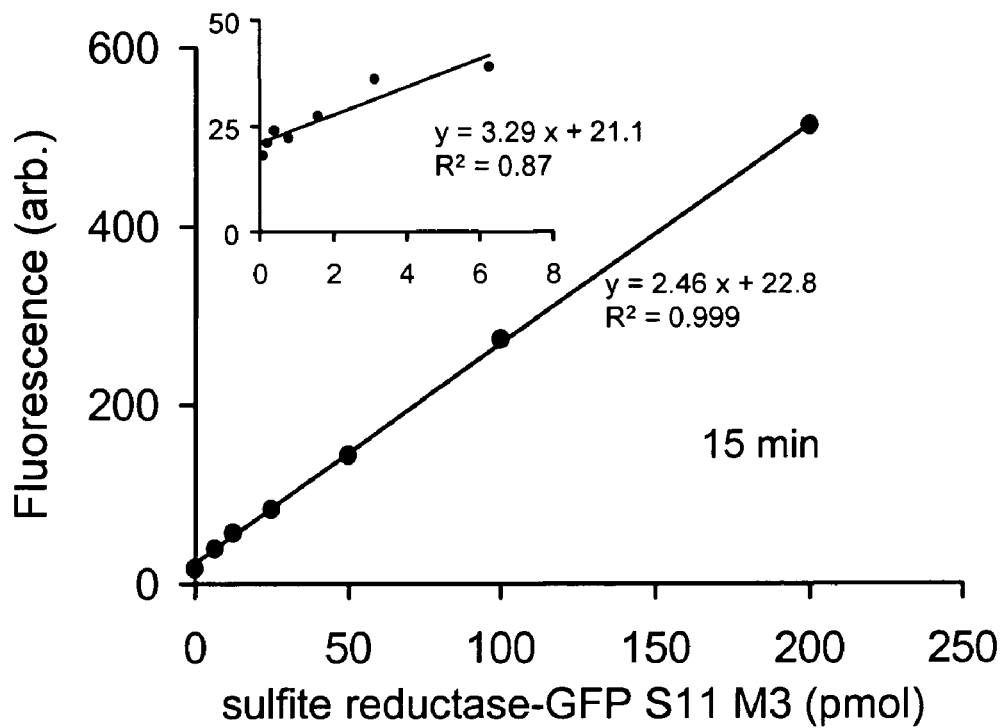
FIG. 9 shows sensitivity of split GFP complementation using GFP S11 M3 tag fragment and GFP 1-10 OPT assay fragment. 20 µl aliquots containing 0.1 to 200 pmol of sulfite reductase-GFP S11 M3 fusion protein were mixed with 180 µl aliquots containing 800 pmol GFP 1-10 OPT to start complementation. (A) Fluorescence measured for each solution 15 min after addition of GFP 1-10 OPT. (B) Fluorescence measured for each solution 1 h after addition of GFP 1-10 OPT.
Figure 9:
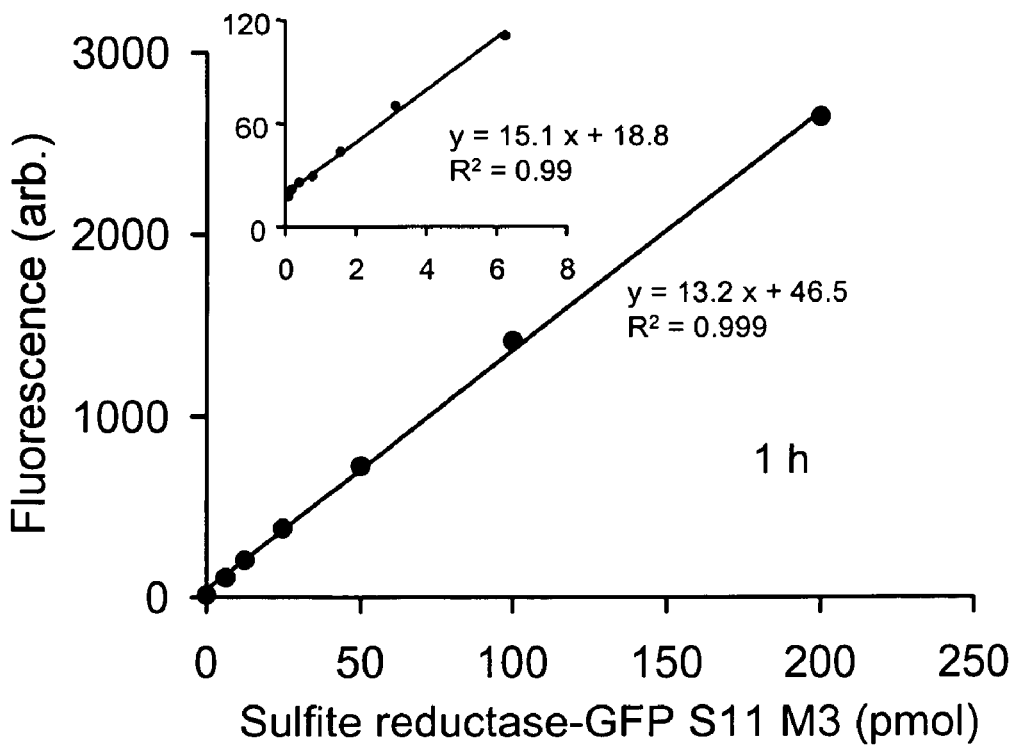
Figure 10:
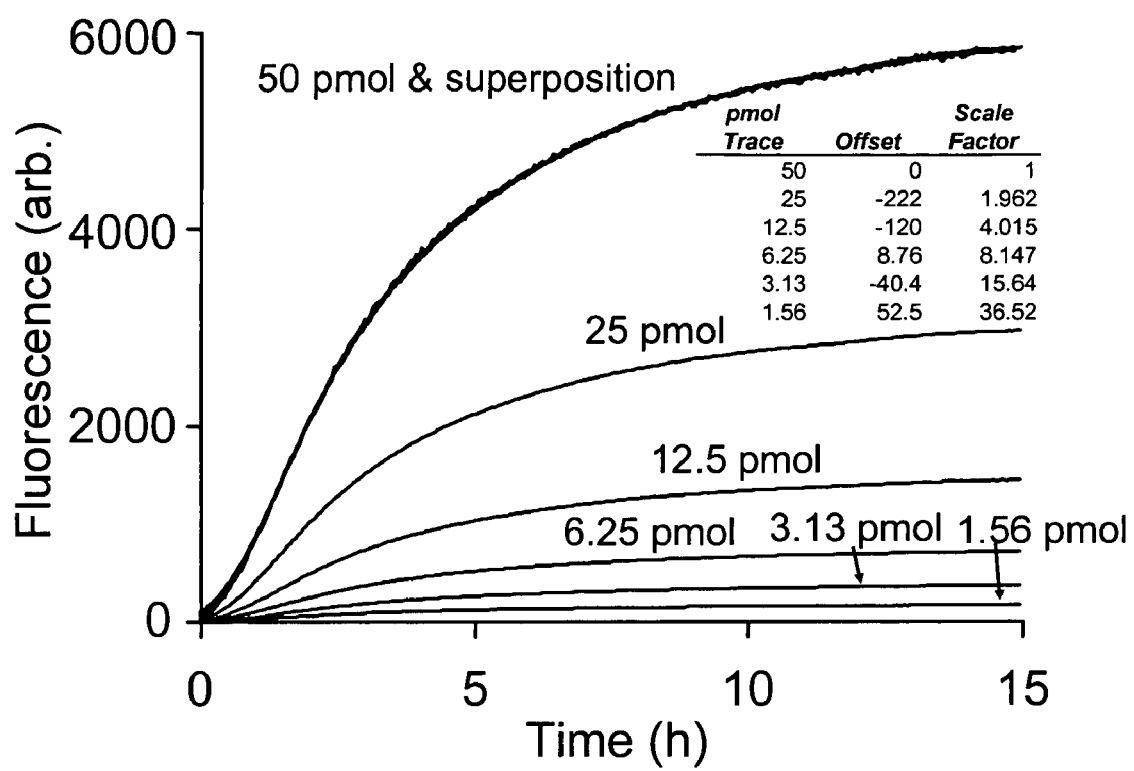
FIG. 10 shows progress curves for complementation of 50, 25, 12.5, 6.25, 3.13, and 1.56 pmol samples of sulfite reductase fused to GFP S11 M3. The data were fit to the 50 pmol progress curve by subtracting a small constant and applying a scaling factor (see inset table in FIG. 10), calculated by non-linear least-squares using the EXCEL data analysis tool Solver (Microsoft, Inc.). The excellent superposition indicates that the shape of the progress curve does not depend on the concentration of the tagged protein, or depletion of the pool of unbound GFP 1-10 OPT fragment.

We measured fluorescence progress curves for complementation of several different amounts of purified sulfite reductase-GFP S11 M3 in 200 µl reactions in a microtiter plate (FIG. 9). We avoided potential higher-order kinetic effects by initiating the complementation using a high concentration and large molar-excess of GFP 1-10 OPT (800 pmol). For these sensitivity experiments, a 96-well microplate was first blocked with a solution of 0.5% bovine serum albumin (BSA) in buffer TNG (100 mM TRIS pH 7.5, 150 mM NaCl, 10% v:v glycerol) for 10 minutes. 2-fold serial dilutions of Talon resin-purified (Clontech, Palo Alto, Calif.) 6HIS-sulfite reductase-GFP S11 M3 fusion protein were performed in the same buffer. The dilutions spanned the range 200 to 0.1 pmol per 20 µl aliquot, the aliquots were added to the wells of a 96-well plate, and then complementation was performed using a large excess (800 pmol) of GFP 1-10 OPT (ca. 0.5 mg/ml) added in a 180 µl aliquot such that the concentration of the large fragment was not limiting. To test the effect of crude E. coli lysate on the sensitivity of the reaction, in a separate experiment, samples were also spiked by addition of 20 µl of lysate from E. coli BL21 (DE3) expressing an irrelevant non-tagged protein prior to the addition of the GFP 1-10 OPT. Fluorescence kinetics ($\lambda_{exc}$=488 nm, $\lambda_{em}$=530 nm) were monitored with a FL600 microplate fluorescence reader (Bio-Tek, Winooski, Vt.), recorded at 3 min intervals, for 15 h. The background fluorescence of a blank sample (20 µl of E. coli lysate expressing an irrelevant protein, 100 µl of 0.5 mg/ml GFP 1-10 OPT, and 100 µl of 0.5% BSA in TNG buffer) was subtracted from final fluorescence values. The blank was less than 30% the signal from the lowest target concentration (0.1 pmol sulfite reductase-GFP S11 M3). Complementation fluorescence was a linear function of analyte concentration (FIG. 9). 10 to 200 pmol amounts of sulfite reductase-GFP S11 M3 could be accurately quantified within 15 min after the addition of GFP 1-10 OPT (FIG. 9A), and 0.1 to 10 pmol required ca. 1 h (FIG. 9B). Progress curves over a wide concentration range could be superimposed by simple linear scaling (FIG. 10), indicating that the kinetics of the reaction was not limited by the concentration of GFP 1-10 OPT. Smooth lines fitted to the curves shown in FIG. 9 can compromise calibration curves for determining the amount of protein in a test sample tagged with the GFP tagging domain, as long as the test sample is measured under the same conditions as employed in measuring the samples of known concentration (for example, the calibration curve exemplified of FIG. 9A for sulfite reductase-GFP S11 M3, using the same assay reagent concentration of GFP 1-10 OPT, and same volumes of sample). Thus, in FIG. 9A, the linear fit of fluorescence (Y) to pmol is given by Y=2.46×(pmol)+22.8. Suppose we measure an unknown concentration of tagged protein under the same conditions as the calibration curve, yielding a measured fluorescence of 200 units. Solving for pmol=(Y−22.8)/2.46, and substituting Y=200, we can calculate pmol=(200−22.8)/2.46=72.0 pmol.

Example 7

Rapid Binding of the Split GFP Fragments

Figure 11:
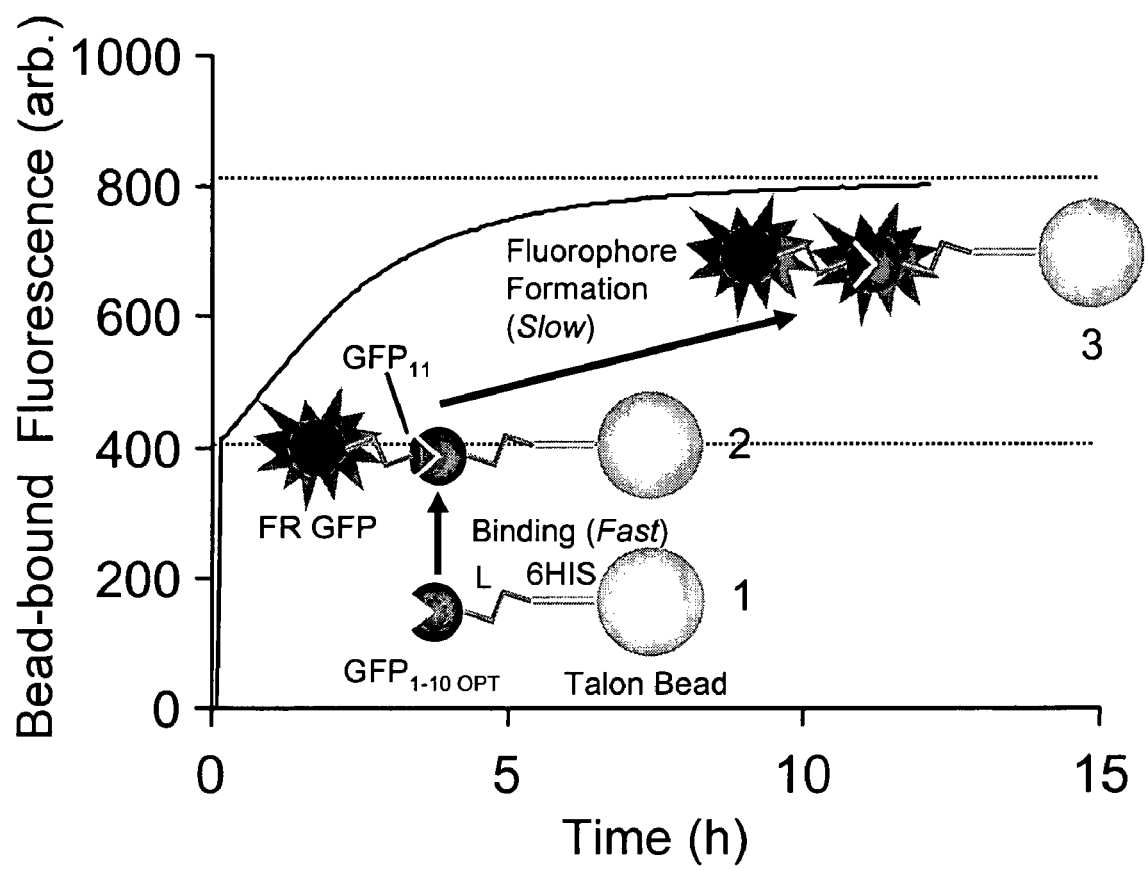
FIG. 11 shows binding to and complementation of Talon resin-bound 6HIS GFP 1-10 OPT by folding reporter GFP tagged with C-terminal GFP S11 M3. (1) Talon resin with bound 6HIS GFP 1-10 OPT, (2) rapid increase in bead-bound fluorescence by binding of folding reporter GFP via fused C-terminal GFP S11 M3, (3) slow fluorescence formation due to complementation.

To distinguish between the binding kinetics of the split GFP fragments and the kinetics of chromophore formation, we performed complementation of Talon resin-bound 6HIS GFP 1-10 OPT by GFP S11 M3 tagged with N-terminal folding reporter GFP. A 100 µl aliquot of 50% v/v slurry of Talon resin was saturated with GFP 1-10 OPT bearing an N-terminal 6HIS affinity tag (200 µl of 2 mg/ml protein). The beads (50 µl bed volume) were washed 3 times with 300 µl of TNG buffer to remove unbound GFP 1-10 OPT, the remaining buffer aspirated and discarded, and the fluorescence measured in a 96 well microtiter plate (FIG. 11, Step 1). Excess folding reporter GFP-GFP S11 M3 fusion protein (200 µl of 5 mg/ml protein) was added to the beads, mixed by pipetting for 15 s, rapidly transferred to a small 0.2µ spin filtration column, and washed 3 times with 0.5 ml aliquots of TNG to remove unbound folding reporter GFP-GFP S11 M3 protein. This procedure required approximately 5 min. Beads were transferred to a fresh well of the microtiter plate (FIG. 11, Step 2) and the fluorescence measured at 3 min intervals for 12 h (FIG. 11, Step 3). Fluorescence of the beads showed that folding reporter GFP-GFP S11 M3 protein rapidly bound to 6HIS-GFP 1-10 OPT (FIG. 11, Step 2). The washed beads gained additional fluorescence at a rate comparable to that observed in solution (FIG. 11, Step 3), indicating that the kinetics of fluorescence formation was not limited by the rate of association of the GFP fragments.

Example 8

Robustness of the Complementation Assay and Effect of Adjuvants and pH

Figure 12:
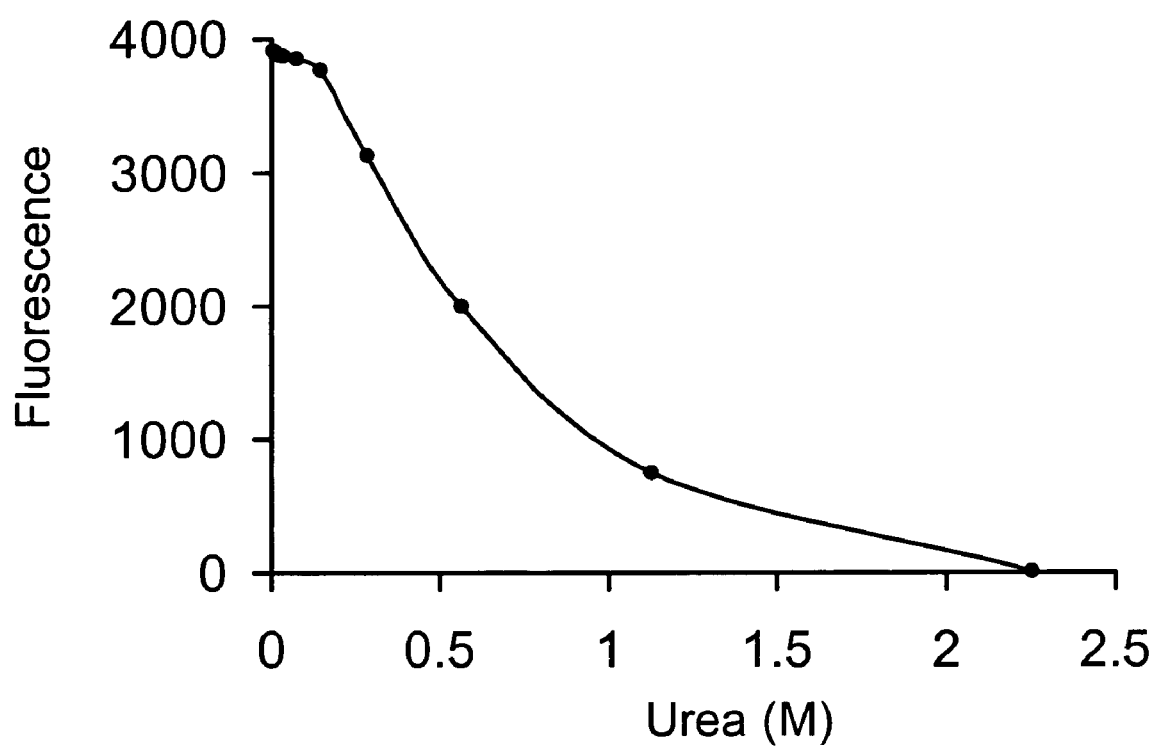
FIG. 12 shows effect of urea concentration on the complementation reaction. Reaction is quenched above 2 M urea.
Figure 13:
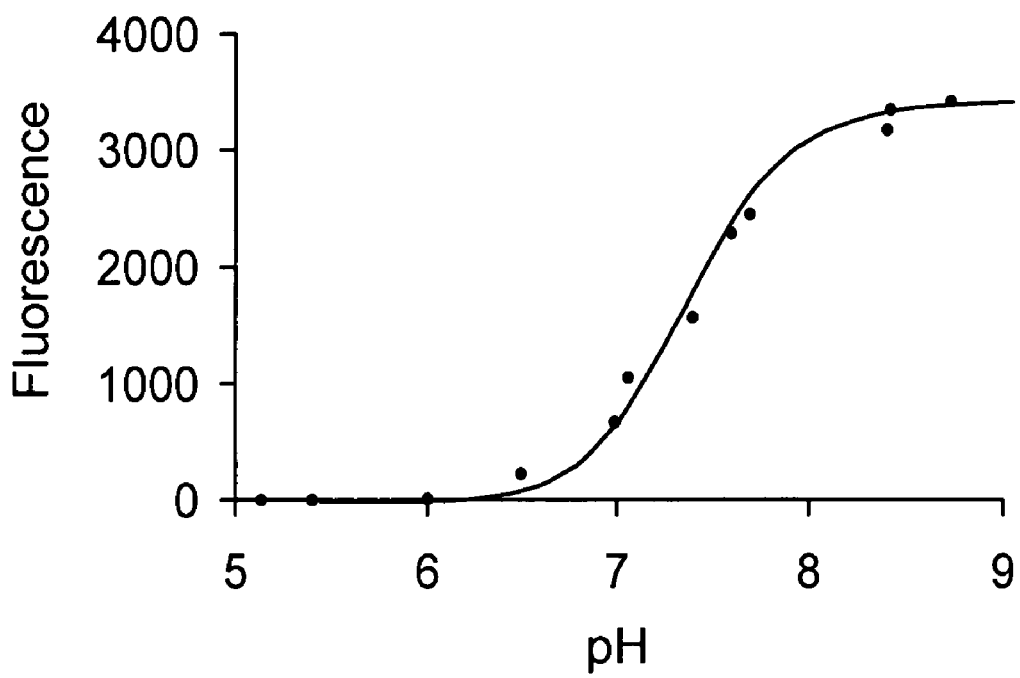
FIG. 13 shows effect of pH on the complementation reaction. (A) pH dependence of final fluorescence for sulfite reductase-GFP S11 M3 6 h after addition of GFP 1-10 OPT. (B) pH dependence of final fluorescence for synthetic peptide GFP S11 6 h after addition of GFP 1-10 OPT. Fluorescence complementation appears inefficient below pH 6.5.
Figure 13:
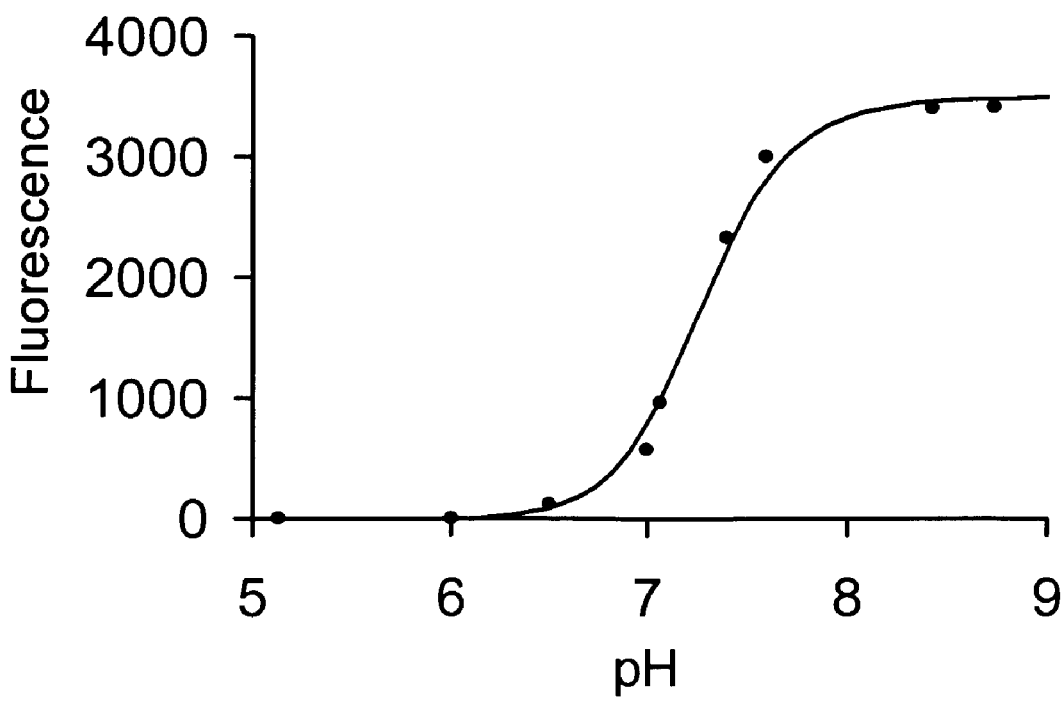

We tested the effect of common chemical adjuvants and pH on the complementation reaction. Ten sequential 2-fold sequential dilutions of 9 M urea were performed with TNG. 100 µl aliquots of the ten solutions, ranging in concentration from 9 M down to 0.019 M urea, were combined with 10 µl of sulfite reductase-GFP 11 M3, 10 µl of the assay fragment GFP 1-10 OPT, and 80 µl of TNG buffer. Fluorescence data was collected for 12 h at 3 minute intervals with a FL-600 plate reader (BIOTEK, Winooski, Vt.). The reaction was quenched above 2.0 M urea (FIG. 12). In a separate experiment, the complementation rate improved ca. 30% by 5 mM dithiothreitol, but quenched by 0.1% w/v SDS. We next tested the effect of different pH solutions on the efficiency of the complementation reaction. 10 µl of equimolar solutions of sulfite reductase-GFP S11 M3 fusion protein or S11 wild type peptide were added to 180 µl of an 0.1 M solution containing the appropriate buffer MES (pH 5-6.5), HEPES (pH 6.5-7.5), TRIS (pH 7.5-8.5), BICINE (pH 8.5-9.0), over the pH range 5.0 to 9.0 in 0.5 pH unit intervals. Complementation was initiated by adding 10 µl of GFP 1-10 OPT (4 mg/ml) and complementation kinetics were monitored overnight at 3 min intervals with a FL-600 plate reader (BIOTEK, Winooski, Vt.). Complementation was inefficient below pH 6.5 with an apparent pKa of ca. pH 7.3 (FIG. 13). After complementation the fluorescent GFP moiety displayed a slow time-dependent decrease in fluorescence above 5 M urea ($t_{1/2} \approx 20$ h), and a pKa of ca. 5.5 similar to "enhanced" GFP (Patterson, Knobel et al. 1997).

Example 9

In Vitro Protein Quantification

Figure 14:
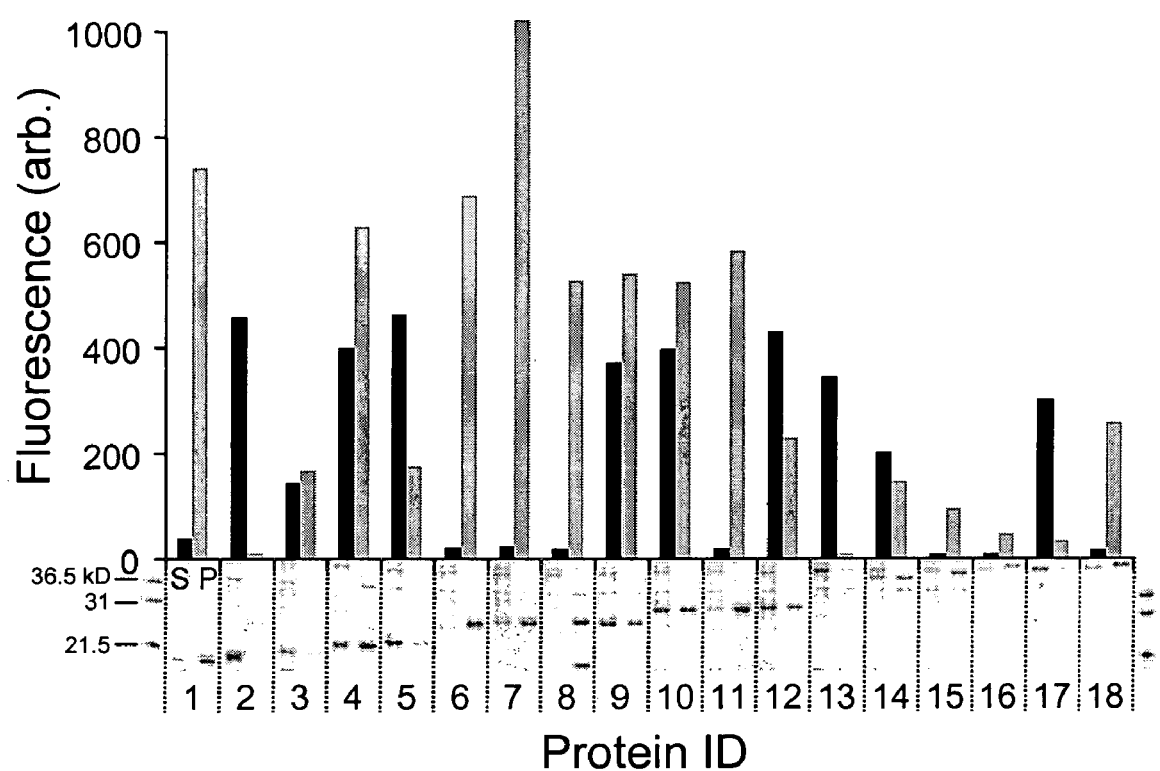
FIG. 14 bar graph shows in vitro protein quantification of eighteen *Pyrobaculum* test proteins (see supra, Table 3) with C-terminal GFP S11 M3 tags, using the split GFP system. The GFP fragment complementation assay fluorescence of soluble (black bars) and unfolded pellet fractions (grey bars) using GFP 1-10 OPT. SDS-PAGE gel shows the corresponding soluble (S), and pellet fractions (P). Note that protein #8, tartrate dehydratase β-subunit, shows a second lower band at ca. 13 kD.

To test whether the split GFP system could accurately quantify different proteins in vitro, we expressed eighteen *Pyrobaculum* proteins as pET vector constructs with C-terminal GFP S11 M3 tags in liquid culture, and then analyzed the soluble and pellet fractions using SDS-PAGE and the split GFP complementation system (FIG. 14). To assay soluble fractions of the eighteen *Pyrobaculum* proteins for pET-expressed protein quantification tests, and to perform assays on optima during directed evolution of the GFP S11 and GFP 1-10 variants, 20 µl of target protein soluble fractions of cell lysates were mixed with 180 µl of 0.35 mg/ml refolded GFP 1-10 OPT (ca. 600 pmol) in a 96 well microplate (Nunc-Immuno™ plate, Nunc, Rochester, N.Y.). To assay insoluble pellets, 50 µl of each resuspended insoluble fraction was centrifuged, the dried pellets were dissolved by addition of 50 µl of 9 M urea, and then 10 µl of the unfolded samples were assayed by rapid addition of 190 µl of 0.35 mg/ml GFP 1-10 OPT in TNG. The fluorescence values of the pellet assays were scaled by a factor of two to compensate for the lower volume relative to the soluble assays, allowing direct comparison with the soluble fraction assays. The final concentration of urea in the assay was ca. 0.4 M (see EXAMPLE 8, supra and FIG. 12). To quantify the samples by SDS-PAGE, 15 µl of the soluble and pellet fractions were mixed with 15 µl of 2×SDS denaturing buffer containing 100 mM TRIS, 200 mM dithiothreitol, 4% SDS, 0.2% bromophenol blue, and 20% glycerol, and were heated for 15 min at 100° C. The denatured samples were resolved on a 4-20% gradient Criterion SDS-PAGE (Biorad, Hercules, Calif.). The protein spots on gels were stained using Gel Code Blue stain reagent (Pierce, Rockford, Ill.) and imaged and optical density of protein spots quantified using a GS-800 calibrated scanning densitometer (Biorad, Hercules, Calif.). Even though Coomassie dye exhibits protein-dependent variations in staining efficiency (Tal, Silberstein et al. 1985), after the completion of complementation and folding (ca. 6 h), there was a strong correlation between the measured fluorescence values and the amount of protein as visualized by SDS-PAGE (FIG. 14). Insoluble proteins dissolved in 9 M urea (see this example, supra) and diluted 20-fold with buffer containing excess GFP 1-10 OPT gave fluorescence well correlated with the amount of insoluble protein visualized by SDS-PAGE (FIG. 14). In contrast, when solubilized pellets were diluted with fresh buffer prior to the addition of an aliquot of concentrated GFP 1-10 OPT, several of the well-expressed insoluble proteins (i.e., polysulfide reductase and nucleotide diphosphate kinase, Table 3 and FIG. 14) gave no detectable complementation. Likely these proteins had misfolded and aggregated upon dilution, making the GFP 11 M3 tag inaccessible prior to the subsequent addition of the GFP 1-10 OPT moiety.

Example 10

Estimating In Vivo Soluble and Total Protein Using Split GFP Assay System

Figure 15:
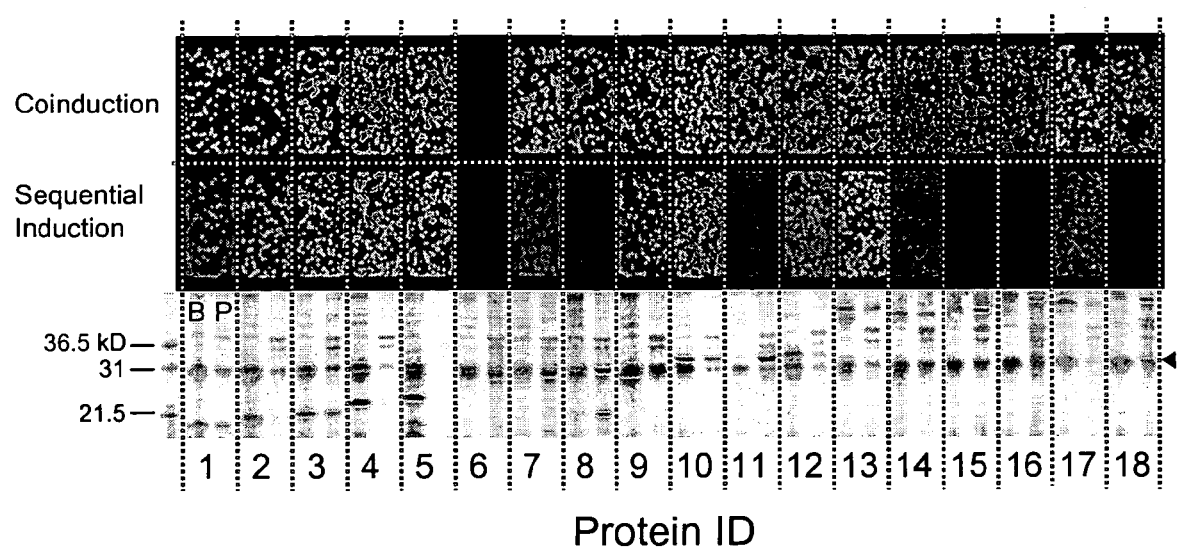
FIG. 15 shows in vivo solubility and expression screen using split GFP assay system. Eighteen *Pyrobaculum* test proteins (see Table 3, supra) expressed with an N-terminal 6HIS tag and a C-terminal GFP S11 M3 tag from a tet-promoter plasmid, were cloned into an *E. coli* BL21 (DE3) strain containing a pET plasmid expressing GFP 1-10 OPT. Fluorescence images of colonies on plates after co-induction of the tagged constructs and GFP 1-10 OPT (top), or transient expression of the tagged constructs followed by expression of the GFP 1-10 OPT (Sequential Induction, middle). SDS-PAGE of Talon resin bead-bound soluble (B) and pellet fractions (P) from cells sequentially induced in liquid culture (bottom). Adventitiously-bound GFP 1-10 OPT (apparent molecular weight ca. 29 kD) is indicated by arrow. Note that nucleoside diphosphate kinase (protein #7) is partially soluble (see band slightly below band corresponding to GFP 1-10 OPT in Talon resin-bound fraction). Polysulfide reductase-GFP S11 M3 fusions (see Table 3, supra) produced intensely red-colored colonies, absorbing the 488 nm excitation light and reducing whole-cell fluorescence during co-expression despite the good expression of the protein.

A practical split protein tagging system could be used in vivo to label and detect either soluble or insoluble proteins. We theorized that soluble protein could be assayed in living *E. coli* cells by first expressing the tagged protein for a limited time, and then shutting off the expression to allow the tagged protein to develop its intrinsic solubility phenotype prior to the subsequent expression of the complementary GFP fragment in the same cellular compartment. From the results of our co-refolding in vitro pellet assays (see EXAMPLE 9, supra), we expected that co-expressing the GFP S11 M3 tagged protein and GFP 1-10 OPT would lead to structural complementation and commitment to the development of GFP fluorescence prior to the aggregation of the test protein in vivo, enabling an estimate of the total expressed protein. *E. coli* BL21 (DE3) cells co-expressing *Pyrobaculum* test proteins with an N-terminal 6HIS and a C-terminal GFP S11 M3 tag from pTET-SpecR plasmids (FIG. 1, see supra), and GFP 1-10 OPT from a pET vector (Novagen, Madison, Wis.), were grown to saturation in LB containing 50 µg/ml kanamycin and 70 µg/ml spectinomycin and diluted in 20% glycerol at OD 600 nm=1.0 for –80° C. freezer stocks. Cells were diluted successively with two 400-fold dilutions in LB and plated on nitrocellulose membranes. After overnight growth at 32° C., the cells were induced sequentially (see EXAMPLE 4, Engineering GFP S11, supra) or co-induced. For the sequential induction, cells on membranes bearing the overnight colonies were incubated for 1.5 h on a plate containing 250 ng/ml AnTet, 1 h on a resting plate, and finally 1 h on 1 mM IPTG plate (note shorter induction times relative to those used for engineering GFP S11, EXAMPLE 4, supra). For the co-induction protocol, membranes bearing the overnight colonies were moved to plates containing both 600 ng/ml AnTET and 1 mM IPTG and incubated for 4 h at 37° C. to co-express both the GFP S11 fusions and the large GFP fragment 1-10. The induced colonies on the plates were illuminated using an Illumatool Lighting System® (LightTools Research, Encinitas, Calif.) equipped with a 488 nm excitation filter, and photographed with a DC290 digital camera (Kodak) through a colored glass filter (520 nm long pass, LightTools Research, Encinitas, Calif.). The fluorescent colonies were imaged after co-expression or after sequential expression, and soluble and pellet fractions of the same constructs were analyzed by SDS-PAGE (FIG. 15) after sequential induction in liquid culture. We assessed the amount of useful, non-aggregated 6HIS-tagged protein by binding soluble fractions to excess Talon resin (Novagen, Madison, Wis.) prior to the SDS-PAGE analyses. Briefly, to analyze soluble and pellet fractions of the same clones used for the in vivo whole-cell plate complementation assays, the clones were separately grown at 37° C. in a 1 ml 96-well culture plate. Cells were induced in the exponential phase with 250 ng/ml AnTET for 1 h, washed three times with fresh LB, and then induced with 1 mM IPTG for 1.5 h. After induction, the culture pellets were resuspended with 110 µl of TNG buffer, and disrupted by sonication. The lysate was fractionated by centrifugation to yield the soluble and the pellet fractions. 40 µl of the soluble extract of sequentially induced liquid cultures was mixed with an equal volume of 50% v/v slurry of metal affinity resin beads (Talon resin, Clontech, Palo Alto, Calif.) in TNG buffer and centrifuged briefly. The unbound fraction was removed by pipetting, and the beads were washed successively two times with an excess of TNG buffer. After the last centrifugation step, the buffer was discarded. 40 µl of 2×SDS denaturing buffer were added and heated for 15 min at 100° C. The insoluble fraction was denatured as described (see EXAMPLE 4, supra). The Talon-bound and denatured samples were each resolved on a 4-20% gradient Criterion SDS-PAGE gel (Bio-Rad, Hercules, Calif.). The protein samples were stained using Gel Code Blue stain reagent (Pierce, Rockford, Ill.) and imaged using a GS-800 Calibrated Densitometer (Biorad, Hercules, Calif.). Co-induction in vivo colony fluorescence reported total protein in agreement with SDS-PAGE, while sequential induction colony fluorescence agreed with SDS-PAGE of Talon-bound soluble protein (FIG. 15). Colonies expressing highly soluble proteins were bright whether the GFP 1-10 was co-induced or sequentially induced (proteins 2, 4, and 5, FIG. 15). Colonies expressing insoluble proteins were much brighter when the GFP 1-10 was co-induced (proteins 8, 11, 15, 16, and 18, FIG. 15). Proteins 1, 4, 5, 7, 9, 12 and 14 were each less soluble when expressed from the very strong T7 promoter (Studier, Rosenberg et al. 1990) of the pET system (Table 3 and FIG. 14, supra), than from the weaker tet promoter (Lutz and Bujard 1997) of the pTET plasmid (FIG. 15). The influence of promoter strength on protein expression levels and solubility has been noted previously (Makrides 1996; Baneyx 1999; Gerstein, Edwards et al. 2003; Yokoyama 2003; Fahnert, Lilie et al. 2004).

Example 11

Figure 16:
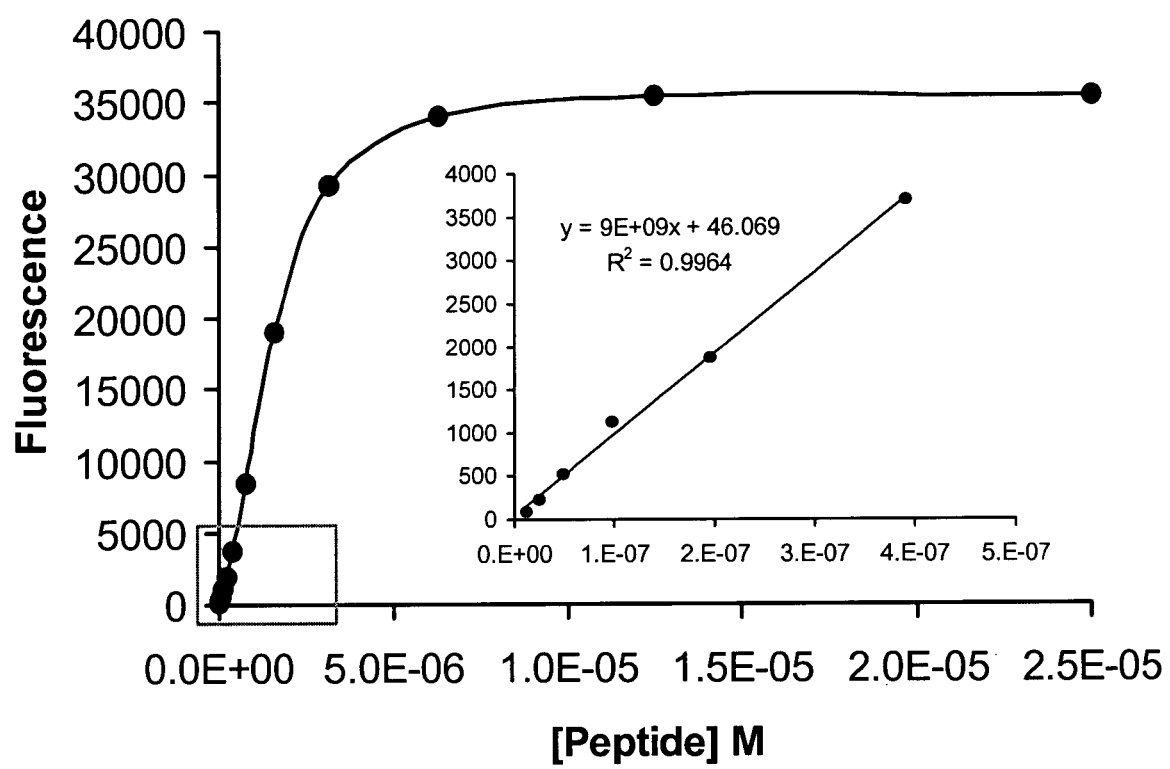
FIG. 16 shows the shows sensitivity of split GFP complementation using GFP S10-11 OPT tag fragment and GFP 1-9 OPT assay fragment. 20 µl aliquots containing sulfite reductase-GFP S10-11 OPT fusion protein were mixed with 180 µl aliquots containing 250 µM GFP 1-9 OPT to start complementation. Fluorescence measured for each solution 6 h after addition of GFP 1-10 OPT. Since the concentration of GFP 1-9 OPT is limiting, the fluorescence plateaus above ca. 250 µM sulfite reductase-GFP S10-11.

Engineering a Split GFP Complementation Pair Consisting of a GFP S10-11 Tag Fragment and GFP 1-9 Assay Fragment Following method of EXAMPLE 2, supra, we identified a feasible split GFP pair comprised of a tag domain consisting of superfolder GFP amino acids 198-238, (GFP S10-11), and a complementary assay fragment consisting of superfolder GFP amino acids 1-198, (GFP 1-9), which produced fluorescent cells when the two fragments were co-expressed in E. coli. GFP 1-9 was insoluble expressed alone in E. coli. Neither fragment expressed alone was fluorescent. Following the prescription of EXAMPLE 3, supra, and using the sulfite reductase-GFP S10-11 fusion protein as the complementation target, we improved the folding and solubility of the GFP 1-9 by directed evolution to yield the new variant GFP 1-9 OPT, which contained the mutations of superfolder GFP (see EXAMPLE 2, supra) and the additional mutations S2R, T43S, A87V, F114S, and K166T. This fragment was ca. 50% soluble expressed at 37° C. in E. coli from a pET 28 vector (Novagen, Madison, Wis.). Next we improved the solubility of GFP S10-11 and reduced its perturbation of fusion protein folding and solubility following the prescription of EXAMPLE 4, supra, using the evolved GFP 1-9 OPT as the complementation target. Superfolder GFP S10-11 tag has the sequence NHYLSTQSVLSKDPNEKRDHMVLLEFVT-MGITHGMDELYK [SEQ ID NO: 25], while the optimized GFP S10-11 has the sequence DHYLSTQTILSKDPNEER-DHMVLLESVTMGITHGMDELYK [SEQ ID NO: 26] (mutations N198D, S205T, V2061, K214E, F223S). The sensitivity of the in vitro split GFP assay using these fragments was tested according to EXAMPLE 6, supra, but with a limiting amount of GFP 1-9 OPT (2.5 µM GFP 1-9 OPT). Under these conditions, fluorescence reached a plateau at or above 2.5 µM tagged fragment concentration, as expected (FIG. 16).

Example 12

Figure 20:
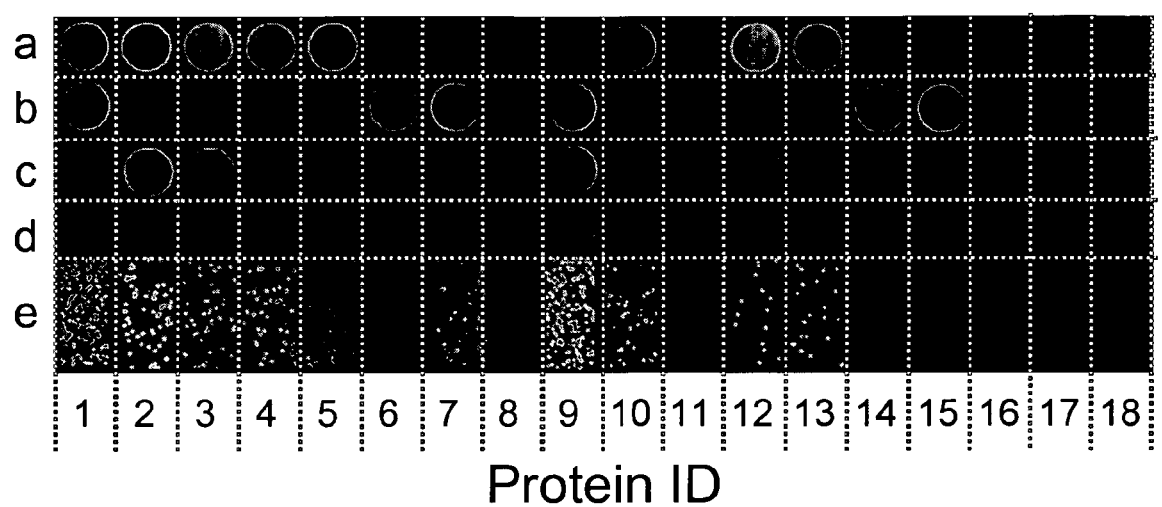
FIG. 20 shows in vitro and in vivo complementation assays of eighteen Pyrobaculum control proteins X cloned into the NdeI/BamHI cloning site of a pTET vector with (GFP S10 A10)-GGGS-NdeI-X-BamHI-GGGS-(GFP S11 SM5), and transformed into a BL21(DE3) strain containing GFP 1-9 OPT on a pET 28 vector with a p15 origin. For in vitro assay, liquid cultures were induced only with AnTET. (a) 20 µl soluble aliquot assayed with GFP 1-10 OPT (b) 10 µl urea-solubilized pellet aliquot assayed with GFP 1-10 OPT (c) 20 µl soluble aliquot assayed with GFP 1-9 OPT (d) 10 µl urea-solubilized pellet aliquot assayed with GFP 1-9 OPT. (e) Fluorescent images of E. coli after transient induction of sandwich tag construct from PTET using AnTET reagent, then induction of GFP 1-9 using IPTG. GGGS linker [SEQ ID NO: 44]

Engineering a (GFP S10)-X-(GFP S11) Sandwich Tag Format and Detection Using Assay Fragment GFP 1-9 OPT To stringently test when both ends of a target protein were covalently attached, and to reduce potential artifacts associated with tagging only one end of a target protein, such as short fragments caused by proteolysis or internal ribosome binding sites, we engineered a sandwich format where test proteins are expressed as fusions between two small domains of GFP, which are then complemented by a third domain of GFP. In this embodiment, test protein X is expressed as a sandwich between GFP strands 10 and 11 as (GFP S10)-X-(GFP S11) (FIG. 17). This species complements a third domain of GFP, GFP 1-9 OPT to produce intact GFP. We engineered the construct (GFP S10)-L1-X-L2-(GFP S11) using methods well-known in the art, where L1 and L2 are linkers each consisting of amino acids GGGS [SEQ ID NO: 44] by inserting test proteins between GFP S10 and GFP S11 in the superfolder GFP S10-11 tag (FIG. 18A). We successfully detected (GFP S10)-L1-sulfite reductase-L2-(GFP S11) using GFP 1-9 OPT, although the complementation was only ca. 1/30 as efficient as the C-terminal GFP S11 M3+GFP 1-10 OPT format. We also discovered that other partially soluble proteins became insoluble when expressed in this sandwich format. First we improved the complementation efficiency without regard to solubility. We started with a DNA construct coding for (GFP S10)-L1-NdeI::GGGSGSGG::BamHI-L2-(GFP S11), where the strands GFP S10 and GFP S11 are derived from superfolder GFP (FIG. 18A), and the short amino acid sequence GGGSGSGG [SEQ ID NO: 54] provides a flexible linker between the two GFP strands. This was mutated by DNA shuffling and libraries of variants with improved complementation with GFP 1-10 OPT were screened in-vivo by sequential induction of the library from the pTET vector, followed by expression of the GFP 1-9 OPT from the pET vector within E. coli cells as colonies on plates (following methods outlined in EXAMPLE 4, supra). Six of the brightest clones were sequenced after three rounds of evolution (FIG. 18A). We focused on the fifth mutant of the set of six, and this construct was termed (GFP S10 SM5)-L1-X-L2-(GFP S11 SM5) (SM5=sandwich mutant number 5). This optimum has the sequence YTMDLPDNHYL- STQTILLKDLNGTGVGSGGGSHMGGGSGSGGGSGG GSTSEKRDHMVLLEYVTAAGITDAS*, [SEQ ID NO: 27], where the GFP S10 and GFP S11 strands are underlined, and the asterisk is the stop codon. The first italic sequence is derived from the NdeI cloning site CATATG, coding for amino acids HM. The second italic sequence is derived from the BamHI restriction site GGATCC, coding for the amino acids GS. Test proteins with in-frame NdeI and BamHI restriction sites are cloned into a vector containing the construct previously digested by NdeI and BamHI restriction enzymes using methods well-known in the art. Typically the in-frame region between the NdeI and BamHI site in a cloning cassette containing the construct would be replaced by a frame-shift stuffer with stop codons, to prevent false-positives caused by undigested vector or relegated vector (see EXAMPLE 1, supra, for representative frame-shift stuffer sequences). Such approaches are well-known in the art. The cassette is flanked by NcoI and XhoI restriction sites for cloning into the pTET vector. Although the complementation rate had increased ca. 20-fold with soluble sulfite reductase cloned into the Nde-1/BamH-1 site compared to the starting strand construct, the deleterious effect on protein solubility had also increased when tested with partially soluble HPS protein (as in EXAMPLE 4, supra). Next, to simultaneously select for improved complementation and decreased perturbation of fusion protein solubility, we used the same bait protein hexulose phosphate synthase, HPS, that we had used to improve the solubility and complementation of GFP S11 (EXAMPLE 4, supra). HPS was ca. 60% soluble expressed alone from the pTET vector (protein #9, FIG. 15), but insoluble expressed as (GFP S10 SM5)-L1-HPS-L2-(GFP S11 SM5) fusion protein. We focused on the upstream (GFP S10 SM5) domain, using shuffling and primer doping mutagenesis where a pool of fourteen synthetic oligonucleotide primers (FIG. 18B). Each primer was centered at one of the fourteen amino acids of the GFP S10 SM5 domain, containing an NNN coding degeneracy the central target amino acid and flanking homology to the GFP S10 SM5 in the context of the cloning vector (target sequence shown in FIG. 18B and FIG. 19). The pool of degenerate primers was added to the fragmented DNA during the reassembly reaction (reassembly performed as in EXAMPLE 4, supra). Such primer-doping mutagenesis techniques are well-known in the art. We shuffled and amplified the domain flanked by NcoI upstream and BamHI downstream, Nco1:(GFP S10 SM5)-L1-Nde-1:: HPS::BamHI-L2-(GFP S11 SM5), adding the degenerate primer mix during reassembly of the fragments by polymerase chain reaction (PCR). We reamplified the domain from the reassembled mutated construct by PCR, then digested out the Nco1/Nde-1 fragment containing the mutated (GFP S10) pool, gel purified it using standard techniques, and cloned it into the receiving vector containing Nco1//NdeI::HPS::BamHI-L2-(GFP S11 SM5). After three rounds of selection using the sequential induction format from the pTET and pET plasmids (this example, supra, and following the methods outlined in EXAMPLE 4, supra for in vitro complementation assays using the immediate fragments in this example) the sequence of each of the best eight clones was determined by fluorescent dye terminator sequencing (FIG. 19). The best-performing clone, termed (GFP S10 A10)-L1-NdeI::HPS::BamHI-L2-(GFP S11 SM5) was ca. 45% soluble expressed in *E. coli*, a marked improvement relative to the starting construct which was insoluble, and complementation signal was now ca. ⅕ to ¼ that of the complementation using GFP 1-10 OPT to detect only the GFP S11 SM5 tag in the sandwich construct (supra). Next we tested the assay using the eighteen *Pyrobaculum* test proteins (see Table 3 supra, for identity and non-fusion solubility). Soluble and pellet fractions were assayed as previously described (EXAMPLE 9, supra) using the immediate fragments of the current example. We assayed these sandwich-format tagged proteins using GFP 1-10 OPT to specifically detect only the (GFP S11 SM5) tag as a reference, and also used GFP 1-9 OPT, which required the binding of both (GFP S10 A10) and (GFP S11 SM5) strands of the sandwich format tagged proteins. As expected, complementation was more efficient when only one strand was needed for detection (GFP 1-10 OPT case), and the detection of the pellet fraction using the urea-solubilized pellets was most efficient for the GFP 1-10 OPT detection case (FIG. 20). Nonetheless, soluble fraction fluorescence for the sandwich detected using GFP 1-9 OPT was well-correlated with the signal using the GFP 1-10 detection, reporting soluble protein as expected. Similarly, in vivo sequential induction was correlated with soluble pTET expression with GFP S11 M3 fusions (FIG. 20, see also EXAMPLE 9 supra and FIG. 15). The preferred optimum has the amino acid sequence YTMDLP DDHYLSTQTILSKDLNGTDVGSGGGSHMGGGSGSG-GGSGGGSTSEKRDHMVLLEYVTAAGITDAS*, [SEQ ID NO: 28], where the GFP S10 and GFP S11 strands are underlined, and the asterisk is the stop codon. The first italic sequence is derived from the NdeI cloning site CATATG, coding for amino acids HM. The second italic sequence is derived from the BamHI restriction site GGATCC, coding for the amino acids GS. Test proteins with in-frame NdeI and BamHI restriction sites are cloned into a vector containing the construct previously digested by NdeI and BamHI restriction enzymes using methods well-known in the art. The cassette is flanked by NcoI and XhoI restriction sites for cloning into the pTET vector. Typically the in-frame region between the NdeI and BamHI site in a cloning cassette containing the construct would be replaced by a frame-shift stuffer with stop codons, to prevent false-positives caused by undigested vector (see EXAMPLE 1, supra, for representative frame-shift stuffer sequences).

Example 13

Figure 21:
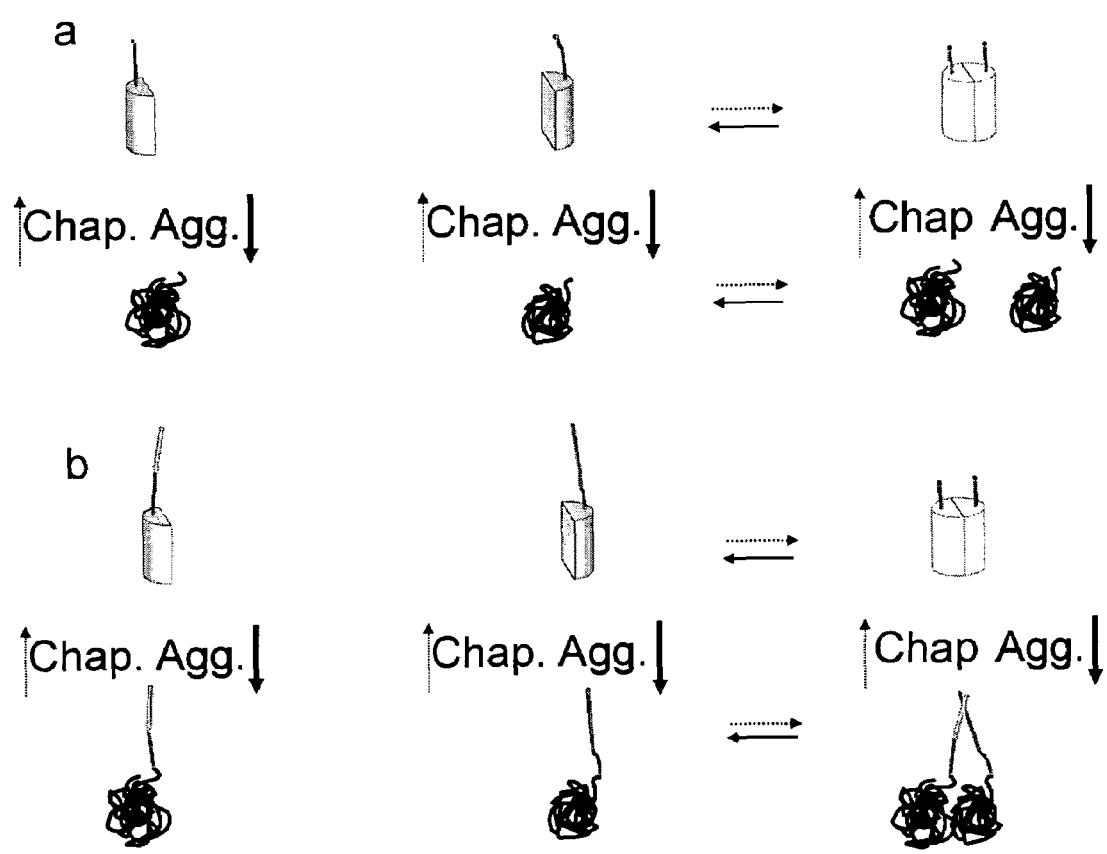
FIG. 21 shows a two-body split GFP complementation during co-expression of GFP fragments, using conventional, poorly-folded GFP fragments. Most of the protein is aggregated (Agg. Pathway) and a small amount of the misfolded protein is rescued and rendered transiently soluble by chaperones (Chap. Pathway). In (a), there are no interacting protein domains, and so very little of the protein can complement by the chaperone-mediated pathway, since the fragments are not held together by interacting domains, after a given fragment is solubilized by chaperones, it is unlikely to interact with a second recently-refolded fragment. The untethered fragments are likely to re-aggregate after release from the chaperones before they can interact productively. In (b), adding interacting domains can increase the amount of complemented protein by holding the fragments in proximity while they are refolded by chaperones, increasing the probability that the fragments will find each other while transiently solubilized by chaperones. Thus existing poorly-folded GFP fragments appear to require interacting domains for formation of fluorescence, even though most of the protein is misfolded and aggregated.

Model of Operation of Existing Protein-Protein Interaction Detection Systems Using Co-Expression of Split GFP Fragment Reconstitution Conventional split GFP systems are poorly folded and mostly insoluble. Much of the fragment(s) partition into aggregates. A small amount is rescued by chaperone activity, but in the absence of interacting domains, the probability that rescued transiently-soluble fragments can bind prior to repartitioning into aggregates is low (FIG. 21 *a*). Adding interacting domains can tether the fragments, increasing the probability of interaction of the newly-refolded transiently soluble fragments (FIG. 21 *b*). Thus this system appears to not spontaneously complement not for entropic reasons, but rather because of a lack of stability.

Example 14

Figure 22:
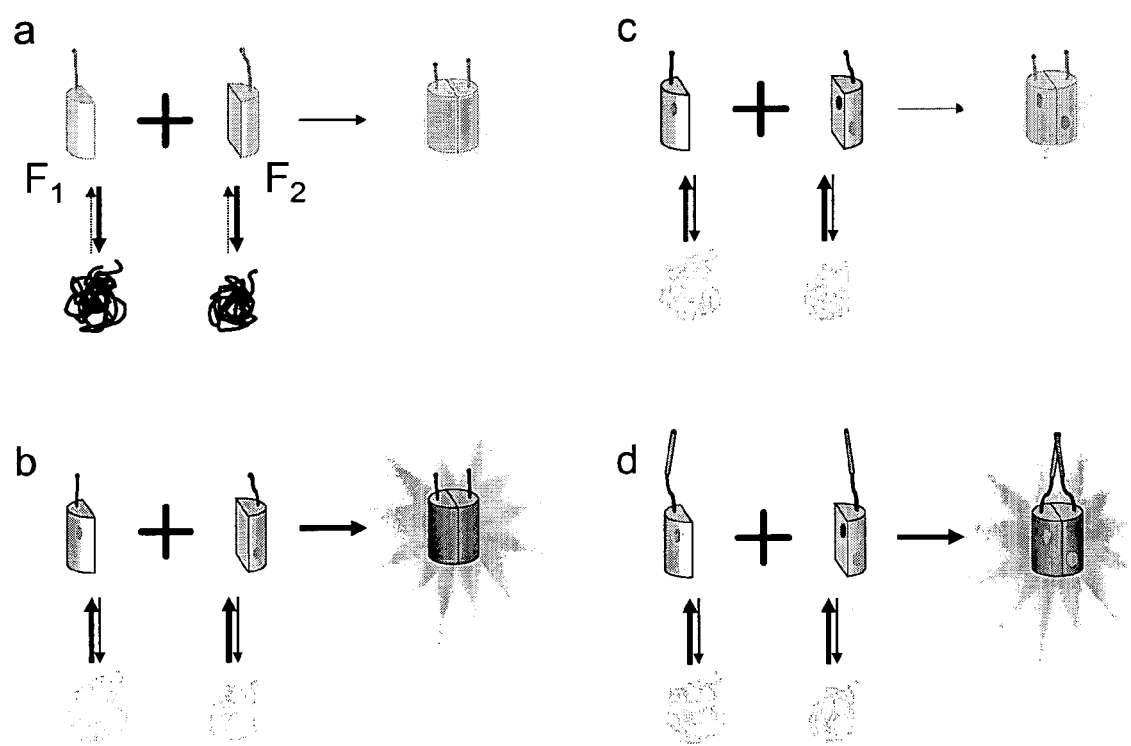
FIG. 22 shows a two-body split GFP complementation during sequential expression of GFP fragments, or expression in distinct separate compartments, using conventional, poorly-folded GFP fragments. As in FIG. 21, most of the protein is aggregated (Agg. Pathway) and a small amount of the misfolded protein is rescued and rendered transiently soluble by chaperones (Chap. Pathway). In (a), there are no interacting protein domains, and so very little of the protein can complement by the chaperone-mediated pathway, since the fragments are not held together by interacting domains, after a given fragment is solubilized by chaperones, it is unlikely to interact with a second recently-refolded fragment. The untethered fragments are likely to re-aggregate after release from the chaperones before they can interact productively. In (b), even adding interacting domains fails to increase the amount of complemented protein, since the fragments are not simultaneously expressed or are expressed in different compartments, drastically reducing the probability that the fragments will find each other while transiently solubilized by chaperones, even with interacting domains. Thus existing poorly-folded GFP fragments, even when fused with interacting domains, fail to complement when not expressed simultaneously or co-refolded.

Model of Operation of Existing Protein-Protein Interaction Detection Systems Using Separately Expressed Split GFP Fragment Reconstitution Even with fused interacting domains, conventional split GFP systems fail to efficiently complement when separately expressed (temporally or spatially). Since the fragments are not simultaneously expressed, the probability of interaction of the newly-refolded transiently soluble fragments is very low (FIG. 22). Thus this system appears to not spontaneously complement not for entropic reasons, but rather because of a lack of stability, even with fused interacting domains. This is consistent with the observation by Zhang and Chalfie, 2004, supra that GFP fragments with fused interacting coiled-coils were capable of complementation only when co-expressed, and Hu et. al 2003 supra observed complementation of coiled-coil fused GFP fragments only when co-refolded from inclusion bodies or co-expressed Hu, C. D. & Kerppola, T. K., 2003, *Simultaneous visualization of multiple protein interactions in living cells using multicolor fluorescence complementation analysis*. Nat Biotechnol 21, 539-545.

Example 15

Figure 23:
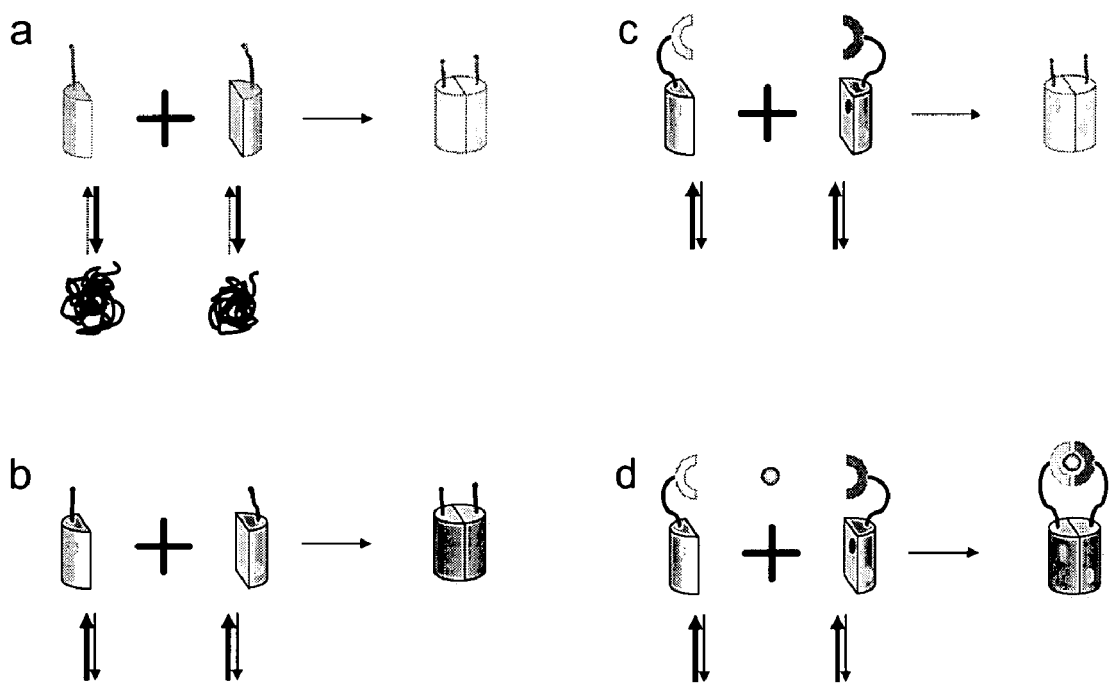
FIG. 23 shows a strategy for discovering soluble, non-perturbing GFP fragments that also require interacting domains for reconstitution and folding. (a) existing GFP fragments F1 and F2 are poorly folded and fail to complement. (b) F1 and F2 are engineered by directed evolution to discover better-folded versions that remain soluble, do not aggregate, and do not perturb fusion protein folding and solubility, and thus are capable of spontaneous association. These mutations are shown by white dots. In (c), additional mutations are discovered that reduce or eliminate spontaneous association (black dots). A large pool of variants that are no longer fluorescent are isolated from cells by flow cytometry or screening on plates. (d) These variants are subcloned into vectors and expressed with fused known interacting protein domains (such as coiled-coils) can be used to discover that subset of the non-fluorescent mutants that bind and fold to become fluorescent only when fused to interacting domains. This eliminates the false negatives in step (c) that are misfolded or incapable of complementation even in the presence of fused domains.

Engineering Soluble, Non-Perturbing Split Fluorescent Protein Fragments Requiring Interacting Domains for Reconsistution Previously-described split GFP fragments were poorly folded, aggregated, and thus did not efficiently complement (FIG. 23 *a*). The above examples (EXAMPLES 1-12) demonstrate techniques and approaches for engineering soluble, stable GFP fragments that remain soluble and do not aggregate (FIG. 23 *b*). These fragments can be expressed simultaneously or separately, and remain soluble, and do not perturb the solubility and folding of fused polypeptides. This is a key requirement for a generally useful protein-protein interaction detection system based on protein fragment reconstitution. However, these fragments self-associate without the need for fused interacting domains (FIG. 23 *b*). To be useful as protein-protein interaction detectors, the fragments must require fused interacting domains for reconstitution. In one approach, soluble engineered fragment F1 is held constant and used as an assay fragment to screen a library of variants of fragment F2 to identify mutations of F2 which eliminate or abrogate spontaneous complementation and formation of fluorescence. A large library can be screened in *E. coli*, for example, using flow cytometry to find and collect a large number of variants (i.e., >$10^5$) that are non-fluorescent (FIG. 23 *c*). These non-fluorescent variants can include undesirable variants such as those mutants that have folding defects, are incapable of complementation even with fused interacting domains, are insoluble etc. Thus the library of non-fluorescent variants is then subcloned into vector that causes the mutants to be expressed as fusions with a known interacting protein, such as a coiled-coil (such coiled coils are described in Hu, 2002, supra; Ghosh et al, 2000, supra.). The library is again screened by flow cytometry or on plates to identify those mutants that now complement when fused only to interacting proteins. If necessary, the final library of optima can now be subcloned into vectors without interacting proteins to verify the dependence on fused interacting domains for complementation. Further rounds of mutation to further improve fragment stability and solubility can be performed if required as in EXAMPLE 3 and EXAMPLE 4, above. Furthermore, bait proteins that have reduced solubility when fused to suboptimal aggregation-prone GFP fragments can be incorporated into the fusions of this current example (EXAMPLE 15) to maintain stringent selection for solubility during screens for mutations that eliminate spontaneous association. Furthermore, the amino acids specifically involved in the interface between the interacting GFP fragments can be targeted for increased levels of mutagenesis relative to the scaffolding as a whole using primer-directed mutagenesis (degenerate oligo doping), methods well known in the art (see DEFIINITIONS, methods of mutagenesis, supra), thereby increasing the likelihood that the interaction between the GFP fragments can be reduced without adversely affecting the folding of the GFP fragments. The interface amino acids of GFP can be easily identified by inspection of the three-dimensional structure (Yang, 1996, supra), see also the topological diagram FIG. 3.

Example 16

Engineering Soluble, Non-Perturbing Split Fluorescent Protein Fragments Requiring Interacting Domains for Reconsistution, Using Fused Protein Domains Whose Interaction is Inducible by a Small Molecule Effector This is example is analogous to EXAMPLE 15, above, except that the interaction of the fused protein domains is inducible, for example, the FKB12 and FRB, two proteins whose interaction can be induced by the addition of rapamycin, as in Mootz & Muir, 2002, *Protein splicing triggered by a small molecule* J. Am. Chem. Soc. 124: 9044-9045, Standaert et al. 1990, Molecular cloning and overexpression of the human FK506-binding protein FKBP, Nature 346: 671-674; Chen et al., 1995, Identification of an 11-kDa FKBP12-rapamycin-binding domain within the 289-kDa FKBP12-rapamycin-associated protein and characterization of a critical serine residue, Biochemistry 92: 4947-4951. Thus in FIG. 24 *c*, mutants of F2 that eliminate spontaneous complementation can be screened for in the absence of the effector (rapamycin, in this example), then those that successfully complement when fused to interacting domains can be identified by adding the effector as in FIG. 24 *d*.

Example 17

Three Body Complementation

Figure 25:
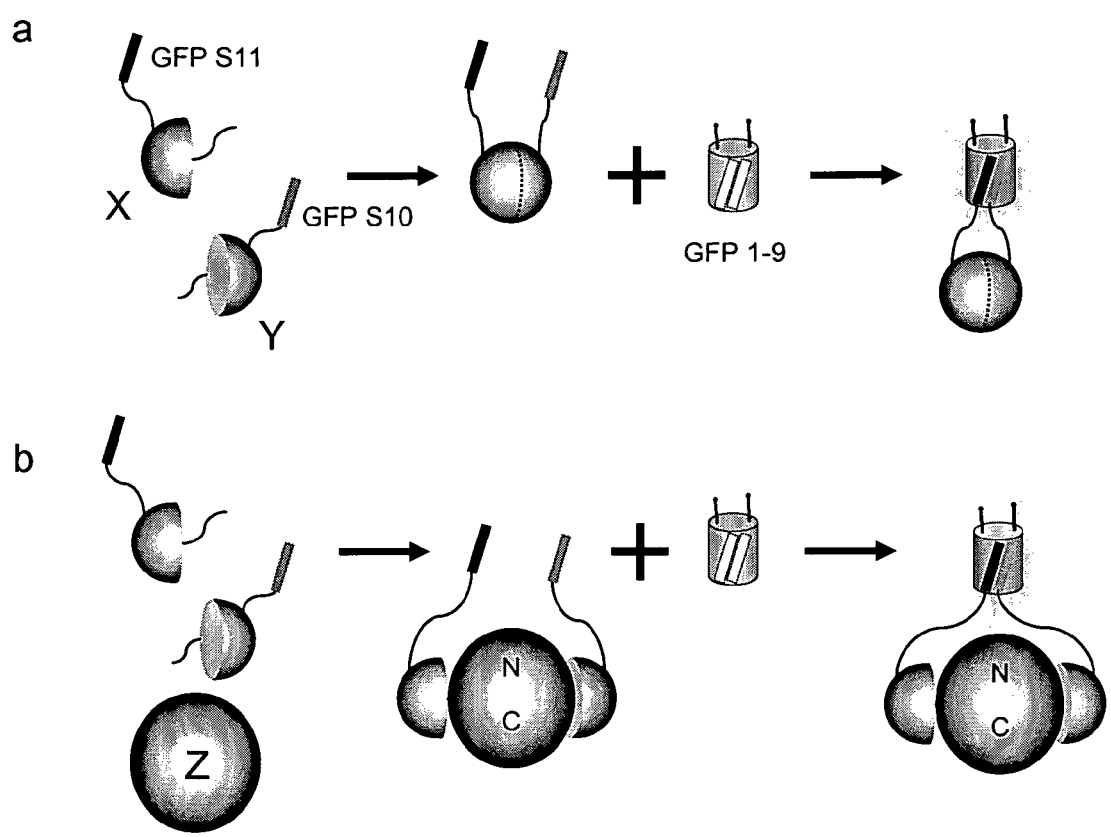
FIG. 25 shows the three-body complementation strategy. In (a) when GFP S11 and GFP s10 are tethered on a domain X, they can spontaneously bind and complement with GFP s1-9. In (b), GFP s11 and GFP s10 are not tethered, and the entropy is too high for efficient complementation.

GFP s10 and GFP s11 are fused to a test protein X. Contacting these species with the assay strand GFP s1-9 results in the complementation of the GFP S10 and GFP S11 strands with GFP s1-9, thereby indicating that X is soluble, and that GFP s10 and GFP s11 are tethered on X (FIG. 25 *a*). If GFP s10 and GFP s11 are not tethered, as in FIG. 25 *b*, the entropy is too high to allow complementation with GFP s1-9.

Example 18

Detection of Interaction of Two Proteins

GFP s10 is fused to a test protein X as GFP s10-X or X-GFP s10. GFP s11 is fused to a test protein Y as GFP s11-Y or Y-GFP S11. The alternative configuration GFP s10-Y, Y-GFP s10 or GFP s11-X, X-GFP s11 could be used. The fusion proteins are expressed within a cell, cellular compartment, or in vitro and caused to contact one another. If X and Y interact and bind with one another, they cause the tethering of GFP s10 and GFP s11, reducing the configurational entropy of the GFP s10 and GFP s11 (FIG. 26 *a*). Contacting these species with the assay strand GFP s1-9 results in the complementation of the GFP s10 and GFP S11 strands with GFP 1-9, thereby forming the fluorescent chromophore, indicating that X and Y interact. If X and Y do not interact, then GFP s10 and GFP S11 are not tethered, the complementation of the GFP s1-9 assay fragment inefficient, resulting in weak or no fluorescence complementation. Examples of interacting proteins X and Y include coiled-coils, antibodies and their cognate peptide or protein antigens or binding partners, proteins that form heteromultimers.

Example 19

Detection of Interaction of Two Proteins with a Third Protein

GFP s10 is fused to a test protein X as GFP s10-X or X-GFP s10. GFP s11 is fused to a test protein Y as GFP s11-Y or Y-GFP s11. The alternative configuration GFP s10-Y, Y-GFP s10 or GFP s11-X, X-GFP s11 could be used. The fusion proteins are expressed within a cell, cellular compartment, or in vitro and caused to contact one another. X and Y do not spontaneously interact or bind each other. If X and Y interact and bind with a third protein Z, adding Z causes the binding of X and Y, the tethering of GFP s10 and GFP s11, reducing the configurational entropy of the GFP s10 and GFP s11 (FIG. 26 b). Contacting these species with the assay strand GFP s1-9 results in the complementation of the GFP s10 and GFP s11 strands with GFP 1-9, thereby forming the fluorescent chromophore, indicating that X and Y interact with Z and Z is present. If X and Y do not interact with Z, or Z is absent, then GFP s10 and GFP s11 are not tethered, the complementation of the GFP s1-9 assay fragment inefficient, resulting in weak or no fluorescence complementation. Examples of proteins X and Y that interact with Z could include hetero or homomeric tribrid coiled-coils, pairs of antibodies (X and Y) binding with an antigen (Z) and their cognate peptide or protein antigens or binding partners, proteins that form heteromultimers.

Example 20

Detection of Interaction of Two Proteins with a Small Effector Molecule

GFP s10 is fused to a test protein X as GFP s10-X or X-GFP s10. GFP s11 is fused to a test protein Y as GFP s11-Y or Y-GFP s11. The alternative configuration GFP s10-Y, Y-GFP s10 or GFP s11-X, X-GFP s11 could be used. The fusion proteins are expressed within a cell, cellular compartment, or in vitro and caused to contact one another. X and Y do not spontaneously interact or bind each other. If X and Y interact and bind with a small effector molecule, adding the effector causes the binding of X and Y, the tethering of GFP s10 and GFP s11, reducing the configurational entropy of the GFP s10 and GFP s11 (FIG. 27 b). Contacting these species with the assay strand GFP s1-9 results in the complementation of the GFP s10 and GFP s11 strands with GFP 1-9, thereby forming the fluorescent chromophore, indicating that X and Y interact with the effector and the effector is present. If X and Y do not interact with the effector, or the effector is absent, then GFP s10 and GFP S11 are not tethered, the complementation of the GFP s1-9 assay fragment inefficient, resulting in weak or no fluorescence complementation (FIG. 27 b). Examples of proteins X and Y that interact with effector could include FKBP and FRB, for example, as in Mootz & Muir, 2002, *Protein splicing triggered by a small molecule* J. Am. Chem. Soc. 124: 9044-9045, Standaert et al. 1990, Molecular cloning and overexpression of the human FK506-binding protein FKBP, Nature 346: 671-674; Chen et al., 1995, Identification of an 11-kDa FKBP12-rapamycin-binding domain within the 289-kDa FKBP12-rapamycin-associated protein and characterization of a critical serine residue, Biochemistry 92: 4947-4951. Various two-component systems that sense small molecules could also be used.

Example 21

Identifying Interacting Partners Using a Random Genetic Screen

GFP s10 is fused to a test protein X as GFP s10-X or X-GFP s10. A random library YLIB containing potential interactors with X is expressed as a fusion with GFP s11 as YLIB-GFP s11 or GFP s11-YLIB. The alternative configuration of GFP s10-Y, Y-GFP s10 or GFP s11-X, X-GFP s11 could be used. The proteins are expressed within a cellular compartment, cell or cell-free extracts and made to contact one another, such that single member i of YLIB i.e. YLIBi-GFP s11 or GFP s11-YLIBi is made to interact with GFP s10-X or X-GFP s10. If X and YLIBi interact and bind with one another, they cause the tethering of GFP s10 and GFP s11, reducing the configurational entropy of the fused GFP s10 and GFP s11. Contacting these species with the assay strand GFP s1-9 results in the complementation of the GFP s10 and GFP s11 strands with GFP s1-9, thereby forming the fluorescent chromophore, indicating that X and YLIBi interact. If X and YLIBi do not interact, then GFP s10 and GFP s11 are not tethered, making the complementation of the GFP s1-9 assay fragment inefficient, resulting in weak or no fluorescence complementation.

Example 22

Identifying Interacting Folding Partners Using a Random Genetic Screen

X is part of an obligatory folding pair comprised of X and Y in which co-expression of X and Y within the same compartment results in the proper folding of X by virtue of contact with and co-folding with Y. Subsequently X and Y form a soluble correctly-folded heterodimer comprised of X and Y, in which X and Y remain associated with each other. In the absence of Y, X misfolds and forms aggregates. GFP 10 is fused to a test protein X as GFP S10-X or X-GFP S10. Protein X folds poorly when expressed by itself, causing GFP S10-X or X-GFP S10 to be sequestered in aggregates. To discover a folding partner Y which rescues the folding of X, a random library YLIB containing potential interacting folding partners with X is expressed as a fusion with GFP S11 as YLIB-GFP S11 or GFP S11-YLIB. It is obvious that the alternative configuration of GFP S10-Y, Y-GFP S10 or GFP S11-X, X-GFP S11 could be used. The proteins are expressed within a cellular compartment, cell or cell-free extracts and made to contact one another, such that single member i of YLIB i.e. YLIBi-GFP S11 or GFP S11-YLIBi is made to contact GFP S10-X or X-GFP S10. If X and YLIBi interact, co-fold, and bind with one another, they result in a correctly folded, soluble heterodimer resulting in the tethering of GFP S10 and GFP S10, reducing the configurational entropy of the fused GFP S10 and GFP S11. Subsequently contacting these associated fusion species with the assay strand GFP 1-9 results in the complementation of the GFP S10 and GFP S11 strands with GFP 1-9, thereby forming the fluorescent chromophore, indicating that X and YLIBi interact. If X and YLIBi do not form interacting associated folding partners, then GFP S10 and GFP S11 are not tethered, making the complementation of the GFP 1-9 assay fragment inefficient, resulting in weak or no fluorescence complementation. If the fusion proteins X and Y are expressed under the control of the tet promoter for example, and the GFP 1-9 assay fragment is expressed under the control of an independently-inducible promoter, such as the IPTG-inducible T7 promoter, then the order of expression of X, Y and GFP 1-9 can be independently regulated. If the GFP 1-9 assay fragment is simultaneously expressed with the X and YLIB fusion proteins, then the interaction of X and Y can be detected regardless of the solubility of X and Y. If the GFP 1-9 assay fragment is expressed after the X and Y, then only associated interacting X and Y proteins that are also soluble will be detected. This solubility reporter aspect dependent on sequential induction has been previously demonstrated using X-GFP S10-S11 and GFP 1-9, as well as GFP S10-X-GFP S11 and GFP 1-9.

Example 23

Identifying Interacting Partners Using a Random Genetic Screen

GFP 10 is fused to a test protein X as GFP S10-X or X-GFP S10. A random library YLIB containing potential interactors with X is expressed as a fusion with GFP S11 as YLIB-GFP S11 or GFP S11-YLIB. It is obvious that the alternative configuration of GFP S10-Y, Y-GFP S10 or GFP S11-X, X-GFP S11 could be used. The proteins are expressed within a cellular compartment, cell or cell-free extracts and made to contact one another, such that single member i of YLIB i.e. YLIBi-GFP S11 or GFP S11-YLIBi is made to interact with GFP S10-X or X-GFP S10. If X and YLIBi interact and bind with one another, they cause the tethering of GFP S10 and GFP S11, reducing the configurational entropy of the fused GFP S10 and GFP S11. Contacting these species with the assay strand GFP 1-9 results in the complementation of the GFP S10 and GFP S11 strands with GFP 1-9, thereby forming the fluorescent chromophore, indicating that X and YLIBi interact. If X and YLIBi do not interact, then GFP S10 and GFP S11 are not tethered, making the complementation of the GFP 1-9 assay fragment inefficient, resulting in weak or no fluorescence complementation.

Example 24

Identifying Interacting Folding Partners Using a Random Genetic Screen

X is part of an obligatory folding pair comprised of X and Y in which co-expression of X and Y within the same compartment results in the proper folding of X by virtue of contact with and co-folding with Y. Subsequently X and Y form a soluble correctly-folded heterodimer comprised of X and Y, in which X and Y remain associated with each other. In the absence of Y, X misfolds and forms aggregates. GFP 10 is fused to a test protein X as GFP S10-X or X-GFP S10. Protein X folds poorly when expressed by itself, causing GFP S10-X or X-GFP S10 to be sequestered in aggregates. To discover a folding partner Y which rescues the folding of X, a random library YLIB containing potential interacting folding partners with X is expressed as a fusion with GFP S11 as YLIB-GFP S11 or GFP S11-YLIB. It is obvious that the alternative configuration of GFP S10-Y, Y-GFP S10 or GFP S11-X, X-GFP S11 could be used. The proteins are expressed within a cellular compartment, cell or cell-free extracts and made to contact one another, such that single member i of YLIB i.e. YLIBi-GFP S11 or GFP S11-YLIBi is made to contact GFP S10-X or X-GFP S10. If X and YLIBi interact, co-fold, and bind with one another, they result in a correctly folded, soluble heterodimer resulting in the tethering of GFP S10 and GFP S11, reducing the configurational entropy of the fused GFP S10 and GFP S11. Subsequently contacting these associated fusion species with the assay strand GFP 1-9 results in the complementation of the GFP S10 and GFP S11 strands with GFP 1-9, thereby forming the fluorescent chromophore, indicating that X and YLIBi interact. If X and YLIBi do not form interacting associated folding partners, then GFP S10 and GFP S11 are not tethered, making the complementation of the GFP 1-9 assay fragment inefficient, resulting in weak or no fluorescence complementation. If the fusion proteins X and Y are expressed under the control of the tet promoter for example, and the GFP 1-9 assay fragment is expressed under the control of an independently-inducible promoter, such as the IPTG-inducible T7 promoter, then the order of expression of X, Y and GFP 1-9 can be independently regulated. If the GFP 1-9 assay fragment is simultaneously expressed with the X and YLIB fusion proteins, then the interaction of X and Y can be detected regardless of the solubility of X and Y. If the GFP 1-9 assay fragment is expressed after the X and Y, then only associated interacting X and Y proteins that are also soluble will be detected. This solubility reporter aspect dependent on sequential induction has been previously demonstrated using X-GFP S10-S11 and GFP 1-9, as well as GFP S10-X-GFP S11 and GFP 1-9.

Example 25

Monitoring Protein Interactions in the Presence of Effectors

GFP 10 is fused to a test protein X as GFP S10-X or X-GFP S10. GFP 11 is fused to a test protein Y as GFP S11-Y or Y-GFP S11. The alternative configuration of GFP S10-Y, Y-GFP S10 or GFP S11-X, X-GFP S11 could be used. The interaction efficiency of the X and Y domains of the fusion proteins is first assessed in the absence of an effector molecule E using the assay fragment GFP 1-9, and the fluorescence recorded. The effector molecule E, can be a small molecule such as a drug, hormone, or peptide, or a large molecule such as a protein or macromolecular complex. Next the effector molecule E is made to contact the fusion proteins, and the efficiency of the interaction of the domains X and Y of the fusion proteins is assessed using the complementation with GFP 1-9. If E increases the interaction of X and Y, the fluorescence will be brighter than in the absence of E. If E decreases the interaction of X and Y, the fluorescence will be fainter than in the absence of E. If E is neutral or has no effect on the interaction of X and Y, the fluorescence will be the same as in the absence of E.

Example 26

Identifying Potential Effector Proteins Capable of Effecting Protein Interactions Using a Random Genetic Screen GFP 10 is fused to a test protein X as GFP S10-X or X-GFP S10. GFP 11 is fused to a test protein Y as GFP S11-Y or Y-GFP S11. The alternative configuration of GFP S10-Y, Y-GFP S10 or GFP S11-X, X-GFP S11 could be used. The interaction efficiency of the X and Y domains of the fusion proteins is first assessed in the absence of an effector molecule E using the assay fragment GFP 1-9, and the fluorescence recorded. In this example the effector molecule E is a genetically-encoded peptide, protein or macromolecular complex. A random library ELIB containing potential effectors of the interaction of X and Y is expressed within the same compartment as the X and Y fusion proteins. The proteins are can be expressed within a cellular compartment, cell or cell-free extracts and made to contact one another, such that single member i of ELIB, i.e. ELIBi, is contacted with the X and Y fusion proteins. To measure the strength of the interaction of X and Y in the fusion proteins, these species are made to contact the assay fragment GFP 1-9. If E increases the interaction of X and Y, the tethering of the fused GFP S10 and GFP S11 domains will be increased, and the fluorescence will be brighter than in the absence of ELIBi, thereby indicating that ELIBi enhances the interaction of X and Y. On the other hand, if ELIBi decreases the interaction of X and Y, the fluorescence will be fainter than in the absence of ELIBi, thereby indicating that ELIBi decreases the interaction of X and Y. If ELIBi is neutral or has no effect on the interaction of X and Y, the fluorescence will be the same as in the absence of ELIBi, indicating that ELIBi has no effect on the interaction of X and Y.

Example 27

Organelle Painting For Detecting Organelle-Specific Protein Interactions

This is analogous to the EXAMPLE 18 and EXAMPLE 21, supra, except that the assay fragment GFP 1-9 is directed to a specific cellular compartment using a localization tag. Interactions occurring within a specific compartment are thus specifically detected by sending GFP 1-9 to that compartment. GFP 10 is fused to a test protein X as GFP S10-X or X-GFP S10. A random library YLIB containing potential interactors with X is expressed as a fusion with GFP S11 as YLIB-GFP S11 or GFP S11-YLIB. The alternative configuration of GFP S10-Y, Y-GFP S10 or GFP S11-X, X-GFP S11 could be used. The proteins are expressed within a cellular compartment, cell or cell-free extracts and made to contact one another, such that single member i of YLIB i.e. YLIBi-GFP S11 or GFP S1-YLIBi is made to interact with GFP S10-X or X-GFP S10. If X and YLIBi interact and bind with one another, they cause the tethering of GFP S10 and GFP S11, reducing the configurational entropy of the fused GFP S10 and GFP S11. To determine if the interaction occurs within a specific compartment C, GFP 1-9 is fused with a localization tag T directing the localization of T-GFP 1-9 or GFP 1-9-T to compartment C. If X and Y interact in compartment C, then when T-GFP 1-9 or GFP 1-9-T is directed to compartment C, compartment C will become fluorescent by virtue of contacting the fusion species of X and Y with the assay strand T-GFP 1-9 or GFP 1-9-T, resulting in the complementation of the GFP S10 and GFP S11 strands with GFP 1-9, thereby forming the fluorescent chromophore, indicating that X and YLIBi interact in compartment C. If X and YLIBi do not interact in compartment C, then GFP S10 and GFP S11 are not tethered within compartment C, making the complementation of the T-GFP 1-9 or GFP 1-9-T assay fragment inefficient, resulting in weak or no fluorescence complementation in compartment C. Multiple compartments can be tagged with different colors of GFP 1-9, allowing more than one compartment to be monitored for potential interacting proteins X and Y fused with GFP S-10 and GFP S-11. For example, a cyan variant of GFP 1-9 containing the Y66W cyan mutation could be targeted to the golgi using a known golgi-targeting fusion signal. Concurrently, a green version of GFP 1-9 containing Y66 could be targeted to the mitochondria using a fusing mitochondrial targeting domain. Monitoring the amount of cyan and green fluorescence would report the amount of protein interaction of X and Y occurring within the golgi and mitochondria, respectively.

Example 28

Organelle Painting for Detecting Effector-Mediated Organelle-Specific Protein Interactions This is related to EXAMPLE 20 and EXAMPLE 25, above in which spectrally-distinct variants of GFP 1-9 are directed to one or more specific cellular compartments using localization tags. Interactions between proteins X and Y each labeled with GFP-S10 and GFP-S11 occurring within a specific compartment is specifically detected by virtue of the spectral signature of the GFP 1-9 directed to that compartment. The interaction efficiency of the X and Y domains of the fusion proteins within each compartment is first assessed in the absence of an effector molecule E using the assay fragment GFP 1-9, and the fluorescence recorded for each spectral variant of GFP 1-9. The effector molecule E, can be a small molecule such as a drug, hormone, or peptide, or a large molecule such as a protein or macromolecular complex. Next the effector molecule E is made to contact cell or compartment in which the assay is carried out, and the efficiency of the interaction of the domains X and Y of the fusion proteins is assessed for each spectrally-distinct version of GFP 1-9 targeted to the cellular compartments. If E increases the interaction of X and Y within a designated cellular compartment, the fluorescence of that compartment will be brighter than in the absence of E. If E decreases the interaction of X and Y, the fluorescence of that compartment will be fainter than in the absence of E. If E is neutral or has no effect on the interaction of X and Y, the fluorescence of that compartment will be the same as in the absence of E. The efficiency of complementation within each targeted compartment is assessed by monitoring the fluorescence signature of the GFP 1-9 variant targeted to that compartment. For example, X and Y could be proteins known to interact within the golgi and the mitochondria. Cyan GFP 1-9 could be targeted to the golgi, and green GFP 1-9 could be targeted to the mitochondria. A variety of effector drugs could be tested for those that increase complementation of X and Y within the golgi relative to the mitochondria. Drugs with the desired effect would thus increase complementation in the golgi, resulting in an enhanced cyan fluorescence to green fluorescence ratio, relative to drugs that had no effect or decreased the complementation of X and Y within the golgi relative to the mitochondria. The alternative configuration of GFP S10-Y, Y-GFP S10 or GFP S11-X, X-GFP S11 could be used.

Example 29

Engineering Binding Ligand-Antigen Interactions

This example is functionally analogous to EXAMPLE 18 and EXAMPLE 19. GFP 10 is fused to a binding ligand B, such as an antibody, as a fusion construct GFP S10-B or B-GFP S10. GFP 11 is fused to a test protein antigen A as GFP S11-A or A-GFP S11. It is obvious that the alternative configuration of GFP S10-A, A-GFP S10 or GFP S11-B, B-GFP S11 could be used. The fusion proteins are expressed within a cell, cellular compartment, or in vitro and caused to contact one another. If antibody or binding ligand B and antigen A interact and bind with one another, they cause the tethering of GFP S10 and GFP S11, reducing the configurational entropy of the GFP S10 and GFP S11. Contacting these species with the assay strand GFP 1-9 results in the complementation of the GFP S10 and GFP S11 strands with GFP 1-9, thereby forming the fluorescent chromophore, indicating that B and A interact. If B and A do not interact, then GFP S10 and GFP S11 are not tethered, the complementation of the GFP 1-9 assay fragment inefficient, resulting in weak or no fluorescence complementation.

Example 30

Identifying Interacting Binding Ligands Using a Random Genetic Screen

GFP 10 is fused to an genetically encoded antigen A as GFP S10-A or A-GFP S10. A random library BLIB containing potential binding ligands with A is expressed as a fusion with GFP S11 as BLIB-GFP S11 or GFP S11-BLIB. It is obvious that the alternative configuration of GFP S10-BLIB, BLIB-GFP S10 or GFP S11-A, A-GFP S11 could be used. The proteins are expressed within a cellular compartment, cell or cell-free extracts and made to contact one another, such that single member i of BLIB i.e. BLIBi-GFP S11 or GFP S11-BLIBi is made to interact with GFP S10-A or A-GFP S10. If A and BLIBi interact and bind with one another, they cause the tethering of GFP S10 and GFP S11, reducing the configurational entropy of the fused GFP S10 and GFP S11. Contacting these species with the assay strand GFP 1-9 results in the complementation of the GFP S10 and GFP S11 strands with GFP 1-9, thereby forming the fluorescent chromophore, indicating that A and BLIBi interact. If A and BLIBi do not interact, then GFP S10 and GFP S11 are not tethered, making the complementation of the GFP 1-9 assay fragment inefficient, resulting in weak or no fluorescence complementation.

Example 31

Increasing the Stringency of Binding Ligand Selection Using Competitor Binding Ligands This example is an extension of EXAMPLE 29. In this example, a competitive binding ligand Bc is co-expressed within the compartment. Bc competes with BLIB for binding to antigen A. Bc is not fused with a GFP fragment tag, and so binding of A by Bc prevents the binding of A by members of BLIBi-GFP S11 or GFP S11-BLIBi, thus decreasing fluorescence complementation since interaction of A in GFP S10-A or A-GFP S10 with Bc results displacement of BLIBi-GFP S11 or GFP S11-BLIBi, resulting in GFP S10 and GFP S11 not being tethered, making complementation with GFP 1-9 inefficient. Only members of BLIBi-GFP S11 or GFP S11-BLIBi that bind to A more strongly than Bc can displace Bc, resulting in the interaction of A and BLIBi, tethering the fused GFP S10 and GFP S11 domains, resulting in increased fluorescence complementation with GFP 1-9. Bc could be expressed from the same promoter element as GFP S10-A or A-GFP S10 and BLIBi-GFP S11 or GFP S11-BLIBi, for example using the anhydrotetracycline-inducible tet promoter (Clontech) while the assay fragment GFP 1-9 could be expressed from a separately inducible promoter element such as the IPTG-inducible T7 promoter. Sequential expression of the tet promoter constructs, followed by removal of the anhydrotetracycline, then subsequent expression of the GFP 1-9 assay fragment, would detect binding ligand-antigen interactors that were tighter than Bc-antigen interactions, and were also soluble.

Example 33

Engineering Soluble, Non-Perturbing Enzyme Reporter Protein Fragments Requiring Interacting Domains for Reconsistution Previously-described split DHFR fragments were poorly folded, aggregated, and thus form insoluble aggregates (see U.S. Pat. No. 6,428,951). Therein Michnick et al. describe a strategy to select better-folded fragments of DHFR by expressing fragments of DHFR fused to interacting domains, and selecting for increased antibiotic resistance indicating better-folded versions of DHFR. This approach does not guarantee that the fragments will be soluble since the fragments must be co-expressed to confer continued cell survival. To select non-perturbing soluble fragments of DHFR that are also dependent on fused interacting domains, the same approaches used in EXAMPLE 15 and EXAMPLE 16 above are followed, notably using a sequential induction format in which the fragments are separately expressed to select for stable, soluble variants, except an assay specific to DHFR activity is used. Furthermore, small cultures in multiwell culture plates are grown, each containing a variant of the DHFR. Various activity assays are well-known in the art using chromogenic substrates for DHFR activity, and these are used to determine when complementation has occurred. In the first step, self-complementing fragments of DHFR can be selected by screening libraries of DHFR fragment mutants without fused interacting domains for in vivo cell survival. The fragments can be fused to proteins (aggregation bait domains) that exhibit decreased solubility when fused to aggregation prone variants of DHFR, thereby increasing the stringency of selecting soluble variants of DHFR fragments. If desired, one or more of the DHFR fragments, with or without the fused bait domains, can also be fused to GFP microdomains, and the solubility of the DHFR fragment mutants assayed in a high-throughput manner in vivo using the GFP assay fragment using a sequential induction protocol, treating the DHFR fragments as a target protein to be evolved for increased solubility using the GFP split complementation reporter system as in EXAMPLE 9 and EXAMPLE 10. Once soluble candidates are found, they can be screened by co-expression for cell-survival or by mixing the separately expressed candidate soluble evolved DHFR fragments in vitro and using an in vitro DHFR enzymatic activity assay well known in the art, to confirm that the reconstituted, soluble optimized DHFR fragments still provide an enzymaticallly-active DHFR after complementation. These fragments can be expressed simultaneously or separately, and remain soluble, and do not perturb the solubility and folding of fused polypeptides. This is a key requirement for a generally useful protein-protein interaction detection system based on protein fragment reconstitution. However, these fragments self-associate without the need for fused interacting domains. To be useful as protein-protein interaction detectors, the fragments must require fused interacting domains for reconstitution. In one approach, in the absence of fused interacting domains, soluble engineered fragment DHFR F1 is held constant and used as an assay fragment to screen a library of variants of fragment DHFR F2 to identify mutations of F2 which eliminate or abrogate spontaneous complementation and formation of DHFR activity. Similarly, constant non-mutated DHFR F1 can be fused to GFP s-10 and the mutated library DHFR F2 can be fused to GFP s11, and screened using GFP s1-9 to identify mutations in DHFR F2 that abrogate spontaneous association of the DHFR fragments, exemplified by a decrease in the complementation of the assay fragment GFP s1-9. A large library can be screened in *E. coli*, for example, using flow cytometry to find and collect a large number of variants (i.e., >$10^5$) that are non-fluorescent. These non-interacting DHFR variants can include undesirable variants such as those mutants that have folding defects, are incapable of complementation even with fused interacting domains, are insoluble etc. The DHFR F2 GFP s-11 fusions can be screened in vivo using GFP s1-10 assay fragment to confirm they are still soluble, and soluble DHFR F2 mutants that are also not capable of spontaneous assembly with DHFR F1 are thus identified. Then the library of soluble, non-spontaneously associating DHFR F2 variants is then subcloned into vector that causes the mutants to be expressed as fusions with a known interacting protein, such as a coiled-coil (such coiled coils are described in Hu, 2002, supra; Ghosh et al, 2000, supra.). The library is again screened by flow cytometry or on plates to identify those mutants that now complement when fused only to interacting proteins. A secondary DHFR enzyme activity screen can then be applied in vitro to determine that the soluble DHFR fragments also retain enzymatic activity when fused to interacting proteins. If necessary, the final library of optima can now be subcloned into vectors without interacting proteins to verify the dependence on fused interacting domains for complementation. Further rounds of mutation to further improve fragment stability and solubility can be performed if required as in EXAMPLE 3 and EXAMPLE 4, above. Furthermore, bait proteins that have reduced solubility when fused to suboptimal aggregation-prone DHFR fragments can be incorporated into the fusions of this current example (EXAMPLE 33) to maintain stringent selection for solubility during screens for mutations that eliminate spontaneous association. Furthermore, the amino acids specifically involved in the interface between the interacting DHFR fragments can be targeted for increased levels of mutagenesis relative to the scaffolding as a whole using primer-directed mutagenesis (degenerate oligo doping), methods well known in the art (see DEFIINITIONS, methods of mutagenesis, supra), thereby increasing the likelihood that the interaction between the DHFR fragments can be reduced without adversely affecting the folding of the DHFR fragments. The interface amino acids of DHFR can be easily identified by inspection of the three-dimensional structure of DHFR (Filman, 1982, Oefner, 1988, Bystroff, 1991). It is clear to one with average skill in the art that the above approaches can be applied to other enzymatic proteins such as split beta-lactamase or split beta-galactosidase to identify soluble fragment variants that are also dependent on fused interacting domains for complementation.

Example 34

In Vitro Interaction Assay

Expression of Micro GFP Tagged Proteins:

10-FRB and Fkbp12-11 protein fusions were expressed respectively from C-6HIS and N-6his pET 28 vectors (Novagen, Madison, Wis.). 50 ml cultures of BL21 (DE3) expressing each construct were grown to OD600~0.5, and induced with 1 mM IPTG for 5 h at 27° C. The culture pellets were resuspended in 1 ml TNG and sonicated. Inclusion bodies of 10-FRB were denatured in 0.5 ml of 9M Urea and refolded in 5 ml of TNG buffer. The poor solubility of the 10-FRB was expected since FRB-GFP fusions expressed under similar conditions are mostly insoluble, and FRB expressed alone is largely insoluble. Soluble Fkbp12_11 fusion was used without further purification. Bicistronic constructs derived from the pTet vector, were used to coexpress 10-FRB and Fkbp12-11 each from independent ribosome binding sites. The alternative topology 10-Fkbp12+FRB-11 was similarly constructed. Constructs were induced using the same conditions as above, but using 300 ng/ml anhydrotetracycline as the inducer. Soluble fraction was used for complementation assays.

Complementation Assay and Induction of Protein-Protein Interactions with Rapamycin:

The different constructs were tested for complementation in the presence of large fragment 1-9opt and with or without the addition of 100 nM rapamycin. 20 µl of coexpressed 10-FRB and Fkbp12-11 soluble fraction (FIG. 28, row 1), or 20 µl of coexpressed 10-Fkbp12 and FRB-11 (FIG. 28 row 2) were mixed with 80 µl of 1-9opt. For proteins expressed individually (FIG. 28 row 3), 20 µl of refolded 10-FRB and 10 µl of soluble Fkbp12__11 were mixed with 70 µl of 1-9opt. In one example, no rapamycin was added (FIG. 28 first column marked "−"). In another example, 100 nM of rapamycin was added (10 µl of a 1 µM stock solution diluted in DMSO, FIG. 28 second column marked "+"). After overnight incubation, the plate was photographed λexc=488 nm, λem=520 nm (FIG. 28). Final fluorescence values were measured after overnight incubation, using with a FL600 microplate fluorescence reader (Bio-Tek, Winooski, Vt.) using (λexc=488 nm, λem=520 nm) (FIG. 29).

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

LITERATURE CITED

Adams, S. R., R. E. Campbell, et al. (2002). "New biarsenical ligands and tetracysteine motifs for protein labeling in vitro and in vivo: synthesis and biological applications." *J Am Chem Soc* 124(21): 6063-76.

Arai, M., K. Maki, et al. (2003). "Testing the relationship between foldability and the early folding events of dihydrofolate reductase from *Escherichia coli*." *J Mol Biol* 328(1): 273-88.

Armstrong, N., A. de Lencastre, et al. (1999). "A new protein folding screen: application to the ligand binding domains of a glutamate and kainate receptor and to lysozyme and carbonic anhydrase." *Protein Sci* 8(7): 1475-83.

Baird, G. S., D. A. Zacharias, et al. (1999). "Circular permutation and receptor insertion within green fluorescent proteins." *Proc Natl Acad Sci USA* 96(20): 11241-6.

Baneyx, F. (1999). "Recombinant protein expression in *Escherichia coli*." *Curr Opin Biotechnol* 10(5): 411-21.

Bertens, P., W. Heijne, et al. (2003). "Studies on the C-terminus of the Cowpea mosaic virus movement protein." *Arch Virol* 148(2): 265-79.

Bystroff, C. & Kraut, J. (1991) "Crystal structure of unliganded *Escherichia coli* dihydrofolate reductase. Ligand-induced conformational changes and cooperativity in binding" *Biochemistry* 30, 2227-2239.

Crameri, A., E. A. Whitehorn, et al. (1996). "Improved green fluorescent protein by molecular evolution using DNA shuffling." Nat Biotechnol 14(3): 315-9.

Fahnert, B., H. Lilie, et al. (2004). "Inclusion bodies: formation and utilisation." Adv Biochem Eng Biotechnol 89: 93-142.

Filman, D. J., Bolin, J. T., Matthews, D. A. & Kraut, J. (1982) "Crystal structures of Escherichia coli and Lactobacillus casei dihydrofolate reductase refined at 1.7 A resolution. II. Environment of bound NADPH and implications for catalysis." J. Biol. Chem. 257, 13663-13672.

Fitz-Gibbon, S., A. J. Choi, et al. (1997). "A fosmid-based genomic map and identification of 474 genes of the hyperthermophilic archaeon Pyrobaculum aerophilum." Extremophiles 1(1): 36-51.

Fox, J. D., R. B. Kapust, et al. (2001). "Single amino acid substitutions on the surface of Escherichia coli maltose-binding protein can have a profound impact on the solubility of fusion proteins." Protein Sci 10(3): 622-30.

Gegg, C. V., K. E. Bowers, et al. (1997). "Probing minimal independent folding units in dihydrofolate reductase by molecular dissection." Protein Sci 6(9): 1885-92.

Gerstein, M., A. Edwards, et al. (2003). "Structural genomics: current progress." Science 299(5613): 1663.

Goh, C. S., N. Lan, et al. (2004). "Mining the structural genomics pipeline: identification of protein properties that affect high-throughput experimental analysis." J Mol Biol 336(1): 115-30.

Iwakura, M. and T. Nakamura (1998). "Effects of the length of a glycine linker connecting the N- and C-termini of a circularly permuted dihydrofolate reductase." Protein Eng 11(8): 707-13.

Iwakura, M., T. Nakamura, et al. (2000). "Systematic circular permutation of an entire protein reveals essential folding elements." Nat Struct Biol 7(7): 580-5.

Jappelli, R., A. Luzzago, et al. (1992). "Loop mutations can cause a substantial conformational change in the carboxy terminus of the ferritin protein." J Mol Biol 227(2): 532-43.

Kelemen, B. R., T. A. Klink, et al. (1999). "Hypersensitive substrate for ribonucleases." Nucleic Acids Res 27(18): 3696-701.

Kim, J. S. and R. T. Raines (1993). "Ribonuclease S-peptide as a carrier in fusion proteins." Protein Sci 2(3): 348-56.

Knaust, R. K. and P. Nordlund (2001). "Screening for soluble expression of recombinant proteins in a 96-well format." Anal Biochem 297(1): 79-85.

Lopes Ferreira, N. and J. H. Alix (2002). "The DnaK chaperone is necessary for alpha-complementation of beta-galactosidase in Escherichia coli." J Bacteriol 184(24): 7047-54.

Lutz, R. and H. Bujard (1997). "Independent and tight regulation of transcriptional units in Escherichia coli via the LacR/O, the TetR/O and AraC/I1-I2 regulatory elements." Nucleic Acids Res 25(6): 1203-10.

Makrides, S. C. (1996). "Strategies for achieving high-level expression of genes in Escherichia coli." Microbiol Rev 60(3): 512-38.

Nixon, A. E. and S. J. Benkovic (2000). "Improvement in the efficiency of formyl transfer of a GAR transformylase hybrid enzyme." Protein Eng 13(5): 323-7.

Oefner, C., D'Arcy, A. & Winkler, F. K. (1988) "Crystal structure of human dihydrofolate reductase complexed with folate". Eur. J. Biochem. 174: 377-385.

Ormö, M., A. B. Cubitt, et al. (1996). "Crystal structure of the Aequorea victoria green fluorescent protein." Science 273 (5280): 1392-1395.

Patterson, G. H., S. M. Knobel, et al. (1997). "Use of the green fluorescent protein and its mutants in quantitative fluorescence microscopy." Biophys J 73(5): 2782-90.

Pelletier, J. N., K. M. Arndt, et al. (1999). "An in vivo library-versus-library selection of optimized protein-protein interactions." Nat Biotechnol 17(7): 683-90.

Pelletier, J. N., F. X. Campbell-Valois, et al. (1998). "Oligomerization domain-directed reassembly of active dihydrofolate reductase from rationally designed fragments." Proc Natl Acad Sci USA 95(21): 12141-6. Paulmurugan, R. and S. S. Gambhir (2005). "Novel fusion protein approach for efficient high-throughput screening of small molecule-mediating protein-protein interactions in cells and living animals." Cancer Res 65(16): 7413-20.

Pelletier, J. N., K. M. Arndt, et al. (1999). "An in vivo library-versus-library selection of optimized protein-protein interactions." Nat Biotechnol 17(7): 683-90.

Remy, I. and S. W. Michnick (1999). "Clonal selection and in vivo quantitation of protein interactions with protein-fragment complementation assays." Proc Natl Acad Sci USA 96(10): 5394-9.

Richards, F. M. and P. J. Vithayathil (1959). "The preparation of subtilisn-modified ribonuclease and the separation of the peptide and protein components." J Biol Chem 234(6): 1459-65.

Rossi, F. M., B. T. Blakely, et al. (2000). "Monitoring protein-protein interactions in live mammalian cells by beta-galactosidase complementation." Methods Enzymol 328: 231-51.

Smith, V. F. and C. R. Matthews (2001). "Testing the role of chain connectivity on the stability and structure of dihydrofolate reductase from E. coli: fragment complementation and circular permutation reveal stable, alternatively folded forms." Protein Sci 10(1): 116-28.

Stemmer, W. P. (1994). "DNA shuffling by random fragmentation and reassembly: in vitro recombination for molecular evolution." Proc Natl Acad Sci USA 91(22): 10747-51.

Studier, F. W., A. H. Rosenberg, et al. (1990). "Use of T7 RNA polymerase to direct expression of cloned genes." Methods Enzymol 185: 60-89.

Tal, M., A. Silberstein, et al. (1985). "Why does Coomassie Brilliant Blue R interact differently with different proteins? A partial answer." J Biol Chem 260(18): 9976-80.

Terwilliger, T. C. (2004). "Structures and technology for biologists." Nat Struct Mol Biol 11 (4): 296-7.

Tsien, R. Y. (1998). "The green fluorescent protein." Annu Rev Biochem 67: 509-44.

Ullmann, A., F. Jacob, et al. (1967). "Characterization by in vitro complementation of a peptide corresponding to an operator-proximal segment of the beta-galactosidase structural gene of Escherichia coli." J Mol Biol 24(2): 339-43.

Waldo, G. S. (2003). "Genetic screens and directed evolution for protein solubility." Curr Opin Chem Biol 7(1): 33-8.

Waldo, G. S. (2003). "Improving protein folding efficiency by directed evolution using the GFP folding reporter." Methods Mol Biol 230: 343-59.

Waldo, G. S., B. M. Standish, et al. (1999). "Rapid protein-folding assay using green fluorescent protein." Nature Biotechnology 17(#7): 691-695.

Wehrman, T., B. Kleaveland, et al. (2002). "Protein-protein interactions monitored in mammalian cells via complementation of beta-lactamase enzyme fragments." Proc Natl Acad Sci USA 99(6): 3469-74.

Welply, J. K., A. V. Fowler, et al. (1981). "beta-Galactosidase alpha-complementation. Effect of single amino acid substitutions." J Biol Chem 256(13): 6811-6.

Wigley, W. C., R. D. Stidham, et al. (2001). "Protein solubility and folding monitored in vivo by structural complementation of a genetic marker protein." Nat Biotechnol 19(2): 131-6.

Worrall, D. M. and N. H. Goss (1989). "The formation of biologically active beta-galactosidase inclusion bodies in Escherichia coli." Aust J Biotechnol 3(1): 28-32.

Yang, F., L. G. Moss, et al. (1996). "The molecular structure of green fluorescent protein." Nature Biotechnology 14(10): 1246-1251.

Yokoyama, S. (2003). "Protein expression systems for structural genomics and proteomics." Curr Opin Chem Biol 7(1): 3943.

TABLE OF SEQUENCES

SEQ ID NO:1
GFP superfolder 1-10 nucleotide sequence:
ATGAGCAAAGGAGAAGAACTTTTCACTGGAGTTGTCCCAATTCTTGTTGAATTAGATGGTGATGTTAATGGGCACAAA
TTTTCTGTCAGAGGAGAGGGTGAAGGTGATGCTACAAACGGAAAACTCACCCTTAAATTTATTTGCACTACTGGAAAA
CTACCTGTTCCATGGCCAACACTTGTCACTACTCTGACCTATGGTGTTCAATGCTTTTCCCGTTATCCGGATCACATG
AAACGGCATGACTTTTTCAAGAGTGCCATGCCCGAAGGTTATGTACAGGAACGCACTATATCTTTCAAAGATGACGGG
ACCTACAAGACGCGTGCTGAAGTCAAGTTTGAAGGTGATACCCTTGTTAATCGTATCGAGTTAAAAGGTATTGATTTT
AAAGAAGATGGAAACATTCTCGGACACAAACTCGAGTACAACTTTAACTCACACAATGTATACATCACGGCAGACAAA
CAAAAGAATGGAATCAAAGCTAACTTCAAAATTCGCCACAACGTTGAAGATGGTTCCGTTCAACTAGCAGACCATTAT
CAACAAAATACTCCAATTGGCGATGGCCCTGTCCTTTTACCAGACAACCATTACCTGTCGACACAATCTGTCCTTTCG
AAAGATCCCAACGAAAAGCTAA SEQ ID NO:2
GFP super folder 1-10 amino acid sequence:
MSKGEELFTGVVPILVELDGDVNGHKFSVRGEGEGDATNGKLTLKFICTTGKLPVPWPTLVTTLTYGVQCFSRYPDHM
KRHDFFKSAMPEGYVQERTISFKDDGTYKTRAEVKFEGDTLVNRIELKGIDFKEDGNILGHKLEYNFNSHNVYITADK
QKNGIKANFKIRHNVEDGSVQLADHYQQNTPIGDGPVLLPDNHYLSTQSVLSKDPNEK SEQ ID NO:3
GFP 1-10 OPT nucleotide sequence:
ATGAGCAAAGGAGAAGAACTTTTCACTGGAGTTGTCCCAATTCTTGTTGAATTAGATGGTGATGTTAATGGGCACAAA
TTTTCTGTCAGAGGAGAGGGTGAAGGTGATGCTACAATCGGAAAACTCACCCTTAAATTTATTTGCACTACTGGAAAA
CTACCTGTTCCATGGCCAACACTTGTCACTACTCTGACCTATGGTGTTCAATGCTTTTCCCGTTATCCGGATCACATG
AAAAGGCATGACTTTTTCAAGAGTGCCATGCCCGAAGGTTATGTACAGGAACGCACTATATCTTTCAAAGATGACGGG
AAATACAAGACGCGTGCTGTAGTCAAGTTTGAAGGTGATACCCTTGTTAATCGTATCGAGTTAAAGGGTACTGATTTT
AAAGAAGATGGAAACATTCTCGGACACAAACTCGAGTACAACTTTAACTCACACAATGTATACATCACGGCAGACAAA
CAAAAGAATGGAATCAAAGCTAACTTCACAGTTCGCCACAACGTTGAAGATGGTTCCGTTCAACTAGCAGACCATTAT
CAACAAAATACTCCAATTGGCGATGGCCCTGTCCTTTTACCAGACAACCATTACCTGTCGACACAAACTGTCCTTTCG
AAAGATCCCAACGAAAAGGGTACCTAA SEQ ID NO:4
GFP 1-10 OPT amino acid sequence:
(additional mutations vs. superfolder: N39I, T105K, E111V, I128T, K166T,
1167V, S205T)
MSKGEELFTGVVPILVELDGDVNGHKFSVRGEGEGDATIGKLTLKFICTTGKLPVPWPTLVTTLTYGVQCFSRYPDHM
KRHDFFKSAMPEGYVQERTISFKDDGKYKTRAVVKFEGDTLVNRIELKGTDFKEDGNILGHKLEYNFNSHNVYITADK
QKNGIKANFTVRHNVEDGSVQLADHYQQNTPIGDGPVLLPDNHYLSTQTVLSKDPNEKGT SEQ ID NO:5
GFP 1-10 A4 nucleotide sequence:
ATGAGCAAAGGAGAAGAACTTTTCACTGGAGTTGTCCCAATTCTTGTTGAATTAGATGGAGATGTTAATGGGCACAAA
TTTTCTGTCAGAGGAGAGGGTGAAGGTGATGCTACAAACGGAAAACTCACCCTTAAATTCATTTGCACTACTGGAAAA
CTACCTGTTCCATGGCCAACGCTTGTCACTACTCTGACCTATGGTGTTCAATGCTTTTCCCGTTATCCGGATCACATG
AAACAGCATGACTTTTTCAAGAGTGCCATGCCCGAAGGTTATGTACAGGAACGCACTATATATTTCAAAGATGACGGG
AACTACAAGACGCGTGCTGTAGTCAAGTTTGAAGGTGATACCCTTGTTAATCGTATCGAGTTAAAGGGTACTGATTTT
AAAGAAGATGGAAACATTCTCGGACACAAACTCGAGTACAACTTTAACTCACACAATGTATATATCACGGCAGACAAA
CAAAAGAATGGAATCAAAGCTAACTTCACAATTCGCCACAACGTTGTAGATGGTTCCGTTCAACTAGCAGACCATTAT
CAACAAAATACTCCAATTGGCGATGGCCCTGTCCTTTTACCAGACAACCATTACCTGTCGACACAAACTGTCCTTTCG
AAAGATCCCAACGAAAAGGGTACCTAA SEQ ID NO:6
GFP 1-10 A4 amino acid sequence:
(additional mutations versus Superfolder GFP: R80Q, S99Y, T105N, E111V, I128T,
K166T, E172V, S205T)
MSKGEELFTGVVPILVELDGDVNGHKFSVRGEGEGDATNGKLTLKFICTTGKLPVPWPTLVTTLTYGVQCFSRYPDHM
KQHDFFKSAMPEGYVQERTIYFKDDGNYKTRAVVKFEGDTLVNRIELKGTDFKEDGNILGHKLEYNFNSHNVYITADK
QKNGIKANFTIRHNVVDGSVQLADHYQQNTPIGDGPVLLPDNHYLSTQTVLSKDPNEKGT SEQ ID NO:7
GFP S11 214-238 nucleotide sequence:
AAGCGTGACCACATGGTCCTTCTTGAGTTTGTAACTGCTGCTGGGATTACACATGGCATGGATGAGCTCTACAAAGGT
ACCTAA SEQ ID NO:8
GFP S11 214-238 amino acid sequence:
KRDHMVLLEFVTAAGITHGMDELYKGT

TABLE OF SEQUENCES

SEQ ID NO:9
GFP S11 214-230 nucleotide sequence:
AAGCGTGACCACATGGTCCTTCTTGAGTTTGTAACTGCTGCTGGGATTACAGGTACCTAA SEQ ID NO:10
GFP S11 214-230 amino acid sequence:
KRDHMVLLEFVTAAGITGT SEQ ID NO:11
GFP S11 M1 nucleotide sequence:
AAGCGTGACCACATGGTCCTTCATGAGTTTGTAACTGCTGCTGGGATTACAGGTACCTAA SEQ ID NO:12
GFP S11 M1 amino acid sequence:
(Additional mutation versus wt: L221H)
KRDHMVLHEFVTAAGITGT SEQ ID NO:13
GFP S11 M2 nucleotide sequence:
AAGCGTGACCACATGGTCCTTCATGAGTCTGTAAATGCTGCTGGGGGTACCTAA SEQ ID NO:14
GFP S11 M2 amino acid sequence:
(Additional mutations versus GFP 11 wt: L221H, F2235, T225N AA sequence 17
residues
KRDHMVLHESVNAAGGT SEQ ID NO:15
GFP S11 M3 nucleotide sequence:
CGTGACCACATGGTCCTTCATGAGTCTGTAAATGCTGCTGGGATTACATAA SEQ ID NO:16
GFP S11 M3 amino acid sequence:
(Additional mutations versus GFP 11 wt: L221H, F223Y, T225N)
RDHMVLHEYVNAAGIT*

SEQ ID NO:17
GFP S11 H7 nucleotide sequence:
AAGCATGACCACATGCACCTTCATGAGCATGTACATGCTCATGGGGGTACCTAA SEQ ID NO:18
GFP S11 H7 amino acid sequence:
(Additional mutations versus GFP 11 wt: R215H, V219H, L221H, F223H, T225H,
A227H)
KHDHMHLHEHVHAHGGT SEQ ID NO:19
GFP S11 H9 nucleotide sequence:
CATGACCACATGCACCTTCATGAGCATGTACATGCTCATCACCATACCTAA SEQ ID NO:20
GFP S11 H9 amino acid sequence:
(Additional mutations versus GFP 11 wt: R215H, V219H, L221H, F223H, T225H,
A227H, G228H, I229H)
HDHMHLHEHVHAHHHT SEQ ID NO:21
UNIQUE GENETIC ELEMENTS FROM PTET-SPECR VECTOR
(These comprise the elements from T0 to AatlI: tet repressor protein tetR and
the Spectinomycin gene under the control of the kanamycin promoter, and the
RBS that control the expression of the tet repressor)
TTAAGACCCACTTTCACATTTAAGTTGTTTTTCTAATCCGTATATGATCAATTCAAGGCCGAATAAGAAGGCTGGCTC
TGCACCTTGGTGATCAAATAATTCGATAGCTTGTCGTAATAATGGCGGCATACTATCAGTAGTAGGTGTTTCCCTTTC
TTCTTTAGCGACTTGATGCTCTTGATCTTCCAATACGCAACCTAAAGTAAAATGCCCCACAGCGCTGAGTGCATATAA
TGCATTCTCTAGTGAAAAACCTTGTTGGCATAAAAAGGCTAATTGATTTTCGAGAGTTTCATACTGTTTTTCTGTAGG
CCGTGTACCTAAATGTACTTTTGCTCCATCGCGATGACTTAGTAAAGCACATCTAAAACTTTTAGCGTTATTACGTAA
AAAATCTTGCCAGCTTTCCCCTTCTAAAGGGCAAAAGTGAGTATGGTGCCTATCTAACATCTCAATGGCTAAGGCGTC
GAGCAAAGCCCGCTTATTTTTTACATGCCAATACAATGTAGGCTGCTCTACACCTAGCTTCTGGGCGAGTTTACGGGT
TGTTAAACCTTCGATTCCGACCTCATTAAGCAGCTCTAATGCGCTGTTAATCACTTTACTTTTATCTAATCTGGACAT
CATTAATGTTTATTGAGCTCTCGAACCCCAGAGTCCCGCATTATTTGCCGACTACCTTGGTGATCTCGCCTTTCACGT
AGTGGACAAATTCTTCCAACTGATCTGCGCGCGAGGCCAAGCGATCTTCTTCTTGTCCAAGATAAGCCTGTCTAGCTT
CAAGTATGACGGGCTGATACTGGGCCGGCAGGCGCTCCATTGCCCAGTCGGCAGCGACATCCTTCGGCGCGATTTTGC
CGGTTACTGCGCTGTACCAAATGCGGGACAACGTAAGCACTACATTTCGCTCATCGCCAGCCCAGTCGGGCGGCGAGT
TCCATAGCGTTAAGGTTTCATTTAGCGCCTCAAATAGATCCTGTTCAGGAACCGGATCAAAGAGTTCCTCCGCCGCTG
GACCTACCAAGGCAACGCTATGTTCTCTTGCTTTTGTCAGCAAGATAGCCAGATCAATGTCGATCGTGGCTGGCTCGA
AGATACCTGCAAGAATGTCATTGCGCTGCCATTCTCCAAATTGCAGTTCGCGCTTAGCTGGATAACGCCACGGAATGA
TGTCGTCGTGCACAACAATGGTGACTTCTACAGCGCGGAGAATCTCGCTCTCTCCAGGGGAAGCCGAAGTTTCCAAAA

TABLE OF SEQUENCES

```
GGTCGTTGATCAAAGCTCGCCGCGTTGTTTCATCAAGCCTTACGGTCACCGTAACCAGCAAATCAATATCACTGTGTG
GCTTCAGGCCGCCATCCACTGCGGAGCCGTACAAATGTACGGCCAGCAACGTCGGTTCGAGATGGCGCTCGATGACGC
CAACTACCTCTGATAGTTGAGTCGATACTTCGGCGATCACCGCTTCCCTCATGATGTTTAACTTTGTTTTAGGGCGAC
TGCCCTGCTGCGTAACATCGTTGCTGCTCCATAACATCAAACATCGACCCACGGCGTAACGCGCTTGCTGCTTGGATG
CCCGAGGCATAGACTGTACCCCAAAAAAACATGTCATAACAAGCCATGAAAACCGCCACTGCGCCGTTACCATGCGAA
ACGATCCTCATCCTGTCTCTTGATCAGATCTTGATCCCCTGCGCCATCAGATCCTTGGCGGCAAGAAAGCCATCCAGT
TTACTTTGCAGGGCTTCCCAACCTTACCAGAGGGCGCCCCAGCTGGCAATTCCGACGTC
```

SEQ ID NO:22
COMPLETE PTET-SPECR VECTOR SEQUENCE
```
TCGAGTCCCTATCAGTGATAGAGATTGACATCCCTATCAGTGATAGAGATACTGAGCACATCAGCAGGACGCACTGAC
CGAGTTCATTAAAGAGGAGAAAGATACCCATGGGCAGCAGCCATCATCATCATCATCACAGCAGCGGCCTGGTGCCGC
GCGGCAGCCATATGGGTGGCGGTTCTGGATCCGGAGGCACTAGTGGTGGCGGCTCAGGTACCTAACTCGAGCACCACC
ACCACCACCACTGAGATCCGGCTGCTAACAAAGCCCGAAAGGAAGCTGAGTTGGCGTCTGCCACCGCTGAGCAATAAC
TAGCATAACCTCTAGAGGCATCAAATAAAACGAAAGGCTCAGTCGAAAGACTGGGCCTTTCGTTTTATCTGTTGTTTG
TCGGTGAACGCTCTCCTGAGTAGGACAAATCCGCCGCCCTAGACCTAGGCGTTCGGCTGCGGCGAGCGGTATCAGCTC
ACTCAAAGGCGGTAATACGGTTATCCACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCCCTGACGAGCATCACAAAAATC
GACGCTCAAGTCAGAGGTGGCGAAACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCGGGAAGCGTGGCGCTTTCTCAAT
GCTCACGCTGTAGGTATCTCAGTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACAGACTTATCGCCACTGGCAGCAG
CCACTGGTAACAGGATTAGCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAAGAGTTGGTAGCTCTTGAT
CCGGCAAACAAACCACCGCTGGTAGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCACGTTAAGGGATTTTGGTCATGA
CTAGCGCTTGGATTCTCACCAATAAAAAACGCCCGGCGGCAACCGAGCGTTCTGAACAAATCCAGATGGAGTTCTGAG
GTCATTACTGGATCTATCAACAGGAGTCCAAGCTTAAGACCCACTTTCACATTTAAGTTGTTTTTCTAATCCGTATAT
GATCAATTCAAGGCCGAATAAGAAGGCTGGCTCTGCACCTTGGTGATCAAATAATTCGATAGCTTGTCGTAATAATGG
CGGCATACTATCAGTAGTAGGTGTTTCCCTTTCTTCTTTAGCGACTTGATGCTCTTGATCTTCCAATACGCAACCTAA
AGTAAAATGCCCCACAGCGCTGAGTGCATATAATGCATTCTCTAGTGAAAAACCTTGTTGGCATAAAAAGGCTAATTG
ATTTTCGAGAGTTTCATACTGTTTTTCTGTAGGCCGTGTACCTAAATGTACTTTTGCTCCATCGCGATGACTTAGTAA
AGCACATCTAAAACTTTTAGCGTTATTACGTAAAAAATCTTGCCAGCTTTCCCCTTCTAAAGGGCAAAAGTGAGTATG
GTGCCTATCTAACATCTCAATGGCTAAGGCGTCGAGCAAAGCCCGCTTATTTTTTACATGCCAATACAATGTAGGCTG
CTCTACACCTAGCTTCTGGGCGAGTTTACGGGTTGTTAAACCTTCGATTCCGACCTCATTAAGCAGCTCTAATGCGCT
GTTAATCACTTTACTTTTATCTAATCTGGACATCATTAATGTTTATTGAGCTCTCGAACCCCAGAGTCCCGCATTATT
TGCCGACTACCTTGGTGATCTCGCCTTTCACGTAGTGGACAAATTCTTCCAACTGATCTGCGCGCGAGGCCAAGCGAT
CTTCTTCTTGTCCAAGATAAGCCTGTCTAGCTTCAAGTATGACGGGCTGATACTGGGCCGGCAGGCGCTCCATTGCCC
AGTCGGCAGCGACATCCTTCGGCGCGATTTTGCCGGTTACTGCGCTGTACCAAATGCGGGACAACGTAAGCACTACAT
TTCGCTCATCGCCAGCCCAGTCGGGCGGCGAGTTCCATAGCGTTAAGGTTTCATTTAGCGCCTCAAATAGATCCTGTT
CAGGAACCGGATCAAAGAGTTCCTCCGCCGCTGGACCTACCAAGGCAACGCTATGTTCTCTTGCTTTTGTCAGCAAGA
TAGCCAGATCAATGTCGATCGTGGCTGGCTCGAAGATACCTGCAAGAATGTCATTGCGCTGCCATTCTCCAAATTGCA
GTTCGCGCTTAGCTGGATAACGCCACGGAATGATGTCGTCGTGCACAACAATGGTGACTTCTACAGCGCGGAGAATCT
CGCTCTCTCCAGGGGAAGCCGAAGTTTCCAAAAGGTCGTTGATCAAAGCTCGCCGCGTTGTTTCATCAAGCCTTACGG
TCACCGTAACCAGCAAATCAATATCACTGTGTGGCTTCAGGCCGCCATCCACTGCGGAGCCGTACAAATGTACGGCCA
GCAACGTCGGTTCGAGATGGCGCTCGATGACGCCAACTACCTCTGATAGTTGAGTCGATACTTCGGCGATCACCGCTT
CCCTCATGATGTTTAACTTTGTTTTAGGGCGACTGCCCTGCTGCGTAACATCGTTGCTGCTCCATAACATCAAACATC
GACCCACGGCGTAACGCGCTTGCTGCTTGGATGCCCGAGGCATAGACTGTACCCCAAAAAAACATGTCATAACAAGCC
ATGAAAACCGCCACTGCGCCGTTACCATGCGAAACGATCCTCATCCTGTCTCTTGATCAGATCTTGATCCCCTGCGCC
ATCAGATCCTTGGCGGCAAGAAAGCCATCCAGTTTACTTTGCAGGGCTTCCCAACCTTACCAGAGGGCGCCCCAGCTG
GCAATTCCGACGTCTAAGAAACCATTATTATCATGACATTAACCTATAAAAATAGGCGTATCACGAGGCCCTTTCGTC
TTCACC
```

SEQ ID NO:33
Nucleotide sequence of GFP 1-9 OPT
```
ATGCGAAAGGAGAAGAACTTTTCACTGGAGTTGTCCCAATTCTTGTTGAATTAGATGGTGATGTTAATGGGCACAAA
TTTTCTGTCCGTGGAGAGGGTGAAGGTGATGCTACAAACGGAAAACTCAGCCTTAAATTTATTTGCACTACTGGAAAA
CTACCTGTTCCATGGCCAACACTTGTCACTACTCTGACCTATGGTGTTCAATGCTTTTCCCGTTATCCGGATCACATG
AAACGGCATGACTTTTTCAAGAGTGTCATGCCCGAAGGTTATGTACAGGAACGCACTATATCTTTCAAAGATGACGGG
ACCTACAAGACGCGTGCTGAAGTCAAGTCTGAAGGTGATACCCTTGTTAATCGTATCGAGTTAAAAGGTATTGATTTT
AAAGAAGATGGAAACATTCTCGGACACAAACTCGAGTACAACTTTAACTCACACAATGTATACATCACGGCAGACAAA
CAAAAGAATGGAATCAAAGCTAACTTCACAATTCGCCACAACGTTGAAGATGGTTCCGTTCAACTAGCAGACCATTAT
CAACAAAATACTCCAATTGGCGATGGCCCTGTCCTTTTACCAGACAATAA
```

SEQ ID NO:34
Amino sequence of GFP 1-9 OPT
MRKGEELFTGVVPILVELDGDVNGHKFSVRGEGEGDATNGKLSLKFICTTGKLPVPWPTLVTTLTYGVQCFSRYPDHMK
RHDFFKSVMPEGYVQERTISFKDDGTYKTRAEVKSEGDTLVNRIELKGIDFKEDGNILGHKLEYNFNSHNVYITADKQ
KNGIKANFTIRHNVEDGSVQLADHYQQNTPIGDGPVLLPD SEQ ID NO:36
Amino acid sequence of GFP 10-11 OPT
DHYLSTQTILSKDPNEERDHMVLLESVTAAGITHGMDELYK SEQ ID NO:39
Amino acid sequence of NcoI (GFP S10 A4)-KpnI-linker-NdeI-BamHI-linker-SpeI-
(GFP S11 SM5)-NheI-XhoI "10-x-11 sandwich optimum".

TABLE OF SEQUENCES

YTMDLPDDHYLSTQTILSKDLNGTDVGSGGGSHMGGGSGSGGGSGGGSTSEKRDHMVLLEYVTAAGITDAS

SEQ ID NO:43
Nucleotide sequence of GFP 1-10 OPT + GFP S11 M2 "GFP 1-10 OPT M2".
ATGAGCAAAGGAGAAGAACTTTTCACTGGAGTTGTCCCAATTCTTGTTGAATTAGATGGTGATGTTAATGGGCACAAA
TTTTCTGTCAGAGGAGAGGGTGAAGGTGATGCTACAATCGGAAAACTCACCCTTAAATTTATTTGCACTACTGGAAAA
CTACCTGTTCCATGGCCAACACTTGTCACTACTCTGACCTATGGTGTTCAATGCTTTTCCCGTTATCCGGATCACATG
AAAAGGCATGACTTTTTCAAGAGTGCCATGCCCGAAGGTTATGTACAGGAACGCACTATATCTTTCAAAGATGACGGG
AAATACAAGACGCGTGCTGTAGTCAAGTTTGAAGGTGATACCCTTGTTAATCGTATCGAGTTAAAGGGTACTGATTTT
AAGAAGATGGAAACATTCTCGGACACAAACTCGAGTACAACTTTAACTCACACAATGTATACATCACGGCAGACAAA
CAAAAGAATGGAATCAAAGCTAACTTCACAGTTCGCCACAACGTTGAAGATGGTTCCGTTCAACTAGCAGACCATTAT
CAACAAAATACTCCAATTGGCGATGGCCCTGTCCTTTTACCAGACAACCATTACCTGTCGACACAAACTGTCCTTTCG
AAAGATCCCAACGAAAAGCGTGACCACATGGTCCTTCATGAGTCTGTAAATGCTGCTGGGATTACATAA SEQ ID NO:44
Amino acid sequence of GFP 1-10 OPT + GFP S11 M2 "GFP 1-10 OPT M2".
MSKGEELFTGVVPILVELDGDVNGHKFSVRGEGEGDATIGKLTLKFICTTGKLPVPWPTLVTTLTYGVQCFSRYPDHM
KRHDFFKSAMPEGYVQERTISFKDDGKYKTRAVVKFEGDTLVNRIELKGTDFKEDGNILGHKLEYNFNSHNVYITADK
QKNGIKANFTVRHNVEDGSVQLADHYQQNTPIGDGPVLLPDNHYLSTQTVLSKDPNEKRDHMVLHESVNAAGIT*

SEQ ID NO:45
Nucleotide acid sequence of GFP 1-10 OPT + GFP S11 M2 + tail of GFP "GFP 1-10
OPT M2 tailed".
ATGAGCAAAGGAGAAGAACTTTTCACTGGAGTTGTCCCAATTCTTGTTGAATTAGATGGTGATGTTAATGGGCACAAA
TTTTCTGTCAGAGGAGAGGGTGAAGGTGATGCTACAATCGGAAAACTCACCCTTAAATTTATTTGCACTACTGGAAAA
CTACCTGTTCCATGGCCAACACTTGTCACTACTCTGACCTATGGTGTTCAATGCTTTTCCCGTTATCCGGATCACATG
AAAAGGCATGACTTTTTCAAGAGTGCCATGCCCGAAGGTTATGTACAGGAACGCACTATATCTTTCAAAGATGACGGG
AAATACAAGACGCGTGCTGTAGTCAAGTTTGAAGGTGATACCCTTGTTAATCGTATCGAGTTAAAGGGTACTGATTTT
AAGAAGATGGAAACATTCTCGGACACAAACTCGAGTACAACTTTAACTCACACAATGTATACATCACGGCAGACAAA
CAAAAGAATGGAATCAAAGCTAACTTCACAGTTCGCCACAACGTTGAAGATGGTTCCGTTCAACTAGCAGACCATTAT
CAACAAAATACTCCAATTGGCGATGGCCCTGTCCTTTTACCAGACAACCATTACCTGTCGACACAAACTGTCCTTTCG
AAAGATCCCAACGAAAAGCGTGACCACATGGTCCTTCATGAGTCTGTAAATGCTGCTGGGATTACACATGGCATGGAT
GAGCTCTACAAATAA SEQ ID NO:46
Amino acid sequence of GFP 1-10 OPT + GFP S11 M2 + tail of GFP "GFP 1-10 OPT
M2 tailed".
MSKGEELFTGVVPILVELDGDVNGHKFSVRGEGEGDATIGKLTLKFICTTGKLPVPWPTLVTTLTYGVQCFSRYPDHM
KRHDFFKSAMPEGYVQERTISFKDDGKYKTRAVVKFEGDTLVNRIELKGTDFKEDGNILGHKLEYNFNSHNVYITADK
QKNGIKANFTVRHNVEDGSVQLADHYQQNTPIGDGPVLLPDNHYLSTQTVLSKDPNEKRDHMVLHESVNAAGITHGMD
ELYK*

SEQ ID NO:47
Nucleotide a sequence of GFP 10-11 OPT.
GACCATTACCTGTCGACACAAACTATCCTTTCGAAAGATCCCAACGAAGAGCGTGACCACATGGTCCTTCTTGAGTCT
GTAACTGCTGCTGGGATTACACATGGCATGGATGAGCTCTACAAAT SEQ ID NO:48
Nucleotide sequence of NcoI (GFP S10 A4)-KpnI-linker-NdeI-BamHI-linker-SpeI-
(GFP S11 SM5)-NheI-XhoI "10-x-11 sandwich optimum".
GATATACCATGGATTTACCAGACGACCATTACCTGTCGACACAAACTATCCTTTCGAAAGATCTCAACGGTACCGACG
TTGGGTCTGGCGGTGCCTCCCATATGGGTGGCGGTTCTGGATCCGGTGGAGGGTCTGGTGGCGGATCAACTAGTGAAA
AGCGTGACCACATGGTCCTTCTTGAGTATGTAACTGCTGCTGGGATTACAGATGCTAGCTAACTCGAGAATAGC SEQ ID NO:49
Nucleotide sequence of GFP 1-10 OPT + GFP S11 M3 "GFP 1-10 OPT M3".
ATGAGCAAAGGAGAAGAACTTTTCACTGGAGTTGTCCCAATTCTTGTTGAATTAGATGGTGATGTTAATGGGCACAAA
TTTTCTGTCAGAGGAGAGGGTGAAGGTGATGCTACAATCGGAAAACTCACCCTTAAATTTATTTGCACTACTGGAAAA
CTACCTGTTCCATGGCCAACACTTGTCACTACTCTGACCTATGGTGTTCAATGCTTTTCCCGTTATCCGGATCACATG
AAAAGGCATGACTTTTTCAAGAGTGCCATGCCCGAAGGTTATGTACAGGAACGCACTATATCTTTCAAAGATGACGGG
AAATACAAGACGCGTGCTGTAGTCAAGTTTGAAGGTGATACCCTTGTTAATCGTATCGAGTTAAAGGGTACTGATTTT
AAGAAGATGGAAACATTCTCGGACACAAACTCGAGTACAACTTTAACTCACACAATGTATACATCACGGCAGACAAA
CAAAAGAATGGAATCAAAGCTAACTTCACAGTTCGCCACAACGTTGAAGATGGTTCCGTTCAACTAGCAGACCATTAT
CAACAAAATACTCCAATTGGCGATGGCCCTGTCCTTTTACCAGACAACCATTACCTGTCGACACAAACTGTCCTTTCG
AAAGATCCCAACGAAAAGCGTGACCACATGGTCCTTCATGAGTACGTAAATGCTGCTGGGATTACATAA SEQ ID NO:50
Amino acid sequence of GFP 1-10 OPT + GFP S11 M3 "GFP 1-10 OPT M3".
MSKGEELFTGVVPILVELDGDVNGHKFSVRGEGEGDATIGKLTLKFICTTGKLPVPWPTLVTTLTYGVQCFSRYPDHM
KRHDFFKSAMPEGYVQERTISFKDDGKYKTRAVVKFEGDTLVNRIELKGTDFKEDGNILGHKLEYNFNSHNVYITADK
QKNGIKANFTVRHNVEDGSVQLADHYQQNTPIGDGPVLLPDNHYLSTQTVLSKDPNEKRDHMVLHEYVNAAGIT*

SEQ ID NO:51
Nucleotide acid sequence of GFP 1-10 OPT + GFP S11 M3 + tail of GFP "GFP 1-10
OPT M3 tailed".
ATGAGCAAAGGAGAAGAACTTTTCACTGGAGTTGTCCCAATTCTTGTTGAATTAGATGGTGATGTTAATGGGCACAAA
TTTTCTGTCAGAGGAGAGGGTGAAGGTGATGCTACAATCGGAAAACTCACCCTTAAATTTATTTGCACTACTGGAAAA

TABLE OF SEQUENCES

```
CTACCTGTTCCATGGCCAACACTTGTCACTACTCTGACCTATGGTGTTCAATGCTTTTCCCGTTATCCGGATCACATG
AAAAGGCATGACTTTTTCAAGAGTGCCATGCCCGAAGGTTATGTACAGGAACGCACTATATCTTTCAAAGATGACGGG
AAATACAAGACGCGTGCTGTAGTCAAGTTTGAAGGTGATACCCTTGTTAATCGTATCGAGTTAAAGGGTACTGATTTT
AAAGAAGATGGAAACATTCTCGGACACAAACTCGAGTACAACTTTAACTCACACAATGTATACATCACGGCAGACAAA
CAAAAGAATGGAATCAAAGCTAACTTCACAGTTCGCCACAACGTTGAAGATGGTTCCGTTCAACTAGCAGACCATTAT
CAACAAAATACTCCAATTGGCGATGGCCCTGTCCTTTTACCAGACAACCATTACCTGTCGACACAAACTGTCCTTTCG
AAAGATCCCAACGAAAAGCGTGACCACATGGTCCTTCATGAGTACGTAAATGCTGCTGGGATTACACATGGCATGGAT
GAGCTCTACAAATAA

SEQ ID NO:52
Amino acid sequence of GFP 1-10 OPT + GFP S11 M3 + tail of GFP "GFP 1-10 OPT
M3 tailed".
MSKGEELFTGVVPILVELDGDVNGHKFSVRGEGEGDATIGKLTLKFICTTGKLPVPWPTLVTTLTYGVQCFSRYPDHM
KRHDFFKSAMPEGYVQERTISFKDDGKYKTRAVVKFEGDTLVNRIELKGTDPKEDGNILGHKLEYNFNSHNVYITADK
QKNGIKANFTVRHNVEDGSVQLADHYQQNTPIGDGPVLLPDNHYLSTQTVLSKDPNEKRDHMVLHEYVNAAGITHGMD
ELYK*

SEQ ID NOS:53-54
Amino acid and nucleotide equences of clone 10-FRB-C6HIS.

M   D   L   P   D   D   H   Y   L   S   T   Q   T   I   L   S   K   D   L   N   G   T   D   V
CCATGGATTTACCAGACGACCATTACCTGTCGACACAAACTATCCTTTCGAAAGATCTCAACGGAACTGACGTT
GGTACCTAAATGGTCTGCTGGTAATGGACAGCTGTGTTTGATAGGAAAGCTTTCTAGAGTTGCCTTGACTGCAA

G   S   G   G   G   S   H   M   E   L   I   R   V   A   I   L   W   H   E   M   W   H   E   G   L   E
GGGTCTGGCGGTGGTTCCCATATGGAGCTGATCCGAGTGGCCATCCTCTGGCATGAGATGTGGCATGAAGGCCTGGAA
CCCAGACCGCCACCAAGGGTATACCTCGACTAGGCTCACCGGTAGGAGACCGTACTCTACACCGTACTTCCGGACCTT

E   A   S   R   L   Y   F   G   E   R   N   V   K   G   M   F   E   V   L   E   P   L   H   A   M   M
GAGGCATCTCGTTTGTACTTTGGGGAAAGGAACGTGAAAGGCATGTTTGAGGTGCTGGAGCCCTTGCATGCTATGATG
CTCCGTAGAGCAAACATGAAACCCCTTCCTTGCACTTTCCGTACAAACTCCACGACCTCGGGAACGTACGATACTAC

E   R   G   P   Q   T   L   K   E   T   S   F   N   Q   A   Y   G   R   D   L   M   E   A   Q   E   W
GAACGGGGCCCCCAGACTCTGAAGGAAACATCCTTTAATCAGGCCTATGGTCGAGATTTAATGGAGGCCCAAGAGTGG
CTTGCCCCGGGGGTCTGAGACTTCCTTTGTAGGAAATTAGTCCGGATACCAGCTCTAAATTACCTCCGGGTTCTCACC

C   R   K   Y   M   K   S   G   N   V   K   D   L   T   Q   A   W   D   L   Y   Y   H   V   F   R   R
TGCAGGAAGTACATGAAATCAGGGAATGTCAAGGACCTCACCCAAGCCTGGGACCTCTATTATCATGTGTTCCGACGA
ACGTCCTTCATGTACTTTAGTCCCTTACAGTTCCTGGAGTGGGTTCGGACCCTGGAGATAATAGTACACAAGGCTGCT

I   S   K   Q   G   T   L   E   H   H   H   H   H   H   *
ATCTCAAAGCAGGGTACCCTCGAGCACCACCACCACCACCACTGA
TAGAGTTTCGTCCCATGGGAGCTCGTGGTGGTGGTGGTGGTGACT

SEQ ID NOS:55-56
Amino acid and nucleotide sequences of clone N6HIS-Fkbp12-11.

M   G   S   S   H   H   H   H   H   H   S   S   G   L   V   P   R   G   S   H   M   G
CCATGGGCAGCAGCCATCATCATCATCATCACAGCAGCGGCCTGGTGCCGCGCGGCAGCCATATGGGT
GGTACCCGTCGTCGGTAGTAGTAGTAGTAGTGTCGTCGCCGGACCACGGCGCGCCGTCGGTATACCCA

G   T   S   G   V   Q   V   E   T   I   S   P   G   N   G   R   T   F   P   K   R   G   Q   T   C   V
GGCACTAGTGGAGTGCAGGTGGAAACCATCTCCCCAGGAAACGGGCGCACCTTCCCCAAGCGCGGCCAGACCTGCGTG
CCGTGATCACCTCACGTCCACCTTTGGTAGAGGGGTCCTTTGCCCGCGTGGAAGGGGTTCGCGCCGGTCTGGACGCAC

V   H   Y   T   G   M   L   E   D   G   K   K   F   D   S   S   R   D   R   N   K   P   F   K   F   M
GTGCACTACACCGGGATGCTTGAAGATGGAAAGAAATTTGATTCCTCCCGGGACAGAAACAAGCCCTTTAAGTTTATG
CACGTGATGTGGCCCTACGAACTTCTACCTTTCTTTAAACTAAGGAGGGCCCTGTCTTTGTTCGGGAPATTCAAATAC

L   G   K   Q   E   V   I   R   G   W   E   E   G   V   A   Q   M   S   V   G   Q   R   A   K   L   T
CTAGGCAAGCAGGAGGTGATCCGAGGCTGGGAAGAAGGGGTTGCCCAGATGAGTGTGGGTCAGAGAGCCAAACTGACT
GATCCGTTCGTCCTCCACTAGGCTCCGACCCTTCTTCCCCAACGGGTCTACTCACACCCAGTCTCTCGGTTTGACTGA

I   S   P   D   Y   A   Y   G   A   T   G   H   P   G   I   I   P   P   H   A   T   L   V   F   D   V
ATATCACCTGACTATGCATACGGAGCTACAGGTCATCCTGGAATTATTCCACCTCACGCTACTCTCGTCTTCGATGTG
TATAGTGGACTGATACGTATGCCTCGATGTCCAGTAGGACCTTAATAAGGTGGAGTGCGATGAGACAGAAGCTACAC

E   L   L   K   L   E   G   S   G   G   G   S   G   G   G   S   T   S   E   K   R   D   H   M   V   L
GAGCTTCTAAAACTGGAAGGATCCGGTGGAGGGTCTGGTGGCGGATCAACATCTGAAAAGCGTGACCACATGGTCCTT
CTCGAAGATTTTGACCTTCCTAGGCCACCTCCCAGACCACCGCCTAGTTGTAGACTTTTCGCACTGGTGTACCAGGAA

E   Y   V   T   A   A   G   I   T   D   A   S   *
GAGTATGTAACTGCTGCTGGGATTACAGATGCATCTTAA
CTCATACATTGACGACGACCCTAATGTCTACGTAGAATT
```

What is claimed is:

1. An assay for detecting the interaction of two proteins, X and Y, comprising:
   (a) expressing in a cell a first polynucleotide construct comprising the coding sequence of a soluble first microdomain tag fragment of a fluorescent protein, wherein the microdomain tag fragment corresponds to one or more beta-strands of the fluorescent protein, fused to the coding sequence of protein X;
   (b) expressing in the cell a second polynucleotide construct comprising the coding sequence of a soluble second microdomain tag fragment of the fluorescent protein, wherein the microdomain tag fragment corresponds to one or more other beta-strands of the fluorescent protein, fused to the coding sequence of protein Y, or introducing the fusion protein, Y-microdomain tag, encoded thereby into the cell;
   (c) expressing in the cell a third polynucleotide construct comprising the coding sequence of a soluble assay fragment complementary to the microdomain tag fragments of (a) and (b), wherein the assay fragment corresponds to the remaining beta-strands of the fluorescent protein, or introducing the assay fragment into the cell;
   (d) detecting fluorescence in the cell and thereby detecting the interaction of proteins X and Y,
   wherein the two microdomain tag fragments selected do not self-complement with the assay fragment in the absence of interacting proteins fused thereto.

2. The assay according to claim 1, wherein the first soluble microdomain tag fragment corresponds to a single beta-strand of a GFP fluorescent protein or a GFP-like fluorescent protein or a circular permutant fluorescent protein thereof, the second soluble microdomain tag corresponds to an adjacent beta-strand of the same fluorescent protein, and the assay fragment corresponds to the remaining 9 beta-strands the same fluorescent protein.

3. The assay according to claim 1, wherein the first soluble microdomain tag fragment corresponds to beta-strand s10 of GFP or a GFP-like fluorescent protein or a circular permutant thereof, the second soluble microdomain tag corresponds to beta-strand s11 of the same fluorescent protein, and the assay fragment corresponds to beta-strands s1-9 of the same fluorescent protein.

4. The assay according to claim 1 or 2, wherein proteins X and Y are fused to the N-terminus of the microdomain tag fragments.

5. The assay according to claim 4, wherein the proteins X and Y are fused to the N-terminus of the microdomain tag fragments via a linker polypeptide.

6. The assay according to any one of claims 1-3 wherein proteins X and Y interact in only in the presence of an effector molecule.

7. The assay according to any one of claims 1-3 wherein the assay fragment is introduced into the ceil by chemical transfection.

8. The assay according to any one of claims 1-3 wherein the fusion protein, Y-microdomain tag, is introduced into the cell by chemical transfection.

* * * * *

SEQUENCE LISTING

<160> NUMBER OF SEQ ID NOS: 56

<210> SEQ ID NO 1
<211> LENGTH: 646
<212> TYPE: DNA
<213> ORGANISM: Artificial
<220> FEATURE:
<223> OTHER INFORMATION: GFP variant fragment; sequence encoding
      fragment corresponding to beta-strands 1-10; synthesized DNA
      sequence.

<400> SEQUENCE: 1
atgagcaaag gagaagaact tttcactgga gttgtcccaa ttcttgttga attagatggt      60
gatgttaatg ggcacaaatt ttctgtcaga ggagagggtg aaggtgatgc tacaaacgga     120
aaactcaccc ttaaatttat ttgcactact ggaaaactac ctgttccatg gccaacactt     180
gtcactactc tgacctatgg tgttcaatgc ttttcccgtt atccggatca catgaaacgg     240
catgactttt tcaagagtgc catgcccgaa ggttatgtac aggaacgcac tatatctttc     300
aaagatgacg ggacctacaa gacgcgtgct gaagtcaagt tgaaggtga tacccttgtt     360 aatcgtatcg agttaaaagg tattgatttt aaagaagatg aaacattct cggacacaaa     420 ctcgagtaca actttaactc acacaatgta tacatcacgg cagacaaaca aaagaatgga     480
atcaaagcta acttcaaaat tcgccacaac gttgaagatg gttccgttca actagcagac     540
cattatcaac aaaatactcc aattggcgat ggccctgtcc ttttaccaga caaccattac     600
ctgtcgacac aatctgtcct ttcgaaagat cccaacgaaa agctaa                    646

<210> SEQ ID NO 2
<211> LENGTH: 214
<212> TYPE: PRT
<213> ORGANISM: Artificial
<220> FEATURE:
<223> OTHER INFORMATION: GFP variant fragment; fragment corresponding to
      beta-strands 1-10; expressed from synthesized DNA sequence.

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

```
Ile Lys Ala Asn Phe Lys Ile Arg His Asn Val Glu Asp Gly Ser Val
            165                 170                 175
Gln Leu Ala Asp His Tyr Gln Gln Asn Thr Pro Ile Gly Asp Gly Pro
        180                 185                 190
Val Leu Leu Pro Asp Asn His Tyr Leu Ser Thr Gln Ser Val Leu Ser
        195                 200                 205
Lys Asp Pro Asn Glu Lys
        210
```

<210> SEQ ID NO 3
<211> LENGTH: 651
<212> TYPE: DNA
<213> ORGANISM: Artificial
<220> FEATURE:
<223> OTHER INFORMATION: GFP variant fragment; sequence encoding
      fragment corresponding to beta-strands 1-10 OPT; synthesized DNA
      sequence.

<400> SEQUENCE: 3

```
atgagcaaag gagaagaact tttcactgga gttgtcccaa ttcttgttga attagatggt      60
gatgttaatg gcacaaaatt ttctgtcaga ggagagggtg aaggtgatgc tacaatcgga     120
aaactcaccc ttaaatttat ttgcactact ggaaaactac ctgttccatg gccaacactt     180
gtcactactc tgacctatgg tgttcaatgc ttttcccgtt atccggatca catgaaaagg     240
catgactttt tcaagagtgc catgcccgaa ggttatgtac aggaacgcac tatatctttc     300
aaagatgacg ggaaatacaa gacgcgtgct gtagtcaagt tgaaggtga tacccttgtt     360
aatcgtatcg agttaaaggg tactgatttt aaagaagatg aaacattct cggacacaaa     420
ctcgagtaca actttaactc acacaatgta tacatcacgg cagacaaaca aaagaatgga     480
atcaaagcta acttcacagt tcgccacaac gttgaagatg gttccgttca actagcagac     540
cattatcaac aaaatactcc aattggcgat ggccctgtcc ttttaccaga caaccattac     600
ctgtcgacac aaactgtcct ttcgaaagat cccaacgaaa agggtaccta a              651
```

<210> SEQ ID NO 4
<211> LENGTH: 216
<212> TYPE: PRT
<213> ORGANISM: Artificial
<220> FEATURE:
<223> OTHER INFORMATION: GFP variant fragment; fragment corresponding to
      beta-strands 1-10 OPT; expressed from synthesized DNA sequence.

<400> SEQUENCE: 4

```
Met Ser Lys Gly Glu Glu Leu Phe Thr Gly Val Val Pro Ile Leu Val
1               5                  10                  15
Glu Leu Asp Gly Asp Val Asn Gly His Lys Phe Ser Val Arg Gly Glu
            20                  25                  30
Gly Glu Gly Asp Ala Thr Ile Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Thr Tyr Gly Val Gln Cys Phe Ser Arg Tyr Pro Asp His Met Lys Arg
65                  70                  75                  80
His Asp Phe Phe Lys Ser Ala Met Pro Glu Gly Tyr Val Gln Glu Arg
                85                  90                  95
Thr Ile Ser Phe Lys Asp Asp Gly Lys Tyr Lys Thr Arg Ala Val Val
            100                 105                 110
```

```
Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
            165                 170                 175

Gln Leu Ala Asp His Tyr Gln Gln Asn Thr Pro Ile Gly Asp Gly Pro
        180                 185                 190

Val Leu Leu Pro Asp Asn His Tyr Leu Ser Thr Gln Thr Val Leu Ser
        195                 200                 205

Lys Asp Pro Asn Glu Lys Gly Thr
        210                 215

<210> SEQ ID NO 5
<211> LENGTH: 651
<212> TYPE: DNA
<213> ORGANISM: Artificial
<220> FEATURE:
<223> OTHER INFORMATION: GFP variant fragment; sequence encoding
      fragment corresponding to beta-strands 1-10 A4; synthesized DNA
      sequence.

<400> SEQUENCE: 5
atgagcaaag gagaagaact tttcactgga gttgtcccaa ttcttgttga attagatgga      60
gatgttaatg ggcacaaatt ttctgtcaga ggagagggtg aaggtgatgc tacaaacgga     120
aaactcaccc ttaaattcat ttgcactact ggaaaactac ctgttccatg gccaacgctt     180
gtcactactc tgacctatgg tgttcaatgc ttttcccgtt atccggatca catgaaacag     240
catgactttt tcaagagtgc catgcccgaa ggttatgtac aggaacgcac tatatatttc     300
aaagatgacg ggaactacaa gacgcgtgct gtagtcaagt tgaaggtga taccccttgtt     360 aatcgtatcg agttaaaggg tactgatttt aagaagatg aaacattct cggacacaaa      420 ctcgagtaca ctttaactc acacaatgta tatatcacgg cagacaaaca aaagaatgga      480
atcaaagcta acttcacaat tcgccacaac gttgtagatg gttccgttca actagcagac     540
cattatcaac aaaatactcc aattggcgat ggccctgtcc ttttaccaga caaccattac     600 tgtcgacac aaactgtcct ttcgaaagat cccaacgaaa agggtaccta a               651

<210> SEQ ID NO 6
<211> LENGTH: 216
<212> TYPE: PRT
<213> ORGANISM: Artificial
<220> FEATURE:
<223> OTHER INFORMATION: GFP variant fragment; fragment corresponding to
      beta-strands 1-10 A4; expressed from synthesized DNA sequence.

<400> SEQUENCE: 6

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60
```

```
Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Tyr Phe Lys Asp Gly Asn Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Thr Ile Arg His Asn Val Val Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Thr
    210                 215

<210> SEQ ID NO 7
<211> LENGTH: 84
<212> TYPE: DNA
<213> ORGANISM: Artificial
<220> FEATURE:
<223> OTHER INFORMATION: GFP variant fragment; sequence encoding
      fragment corresponding to beta-strand 11, amino acids 214-238;
      synthesized DNA sequence.

<400> SEQUENCE: 7
aagcgtgacc acatggtcct tcttgagttt gtaactgctg ctgggattac acatggcatg      60
gatgagctct acaaaggtac ctaa                                            84

<210> SEQ ID NO 8
<211> LENGTH: 27
<212> TYPE: PRT
<213> ORGANISM: Artificial
<220> FEATURE:
<223> OTHER INFORMATION: GFP variant fragment; fragment corresponding to
      beta-strand 11, amino acids 214-238; expressed from synthesized
      DNA sequence.

<400> SEQUENCE: 8

Lys Arg Asp His Met Val Leu Leu Glu Phe Val Thr Ala Ala Gly Ile
  1               5                  10                  15

Thr His Gly Met Asp Glu Leu Tyr Lys Gly Thr
            20                  25

<210> SEQ ID NO 9
<211> LENGTH: 60
<212> TYPE: DNA
<213> ORGANISM: Artificial
<220> FEATURE:
<223> OTHER INFORMATION: GFP variant fragment; sequence encoding
      fragment corresponding to beta-strand 11, amino acids 214-230;
      synthesized DNA sequence.

<400> SEQUENCE: 9
aagcgtgacc acatggtcct tcttgagttt gtaactgctg ctgggattac aggtacctaa      60
```

```
<210> SEQ ID NO 10
<211> LENGTH: 19
<212> TYPE: PRT
<213> ORGANISM: Artificial
<220> FEATURE:
<223> OTHER INFORMATION: GFP variant fragment; fragment corresponding to
      beta-strand 11, amino acids 214-230; expressed from synthesized
      DNA sequence.

<400> SEQUENCE: 10

Lys Arg Asp His Met Val Leu Leu Glu Phe Val Thr Ala Ala Gly Ile
1               5                   10                  15

Thr Gly Thr

<210> SEQ ID NO 11
<211> LENGTH: 60
<212> TYPE: DNA
<213> ORGANISM: Artificial
<220> FEATURE:
<223> OTHER INFORMATION: GFP variant fragment; sequence encoding
      fragment corresponding to beta-strand 11, M1 mutant mutant;
      synthesized DNA sequence.

<400> SEQUENCE: 11
aagcgtgacc acatggtcct tcatgagttt gtaactgctg ctgggattac aggtacctaa      60

<210> SEQ ID NO 12
<211> LENGTH: 19
<212> TYPE: PRT
<213> ORGANISM: Artificial
<220> FEATURE:
<223> OTHER INFORMATION: GFP variant fragment; fragment corresponding to
      beta-strand 11, M1 mutant; expressed from synthesized DNA
      sequence.

<400> SEQUENCE: 12

Lys Arg Asp His Met Val Leu His Glu Phe Val Thr Ala Ala Gly Ile
1               5                   10                  15

Thr Gly Thr

<210> SEQ ID NO 13
<211> LENGTH: 54
<212> TYPE: DNA
<213> ORGANISM: Artificial
<220> FEATURE:
<223> OTHER INFORMATION: GFP variant fragment; sequence encoding
      fragment corresponding to beta-strand 11, M2 mutant; synthesized
      DNA sequence.

<400> SEQUENCE: 13
aagcgtgacc acatggtcct tcatgagtct gtaaatgctg ctgggggtac ctaa           54

<210> SEQ ID NO 14
<211> LENGTH: 17
<212> TYPE: PRT
<213> ORGANISM: Artificial
<220> FEATURE:
<223> OTHER INFORMATION: GFP variant fragment; fragment corresponding to
      beta-strand 11, M2 mutant; expressed from synthesized DNA
      sequence.

<400> SEQUENCE: 14

Lys Arg Asp His Met Val Leu His Glu Ser Val Asn Ala Ala Gly Gly
1               5                   10                  15

Thr
```

<210> SEQ ID NO 15
<211> LENGTH: 51
<212> TYPE: DNA
<213> ORGANISM: Artificial
<220> FEATURE:
<223> OTHER INFORMATION: GFP variant fragment; sequence encoding
      fragment corresponding to beta-strand 11, M3 mutant; synthesized
      DNA sequence.

<400> SEQUENCE: 15
cgtgaccaca tggtccttca tgagtctgta aatgctgctg ggattacata a            51

<210> SEQ ID NO 16
<211> LENGTH: 16
<212> TYPE: PRT
<213> ORGANISM: Artificial
<220> FEATURE:
<223> OTHER INFORMATION: GFP variant fragment; fragment corresponding to
      beta-strand 11, M3 mutant; expressed from synthesized DNA
      sequence.

<400> SEQUENCE: 16

Arg Asp His Met Val Leu His Glu Tyr Val Asn Ala Ala Gly Ile Thr
1               5                   10                  15

<210> SEQ ID NO 17
<211> LENGTH: 54
<212> TYPE: DNA
<213> ORGANISM: Artificial
<220> FEATURE:
<223> OTHER INFORMATION: GFP variant fragment; sequence encoding
      fragment corresponding to beta-strand 11, H7 HIS-tag; synthesized
      DNA sequence.

<400> SEQUENCE: 17
aagcatgacc acatgcacct tcatgagcat gtacatgctc atgggggtac ctaa         54

<210> SEQ ID NO 18
<211> LENGTH: 17
<212> TYPE: PRT
<213> ORGANISM: Artificial
<220> FEATURE:
<223> OTHER INFORMATION: GFP variant fragment; fragment corresponding to
      beta-strand 11, H7 HIS-tag; expressed from synthesized DNA
      sequence.

<400> SEQUENCE: 18

Lys His Asp His Met His Leu His Glu His Val His Ala His Gly Gly
1               5                   10                  15

Thr

<210> SEQ ID NO 19
<211> LENGTH: 51
<212> TYPE: DNA
<213> ORGANISM: Artificial
<220> FEATURE:
<223> OTHER INFORMATION: GFP variant fragment; sequence encoding
      fragment corresponding to beta-strand 11, H9 HIS-tag; synthesized
      DNA sequence.

<400> SEQUENCE: 19
catgaccaca tgcaccttca tgagcatgta catgctcatc accataccta a            51

<210> SEQ ID NO 20
<211> LENGTH: 16
<212> TYPE: PRT
<213> ORGANISM: Artificial
<220> FEATURE:

<223> OTHER INFORMATION: GFP variant fragment; fragment corresponding to
      beta-strand 11, H9 HIS-tag; expressed from synthesized DNA
      sequence.

<400> SEQUENCE: 20

His Asp His Met His Leu His Glu His Val His Ala His His His Thr
1               5                   10                  15

<210> SEQ ID NO 21
<211> LENGTH: 1775
<212> TYPE: DNA
<213> ORGANISM: Artificial
<220> FEATURE:
<223> OTHER INFORMATION: Unique genetic elements of pTET-SpecR
      expression vector of SEQ ID NO: 22; elements from T0 to AatII:tet
      repressor protein tetR and spectinomycin gene under control of
      kanamycin promoter and RBS controlling expression of tet
      repressor; synthesized DNA sequence.

<400> SEQUENCE: 21

| | | | |
|---|---|---|---|
| ttaagaccca | ctttcacatt | taagttgttt | ttctaatccg tatatgatca attcaaggcc | 60 |
| gaataagaag | gctggctctg | caccttggtg | atcaaataat tcgatagctt gtcgtaataa | 120 |
| tggcggcata | ctatcagtag | taggtgtttc | cctttcttct ttagcgactt gatgctcttg | 180 |
| atcttccaat | acgcaaccta | agtaaaatg | ccccacagcg ctgagtgcat ataatgcatt | 240 |
| ctctagtgaa | aaaccttgtt | ggcataaaaa | ggctaattga ttttcgagag tttcatactg | 300 |
| tttttctgta | ggccgtgtac | ctaaatgtac | ttttgctcca tcgcgatgac ttagtaaagc | 360 |
| acatctaaaa | cttttagcgt | tattacgtaa | aaaatcttgc cagcttttcc cttctaaagg | 420 |
| gcaaaagtga | gtatggtgcc | tatctaacat | ctcaatggct aaggcgtcga gcaaagcccg | 480 |
| cttattttt | acatgccaat | acaatgtagg | ctgctctaca cctagcttct gggcgagttt | 540 |
| acgggttgtt | aaaccttcga | ttccgacctc | attaagcagc tctaatgcgc tgttaatcac | 600 |
| tttacttta | tctaatctgg | acatcattaa | tgtttattga gctctcgaac cccagagtcc | 660 |
| cgcattattt | gccgactacc | ttggtgatct | cgcctttcac gtagtggaca aattcttcca | 720 |
| actgatctgc | gcgcgaggcc | aagcgatctt | cttcttgtcc aagataagcc tgtctagctt | 780 |
| caagtatgac | gggctgatac | tgggccggca | ggcgctccat tgcccagtcg gcagcgacat | 840 |
| ccttcggcgc | gattttgccg | gttactgcgc | tgtaccaaat gcgggacaac gtaagcacta | 900 |
| catttcgctc | atcgccagcc | cagtcgggcg | gcgagttcca tagcgttaag gtttcattta | 960 |
| gcgcctcaaa | tagatcctgt | tcaggaaccg | gatcaaagag ttcctccgcc gctggaccta | 1020 |
| ccaaggcaac | gctatgttct | cttgcttttg | tcagcaagat agccagatca atgtcgatcg | 1080 |
| tggctggctc | gaagatacct | gcaagaatgt | cattgcgctg ccattctcca aattgcagtt | 1140 |
| cgcgcttagc | tggataacgc | cacggaatga | tgtcgtcgtg cacaacaatg gtgacttcta | 1200 |
| cagcgcggag | aatctcgctc | tctccagggg | aagccgaagt ttccaaaagg tcgttgatca | 1260 |
| aagctcgccg | cgttgtttca | tcaagcctta | cggtcaccgt aaccagcaaa tcaatatcac | 1320 |
| tgtgtggctt | caggccgcca | tccactgcgg | agccgtacaa atgtacggcc agcaacgtcg | 1380 |
| gttcgagatg | gcgctcgatg | acgccaacta | cctctgatag ttgagtcgat acttcggcga | 1440 |
| tcaccgcttc | cctcatgatg | tttaactttg | ttttagggcg actgccctgc tgcgtaacat | 1500 |
| cgttgctgct | ccataaacatc | aaacatcgac | ccacggcgta acgcgcttgc tgcttggatg | 1560 |
| cccgaggcat | agactgtacc | ccaaaaaaac | atgtcataac aagccatgaa aaccgccact | 1620 |
| gcgccgttac | catgcgaaac | gatcctcatc | ctgtctcttg atcagatctt gatccctgc | 1680 |

```
gccatcagat ccttggcggc aagaaagcca tccagtttac tttgcagggc ttcccaacct    1740
taccagaggg cgccccagct ggcaattccg acgtc                               1775
```

<210> SEQ ID NO 22
<211> LENGTH: 3204
<212> TYPE: DNA
<213> ORGANISM: Artificial
<220> FEATURE:
<223> OTHER INFORMATION: Complete sequence of pTET-SpecR expression
      vector; synthesized DNA sequence.

<400> SEQUENCE: 22

```
tcgagtccct atcagtgata gagattgaca tccctatcag tgatagagat actgagcaca      60
tcagcaggac gcactgaccg agttcattaa agaggagaaa gatacccatg gcagcagcc     120 atcatcatca tcatcacagc agcggcctgg tgccgcgcgg cagccatatg ggtggcggtt     180
ctggatccgg aggcactagt ggtggcggct caggtaccta actcgagcac caccaccacc     240
accactgaga tccggctgct aacaaagccc gaaaggaagc tgagttggct gctgccaccg     300
ctgagcaata actagcataa cctctagagg catcaaataa aacgaaaggc tcagtcgaaa     360
gactgggcct ttcgttttat ctgttgtttg tcggtgaacg ctctcctgag taggacaaat     420
ccgccgccct agacctaggc gttcggctgc ggcgagcggt atcagctcac tcaaaggcgg     480
taatacggtt atccacagaa tcaggggata acgcaggaaa gaacatgtga gcaaaaggcc     540
agcaaaaggc caggaaccgt aaaaaggccg cgttgctggc gtttttccat aggctccgcc     600
cccctgacga gcatcacaaa aatcgacgct caagtcagag gtggcgaaac ccgacaggac     660
tataaagata ccaggcgttt ccccctggaa gctccctcgt gcgctctcct gttccgaccc     720
tgccgcttac cggatacctg tccgcctttc tcccttcggg aagcgtggcg ctttctcaat     780
gctcacgctg taggtatctc agttcggtgt aggtcgttcg ctccaagctg ggctgtgtgc     840
acgaaccccc cgttcagccc gaccgctgcg ccttatccgg taactatcgt cttgagtcca     900
acccggtaag acacgactta tcgccactgg cagcagccac tggtaacagg attagcagag     960
cgaggtatgt aggcggtgct acagagttct tgaagtggtg cctaactacg gctacacta    1020 gaaggacagt atttggtatc tgcgctctgc tgaagccagt taccttcgga aaaagagttg    1080
gtagctcttg atccgcaaa caaaccaccg ctggtagcgg tggtttttttt gtttgcaagc    1140 agcagattac gcgcagaaaa aaaggatctc aagaagatcc tttgatcttt tctacggggt    1200
ctgacgctca gtggaacgaa aactcacgtt aagggatttt ggtcatgact agcgcttgga    1260
ttctcaccaa taaaaaacgc ccggcggcaa ccgagcgttc tgaacaaatc cagatggagt    1320
tctgaggtca ttactggatc tatcaacagg agtccaagct taagacccac tttcacattt    1380 aagttgttttt tctaatccgt atatgatcaa ttcaaggccg aataagaagg ctggctctgc    1440
accttggtga tcaaataatt cgatagcttg tcgtaataat ggcggcatac tatcagtagt    1500
aggtgtttcc ctttcttctt tagcgacttg atgctcttga tcttccaata cgcaacctaa    1560
agtaaaatgc cccacagcgc tgagtgcata taatgcattc tctagtgaaa accttgttg    1620 gcataaaaag gctaattgat tttcgagagt ttcatactgt ttttctgtag gccgtgtacc    1680
taaatgtact tttgctccat cgcgatgact tagtaaagca catctaaaac ttttagcgtt    1740
attacgtaaa aaatcttgcc agctttcccc ttctaaaggg caaaagtgag tatggtgcct    1800
atctaacatc tcaatggcta aggcgtcgag caaagcccgc ttatttttta catgccaata    1860
caatgtaggc tgctctacac ctagcttctg ggcgagttta cggggttgtta aaccttcgat    1920
```

```
tccgacctca ttaagcagct ctaatgcgct gttaatcact ttacttttat ctaatctgga    1980
catcattaat gtttattgag ctctcgaacc ccagagtccc gcattatttg ccgactacct    2040
tggtgatctc gccttttcacg tagtggacaa attcttccaa ctgatctgcg cgcgaggcca    2100
agcgatcttc ttcttgtcca agataagcct gtctagcttc aagtatgacg ggctgatact    2160
gggccggcag cgcgctccatt gcccagtcgg cagcgacatc cttcggcgcg attttgccgg    2220
ttactgcgct gtaccaaatg cgggacaacg taagcactac atttcgctca tcgccagccc    2280
agtcgggcgg cgagttccat agcgttaagg tttcatttag cgcctcaaat agatcctgtt    2340
caggaaccgg atcaaagagt tcctccgccg ctggacctac caaggcaacg ctatgttctc    2400
ttgcttttgt cagcaagata gccagatcaa tgtcgatcgt ggctggctcg aagatacctg    2460
caagaatgtc attgcgctgc cattctccaa attgcagttc gcgcttagct ggataacgcc    2520
acggaatgat gtcgtcgtgc acaacaatgg tgacttctac agcgcggaga atctcgctct    2580
ctccagggga agccgaagtt ccaaaaggt cgttgatcaa agctcgccgc gttgtttcat    2640
caagccttac ggtcaccgta accagcaaat caatatcact gtgtggcttc aggccgccat    2700
ccactgcgga gccgtacaaa tgtacggcca gcaacgtcgg ttcgagatgg cgctcgatga    2760
cgccaactac ctctgatagt tgagtcgata cttcggcgat caccgcttcc ctcatgatgt    2820
ttaactttgt tttagggcga ctgccctgct gcgtaacatc gttgctgctc cataacatca    2880
aacatcgacc cacggcgtaa cgcgcttgct gcttggatgc ccgaggcata gactgtaccc    2940
caaaaaaaca tgtcataaca agccatgaaa accgccactg cgccgttacc atgcgaaacg    3000
atcctcatcc tgtctcttga tcagatcttg atcccctgcg ccatcagatc cttggcggca    3060
agaaagccat ccagtttact ttgcagggct tcccaacctt accagagggc gccccagctg    3120
gcaattccga cgtctaagaa accattatta tcatgacatt aacctataaa aataggcgta    3180
tcacgaggcc ctttcgtctt cacc    3204
```

<210> SEQ ID NO 23
<211> LENGTH: 596
<212> TYPE: DNA
<213> ORGANISM: Artificial
<220> FEATURE:
<223> OTHER INFORMATION: GFP variant fragment; sequence encoding fragment corresponding to beta-strands 1-9 OPT; synthesized DNA sequence.

<400> SEQUENCE: 23

```
atgcgcaaag gagaagaact tttcactgga gttgtcccaa ttcttgttga attagatggt     60
gatgttaatg ggcacaaatt ttctgtccgt ggagagggtg aaggtgatgc tacaaacgga    120
aaactcagcc ttaatttat ttgcactact ggaaaaactac ctgttccatg ccaacactt    180
gtcactactc tgacctatgg tgttcaatgc ttttcccgtt atccggatca catgaaacgg    240
catgactttt tcaagagtgt catgcccgaa ggttatgtac aggaacgcac tatatctttc    300
aaagatgacg ggacctacaa gacgcgtgct gaagtcaagt ctgaaggtga taccccttgtt    360
aatcgtatcg agttaaaagg tattgatttt aagaagatg gaacattctc ggacacaaa    420
ctcgagtaca acttttaactc acacaatgta tacatcacgg cagacaaaca aaagaatgga    480
atcaaagcta acttcacaat tcgccacaac gttgaagatg gttccgttca actagcagac    540
cattatcaac aaaatactcc aattggcgat ggccctgtcc ttttaccaga caataa       596
```

<210> SEQ ID NO 24
<211> LENGTH: 197

```
<212> TYPE: PRT
<213> ORGANISM: Artificial
<220> FEATURE:
<223> OTHER INFORMATION: GFP variant fragment; fragment corresponding to
      beta-strands 1-9 OPT; expressed from synthesized DNA sequence.

<400> SEQUENCE: 24

Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Ser Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Val Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Ser Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp
            195

<210> SEQ ID NO 25
<211> LENGTH: 41
<212> TYPE: PRT
<213> ORGANISM: Artificial
<220> FEATURE:
<223> OTHER INFORMATION: GFP variant fragment; fragment corresponding to
      beta-strands 10-11; expressed from synthesized DNA sequence.

<400> SEQUENCE: 25

Asn His Tyr Leu Ser Thr Gln Ser Val Leu Ser Lys Asp Pro Asn Glu
1               5                   10                  15

Lys Arg Asp His Met Val Leu Leu Glu Phe Val Thr Ala Ala Gly Ile
            20                  25                  30

Thr His Gly Met Asp Glu Leu Tyr Lys
        35                  40

<210> SEQ ID NO 26
<211> LENGTH: 41
<212> TYPE: PRT
<213> ORGANISM: Artificial
<220> FEATURE:
<223> OTHER INFORMATION: GFP variant fragment; fragment corresponding to
      beta-strands 10-11 OPT; expressed from synthesized DNA sequence.

<400> SEQUENCE: 26
```

Asp His Tyr Leu Ser Thr Gln Thr Ile Leu Ser Lys Asp Pro Asn Glu
1               5                   10                  15

Glu Arg Asp His Met Val Leu Leu Glu Ser Val Thr Ala Ala Gly Ile
                20                  25                  30

Thr His Gly Met Asp Leu Tyr Lys
        35                  40

<210> SEQ ID NO 27
<211> LENGTH: 71
<212> TYPE: PRT
<213> ORGANISM: Artificial
<220> FEATURE:
<223> OTHER INFORMATION: GFP variant fragment; fragment corresponding to
      beta-strands 10-x-11 in sandwich configuration; expressed from
      synthesized DNA sequence.

<400> SEQUENCE: 27

Tyr Thr Met Asp Leu Pro Asp Asn His Tyr Leu Ser Thr Gln Thr Ile
1               5                   10                  15

Leu Leu Lys Asp Leu Asn Gly Thr Gly Val Gly Ser Gly Gly Gly Ser
                20                  25                  30

His Met Gly Gly Gly Ser Gly Ser Gly Gly Gly Ser Gly Gly Gly Ser
        35                  40                  45

Thr Ser Glu Lys Arg Asp His Met Val Leu Leu Glu Tyr Val Thr Ala
    50                  55                  60

Ala Gly Ile Thr Asp Ala Ser
65                  70

<210> SEQ ID NO 28
<211> LENGTH: 71
<212> TYPE: PRT
<213> ORGANISM: Artificial
<220> FEATURE:
<223> OTHER INFORMATION: GFP variant fragment; fragment corresponding to
      beta-strands 10-x-11 in sandwich configuration, optimum; expressed
      from synthesized DNA sequence.

<400> SEQUENCE: 28

Tyr Thr Met Asp Leu Pro Asp Asp His Tyr Leu Ser Thr Gln Thr Ile
1               5                   10                  15

Leu Ser Lys Asp Leu Asn Gly Thr Asp Val Gly Ser Gly Gly Gly Ser
                20                  25                  30

His Met Gly Gly Gly Ser Gly Ser Gly Gly Gly Ser Gly Gly Gly Ser
        35                  40                  45

Thr Ser Glu Lys Arg Asp His Met Val Leu Leu Glu Tyr Val Thr Ala
    50                  55                  60

Ala Gly Ile Thr Asp Ala Ser
65                  70

<210> SEQ ID NO 29
<211> LENGTH: 693
<212> TYPE: DNA
<213> ORGANISM: Artificial
<220> FEATURE:
<223> OTHER INFORMATION: Sequence encoding GFP variant "GFP 1-10 OPT
      M2"; synthesized DNA sequence.

<400> SEQUENCE: 29
atgagcaaag gagaagaact tttcactgga gttgtcccaa ttcttgttga attagatggt      60
gatgttaatg gcacaaaatt ttctgtcaga ggagagggtg aaggtgatgc tacaatcgga     120
aaactcaccc ttaaatttat ttgcactact ggaaaactac ctgttccatg gccaacactt     180

-continued

```
gtcactactc tgacctatgg tgttcaatgc ttttcccgtt atccggatca catgaaaagg      240
catgactttt tcaagagtgc catgcccgaa ggttatgtac aggaacgcac tatatctttc      300
aaagatgacg ggaaatacaa gacgcgtgct gtagtcaagt ttgaaggtga tacccttgtt      360
aatcgtatcg agttaaaggg tactgatttt aaagaagatg gaaacattct cggacacaaa      420
ctcgagtaca actttaactc acacaatgta tacatcacgg cagacaaaca aaagaatgga      480
atcaaagcta acttcacagt tcgccacaac gttgaagatg gttccgttca actagcagac      540
cattatcaac aaaatactcc aattggcgat ggccctgtcc ttttaccaga caaccattac      600
ctgtcgacac aaactgtcct ttcgaaagat cccaacgaaa agcgtgacca catggtcctt      660
catgagtctg taaatgctgc tgggattaca taa                                  693
```

<210> SEQ ID NO 30
<211> LENGTH: 230
<212> TYPE: PRT
<213> ORGANISM: Artificial
<220> FEATURE:
<223> OTHER INFORMATION: GFP variant "GFP 1-10 OPT M2"; expressed from synthesized DNA sequence.

<400> SEQUENCE: 30

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Ser Val
    210                 215                 220

Asn Ala Ala Gly Ile Thr
225                 230
```

<210> SEQ ID NO 31
<211> LENGTH: 717
<212> TYPE: DNA

<213> ORGANISM: Artificial
<220> FEATURE:
<223> OTHER INFORMATION: Sequence encoding GFP variant "GFP 1-10 OPT M2
      tailed"; synthesized DNA sequence.

<400> SEQUENCE: 31

```
atgagcaaag gagaagaact tttcactgga gttgtcccaa ttcttgttga attagatggt      60
gatgttaatg ggcacaaatt ttctgtcaga ggagagggtg aaggtgatgc tacaatcgga    120
aaactcaccc ttaaatttat ttgcactact ggaaaactac ctgttccatg gccaacactt    180
gtcactactc tgacctatgg tgttcaatgc ttttcccgtt atccggatca catgaaaagg    240
catgactttt tcaagagtgc catgcccgaa ggttatgtac aggaacgcac tatatctttc    300
aaagatgacg ggaaatacaa gacgcgtgct gtagtcaagt ttgaaggtga tacccttgtt    360
aatcgtatcg agttaaaggg tactgatttt aaagaagatg gaaacattct cggacacaaa    420
ctcgagtaca actttaactc acacaatgta tacatcacgg cagacaaaca aaagaatgga    480
atcaaagcta acttcacagt tcgccacaac gttgaagatg gttccgttca actagcagac    540
cattatcaac aaaatactcc aattggcgat ggccctgtcc ttttaccaga caaccattac    600
ctgtcgacac aaactgtcct ttcgaaagat cccaacgaaa agcgtgacca catggtcctt    660
catgagtctg taaatgctgc tgggattaca catggcatgg atgagctcta caaataa       717
```

<210> SEQ ID NO 32
<211> LENGTH: 238
<212> TYPE: PRT
<213> ORGANISM: Artificial
<220> FEATURE:
<223> OTHER INFORMATION: GFP variant "GFP 1-10 OPT M2 tailed"; expressed
      from synthesized DNA sequence.

<400> SEQUENCE: 32

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190
```

```
Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Ser Val
    210                 215                 220

Asn Ala Ala Gly Ile Thr His Gly Met Asp Glu Leu Tyr Lys
225                 230                 235

<210> SEQ ID NO 33
<211> LENGTH: 124
<212> TYPE: DNA
<213> ORGANISM: Artificial
<220> FEATURE:
<223> OTHER INFORMATION: GFP variant fragment; sequence encoding
      fragment corresponding to beta-strands 10-11 OPT; expressed from
      synthesized DNA sequence.

<400> SEQUENCE: 33
gaccattacc tgtcgacaca aactatcctt tcgaaagatc ccaacgaaga gcgtgaccac      60
atggtccttc ttgagtctgt aactgctgct gggattacac atggcatgga tgagctctac     120
aaat                                                                   124

<210> SEQ ID NO 34
<211> LENGTH: 230
<212> TYPE: DNA
<213> ORGANISM: Artificial
<220> FEATURE:
<223> OTHER INFORMATION: GFP variant fragment; sequence encoding
      fragment corresponding to beta-strands 10-x-11 in sandwich
      configuration, optimum; expressed from synthesized DNA sequence.

<400> SEQUENCE: 34
gatataccat ggatttacca gacgaccatt acctgtcgac acaaactatc ctttcgaaag      60
atctcaacgg taccgacgtt gggtctggcg gtggctccca tgggtggc ggttctggat      120 ccggtggagg gtctggtggc ggatcaacta gtgaaaagcg tgaccacatg gtccttcttg     180
agtatgtaac tgctgctggg attacagatg ctagctaact cgagaatagc                 230

<210> SEQ ID NO 35
<211> LENGTH: 693
<212> TYPE: DNA
<213> ORGANISM: Artificial
<220> FEATURE:
<223> OTHER INFORMATION: GFP variant; sequence encoding "GFP 1-10 OPT
      M3"; expressed from synthesized DNA sequence.

<400> SEQUENCE: 35
atgagcaaag gagaagaact tttcactgga gttgtcccaa ttcttgttga attagatggt      60
gatgttaatg ggcacaaatt ttctgtcaga ggagagggtg aaggtgatgc tacaatcgga     120
aaactcaccc ttaaatttat ttgcactact ggaaaactac ctgttccatg ccaacactt     180 gtcactactc tgacctatgg tgttcaatgc ttttcccgtt atccggatca catgaaaagg     240
catgactttt tcaagagtgc catgcccgaa ggttatgtac aggaacgcac tatatctttc     300
aaagatgacg ggaaatacaa gacgcgtgct gtagtcaagt tgaaggtga tacccttgtt     360 aatcgtatcg agttaaaggg tactgatttt aaagaagatg aaacattct cggacacaaa      420 ctcgagtaca actttaactc acacaatgta tacatcacgg cagacaaaca aaagaatgga     480
atcaaagcta acttcacagt tgccacaaca gttgaagatg gttccgttca actagcagac     540
cattatcaac aaaatactcc aattggcgat ggccctgtcc ttttaccaga caaccattac     600
ctgtcgacac aaactgtcct ttcgaaagat cccaacgaaa gcgtgaccat ggtccctt      660
```
catgagtacg taaatgctgc tgggattaca taa                                       693

<210> SEQ ID NO 36
<211> LENGTH: 230
<212> TYPE: PRT
<213> ORGANISM: Artificial
<220> FEATURE:
<223> OTHER INFORMATION: GFP variant "GFP 1-10 OPT M3"; synthesized DNA
      sequence.

<400> SEQUENCE: 36

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Tyr Val
    210                 215                 220

Asn Ala Ala Gly Ile Thr
225                 230

<210> SEQ ID NO 37
<211> LENGTH: 717
<212> TYPE: DNA
<213> ORGANISM: Artificial
<220> FEATURE:
<223> OTHER INFORMATION: GFP variant; sequence encoding "GFP 1-10 OPT M3
      tailed"; synthesized DNA sequence.

<400> SEQUENCE: 37
atgagcaaag gagaagaact tttcactgga gttgtcccaa ttcttgttga attagatggt    60
gatgttaatg ggcacaaatt ttctgtcaga ggagagggtg aaggtgatgc tacaatcgga   120
aaactcaccc ttaaatttat ttgcactact ggaaaactac ctgttccatg gccaacactt   180
gtcactactc tgacctatgg tgttcaatgc ttttcccgtt atccggatca catgaaaagg   240
catgactttt tcaagagtgc catgcccgaa ggttatgtac aggaacgcac tatatctttc   300

```
aaagatgacg ggaaatacaa gacgcgtgct gtagtcaagt ttgaaggtga taccttgtt    360 aatcgtatcg agttaaaggg tactgatttt aagaagatg gaaacattct cggacacaaa    420
ctcgagtaca actttaactc acacaatgta tacatcacgg cagacaaaca aaagaatgga    480
atcaaagcta acttcacagt tcgccacaac gttgaagatg gttccgttca actagcagac    540
cattatcaac aaaatactcc aattggcgat ggccctgtcc ttttaccaga caaccattac    600
ctgtcgacac aaactgtcct ttcgaaagat cccaacgaaa agcgtgacca catggtcctt    660
catgagtacg taaatgctgc tgggattaca catggcatgg atgagctcta caaataa      717
```

<210> SEQ ID NO 38
<211> LENGTH: 238
<212> TYPE: PRT
<213> ORGANISM: Artificial
<220> FEATURE:
<223> OTHER INFORMATION: GFP variant "GFP 1-10 OPT M3 tailed"; expressed from synthesized DNA sequence.

<400> SEQUENCE: 38

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Tyr Val
    210                 215                 220

Asn Ala Ala Gly Ile Thr His Gly Met Asp Glu Leu Tyr Lys
225                 230                 235
```

<210> SEQ ID NO 39
<211> LENGTH: 431
<212> TYPE: DNA
<213> ORGANISM: Artificial
<220> FEATURE:
<223> OTHER INFORMATION: GFP variant fragment; sequence encoding fragment corresponding to beta-strand 10 in fusion with FRB protein and C-terminal 6-HIS tag; synthesized DNA sequence.

<400> SEQUENCE: 39

```
ccatggattt accagacgac cattacctgt cgacacaaac tatcctttcg aaagatctca      60
acggaactga cgttgggtct ggcggtggtt cccatatgga gctgatccga gtggccatcc     120
tctggcatga gatgtggcat gaaggcctgg aagaggcatc tcgtttgtac tttggggaaa     180
ggaacgtgaa aggcatgttt gaggtgctgg agcccttgca tgctatgatg aacggggcc      240
cccagactct gaaggaaaca tcctttaatc aggcctatgg tcgagattta atggaggccc     300
aagagtggtg caggaagtac atgaaatcag ggaatgtcaa ggacctcacc caagcctggg     360
acctctatta tcatgtgttc cgacgaatct caaagcaggg taccctcgag caccaccacc     420
accaccactg a                                                          431
```

<210> SEQ ID NO 40
<211> LENGTH: 142
<212> TYPE: PRT
<213> ORGANISM: Artificial
<220> FEATURE:
<223> OTHER INFORMATION: GFP variant fragment; fragment corresponding to
      beta-strand 10 in fusion with FRB protein and C-terminal 6-HIS
      tag; expressed from synthesized DNA sequence.

<400> SEQUENCE: 40

```
Met Asp Leu Pro Asp Asp His Tyr Leu Ser Thr Gln Thr Ile Leu Ser
1               5                   10                  15

Lys Asp Leu Asn Gly Thr Asp Val Gly Ser Gly Gly Ser His Met
            20                  25                  30

Glu Leu Ile Arg Val Ala Ile Leu Trp His Glu Met Trp His Glu Gly
        35                  40                  45

Leu Glu Glu Ala Ser Arg Leu Tyr Phe Gly Glu Arg Asn Val Lys Gly
    50                  55                  60

Met Phe Glu Val Leu Glu Pro Leu His Ala Met Met Glu Arg Gly Pro
65                  70                  75                  80

Gln Thr Leu Lys Glu Thr Ser Phe Asn Gln Ala Tyr Gly Arg Asp Leu
                85                  90                  95

Met Glu Ala Gln Glu Trp Cys Arg Lys Tyr Met Lys Ser Gly Asn Val
            100                 105                 110

Lys Asp Leu Thr Gln Ala Trp Asp Leu Tyr Tyr His Val Phe Arg Arg
        115                 120                 125

Ile Ser Lys Gln Gly Thr Leu Glu His His His His His His
    130                 135                 140
```

<210> SEQ ID NO 41
<211> LENGTH: 497
<212> TYPE: DNA
<213> ORGANISM: Artificial
<220> FEATURE:
<223> OTHER INFORMATION: GFP variant fragment; sequence encoding
      fragment corresponding to beta-strands 12-11 in fusion with Fkbp
      protein and N-terminal 6-HIS tag; synthesized DNA sequence.

<400> SEQUENCE: 41

```
ccatgggcag cagccatcat catcatcatc acagcagcgg cctggtgccg cgcggcagcc      60
atatgggtgg cactagtgga gtgcaggtgg aaaccatctc cccaggaaac gggcgcacct     120
tccccaagcg cggccagacc tgcgtggtgc actacaccgg gatgcttgaa gatggaaaga     180
aatttgattc ctcccgggac agaaacaagc cctttaagtt tatgctaggc aagcaggagg     240
```

```
tgatccgagg ctgggaagaa ggggttgccc agatgagtgt gggtcagaga gccaaactga    300
ctatatcacc tgactatgca tacggagcta caggtcatcc tggaattatt ccacctcacg    360
ctactctcgt cttcgatgtg gagcttctaa aactggaagg atccggtgga gggtctggtg    420
gcggatcaac atctgaaaag cgtgaccaca tggtccttga gtatgtaact gctgctggga    480
ttacagatgc atcttaa                                                    497
```

```
<210> SEQ ID NO 42
<211> LENGTH: 164
<212> TYPE: PRT
<213> ORGANISM: Artificial
<220> FEATURE:
<223> OTHER INFORMATION: GFP variant fragment; fragment corresponding to
      beta-strands 12-11 in fusion with Fkbp protein and N-terminal
      6-HIS tag; expressed from synthesized DNA sequence.

<400> SEQUENCE: 42

Met Gly Ser Ser His His His His His His Ser Ser Gly Leu Val Pro
1               5                   10                  15

Arg Gly Ser His Met Gly Gly Thr Ser Gly Val Gln Val Glu Thr Ile
            20                  25                  30

Ser Pro Gly Asn Gly Arg Thr Phe Pro Lys Arg Gly Gln Thr Cys Val
        35                  40                  45

Val His Tyr Thr Gly Met Leu Glu Asp Gly Lys Lys Phe Asp Ser Ser
    50                  55                  60

Arg Asp Arg Asn Lys Pro Phe Lys Phe Met Leu Gly Lys Gln Glu Val
65                  70                  75                  80

Ile Arg Gly Trp Glu Glu Gly Val Ala Gln Met Ser Val Gly Gln Arg
                85                  90                  95

Ala Lys Leu Thr Ile Ser Pro Asp Tyr Ala Tyr Gly Ala Thr Gly His
            100                 105                 110

Pro Gly Ile Ile Pro Pro His Ala Thr Leu Val Phe Asp Val Glu Leu
        115                 120                 125

Leu Lys Leu Glu Gly Ser Gly Gly Ser Gly Gly Gly Ser Thr Ser
    130                 135                 140

Glu Lys Arg Asp His Met Val Leu Glu Tyr Val Thr Ala Ala Gly Ile
145                 150                 155                 160

Thr Asp Ala Ser
```

```
<210> SEQ ID NO 43
<211> LENGTH: 8
<212> TYPE: PRT
<213> ORGANISM: Artificial
<220> FEATURE:
<223> OTHER INFORMATION: Polypeptide linker; expressed from synthesized
      DNA sequence.

<400> SEQUENCE: 43

Gly Gly Gly Ser Gly Ser Gly Gly
1               5
```

```
<210> SEQ ID NO 44
<211> LENGTH: 4
<212> TYPE: PRT
<213> ORGANISM: Artificial
<220> FEATURE:
<223> OTHER INFORMATION: Polypeptide linker; expressed from synthesized
      DNA sequence.

<400> SEQUENCE: 44
```

```
Gly Gly Gly Ser
1

<210> SEQ ID NO 45
<211> LENGTH: 113
<212> TYPE: DNA
<213> ORGANISM: Artificial
<220> FEATURE:
<223> OTHER INFORMATION: Sequence of closing cassette flanked by NcoI
      and KpnI restriction sites; synthesized DNA sequence.

<400> SEQUENCE: 45
ccatgggcag cagccatcat catcatcatc acagcagcgg cctggtgccg cgcggcagcc      60
atatgggtgg cggttctgga tccggaggca ctagtggtgg cggctcaggt acc            113

<210> SEQ ID NO 46
<211> LENGTH: 26
<212> TYPE: DNA
<213> ORGANISM: Artificial
<220> FEATURE:
<223> OTHER INFORMATION: Sequence of frame-shift stuffer; synthesized
      DNA sequence.

<400> SEQUENCE: 46
catatgtgtt aactgagtag gatccg                                          26

<210> SEQ ID NO 47
<211> LENGTH: 26
<212> TYPE: DNA
<213> ORGANISM: Artificial
<220> FEATURE:
<223> OTHER INFORMATION: Sequence of frame-shift stuffer; synthesized
      DNA sequence.

<400> SEQUENCE: 47
catatgtaat taattaattg gatccg                                          26

<210> SEQ ID NO 48
<211> LENGTH: 40
<212> TYPE: DNA
<213> ORGANISM: Artificial
<220> FEATURE:
<223> OTHER INFORMATION: Synthetic primer sequence; synthesized DNA
      sequence.

<400> SEQUENCE: 48
caggatgagg atcgtttcgc atggtaacgg cgcagtggcg                           40

<210> SEQ ID NO 49
<211> LENGTH: 40
<212> TYPE: DNA
<213> ORGANISM: Artificial
<220> FEATURE:
<223> OTHER INFORMATION: Synthetic primer sequence; synthesized DNA
      sequence.

<400> SEQUENCE: 49
cgccactgcg ccgttaccat gcgaaacgat cctcatcctg                           40

<210> SEQ ID NO 50
<211> LENGTH: 33
<212> TYPE: DNA
<213> ORGANISM: Artificial
<220> FEATURE:
<223> OTHER INFORMATION: Synthetic primer sequence; synthesized DNA
      sequence.
```

```
<400> SEQUENCE: 50
gcattatttg ccgactacct tggtgatctc gcc                                33

<210> SEQ ID NO 51
<211> LENGTH: 34
<212> TYPE: DNA
<213> ORGANISM: Artificial
<220> FEATURE:
<223> OTHER INFORMATION: Synthetic primer sequence; synthesized DNA
      sequence.

<400> SEQUENCE: 51
accccagagt cccgcattat ttgccgacta cctt                               34

<210> SEQ ID NO 52
<211> LENGTH: 63
<212> TYPE: DNA
<213> ORGANISM: Artificial
<220> FEATURE:
<223> OTHER INFORMATION: Synthetic stuffer sequence; synthesized DNA
      sequence.

<400> SEQUENCE: 52
catatgggtg gcggttctgg atccggaggc actagtggtg gcggctcagg tacctaactc   60
gag                                                                 63

<210> SEQ ID NO 53
<211> LENGTH: 45
<212> TYPE: DNA
<213> ORGANISM: Artificial
<220> FEATURE:
<223> OTHER INFORMATION: Synthetic stuffer sequence; synthesized DNA
      sequence.

<400> SEQUENCE: 53
catatgggtg gcactagtgg tggcggctca ggtacctaac tcgag                   45

<210> SEQ ID NO 54
<211> LENGTH: 14
<212> TYPE: DNA
<213> ORGANISM: Artificial
<220> FEATURE:
<223> OTHER INFORMATION: Optimal Shine-Delgarno sequence for optimal
      tetR sequence; synthesized DNA sequence.

<400> SEQUENCE: 54
aataaacatt aatg                                                     14

<210> SEQ ID NO 55
<211> LENGTH: 6
<212> TYPE: PRT
<213> ORGANISM: Artificial
<220> FEATURE:
<223> OTHER INFORMATION: pTET vector sequence; expressed from
      synthesized DNA sequence.

<400> SEQUENCE: 55

Asp Pro Ala Ala Asn Lys
1               5

<210> SEQ ID NO 56
<211> LENGTH: 4
<212> TYPE: PRT
<213> ORGANISM: Artificial
<220> FEATURE:
<223> OTHER INFORMATION: pTET vector sequence; expressed from
```

-continued

```
                synthesized DNA sequence.

<400> SEQUENCE: 56

Leu Glu Asn Ser
1
```